(12) United States Patent
Li

(10) Patent No.: US 11,400,142 B2
(45) Date of Patent: *Aug. 2, 2022

(54) TREATMENT OF DIABETIC NERVE INJURY COMPRISING ADMINISTERING PLASMINOGEN

(71) Applicant: TALENGEN INTERNATIONAL LIMITED, Hong Kong (CN)

(72) Inventor: Jinan Li, Shenzhen (CN)

(73) Assignee: Talengen International Limited, Hong Kong (CN)

(*) Notice: Subject to any disclaimer, the term of this patent is extended or adjusted under 35 U.S.C. 154(b) by 385 days.

This patent is subject to a terminal disclaimer.

(21) Appl. No.: 16/062,037

(22) PCT Filed: Dec. 16, 2016

(86) PCT No.: PCT/CN2016/110449
§ 371 (c)(1),
(2) Date: Jun. 13, 2018

(87) PCT Pub. No.: WO2017/101867
PCT Pub. Date: Jun. 22, 2017

(65) Prior Publication Data
US 2018/0369345 A1 Dec. 27, 2018

(30) Foreign Application Priority Data
Dec. 18, 2015 (WO) ................ PCT/CN2015/097943

(51) Int. Cl.
| | | |
|---|---|---|
| A61K 38/48 | (2006.01) | |
| A61K 38/00 | (2006.01) | |
| A61P 25/02 | (2006.01) | |
| A61K 9/00 | (2006.01) | |
| A61K 45/06 | (2006.01) | |

(52) U.S. Cl.
CPC ............ *A61K 38/484* (2013.01); *A61K 38/00* (2013.01); *A61P 25/02* (2018.01); *A61K 9/0019* (2013.01); *A61K 9/0073* (2013.01); *A61K 45/06* (2013.01); *A61K 2300/00* (2013.01); *C12Y 304/21007* (2013.01)

(58) Field of Classification Search
None
See application file for complete search history.

(56) References Cited

U.S. PATENT DOCUMENTS

| | | |
|---|---|---|
| 11,129,880 B2 | 9/2021 | Li |
| 2003/0113313 A1 | 6/2003 | Peyman |
| 2003/0147876 A1 | 8/2003 | Ni |
| 2003/0180934 A1 | 9/2003 | Ni et al. |
| 2005/0250694 A1* | 11/2005 | Ma ................ A61K 38/484 |
| | | 514/8.1 |
| 2006/0234913 A1* | 10/2006 | Arbit ................ A61P 9/00 |
| | | 514/1.9 |
| 2007/0185017 A1* | 8/2007 | Aggarwal ............ C07K 14/47 |
| | | 514/1.7 |
| 2007/0196350 A1 | 8/2007 | Bartels |
| 2009/0208448 A1 | 8/2009 | Solomon |
| 2013/0273028 A1 | 10/2013 | Zwaal |
| 2018/0360930 A1 | 12/2018 | Li |
| 2019/0015485 A1 | 1/2019 | Li |
| 2019/0307861 A1 | 10/2019 | Li |
| 2019/0314464 A1 | 10/2019 | Li |
| 2019/0314465 A1 | 10/2019 | Li |

FOREIGN PATENT DOCUMENTS

| | | |
|---|---|---|
| CA | 2703494 A1 | 4/2009 |
| CA | 3002915 A1 | 5/2017 |
| CN | 1451746 A | 10/2003 |
| CN | 1585649 A | 2/2005 |
| CN | 1191856 C | 3/2005 |
| CN | 1643140 A | 7/2005 |
| CN | 1768138 A | 5/2006 |
| CN | 1946352 A | 4/2007 |
| CN | 1961958 A | 5/2007 |
| CN | 1990871 A | 7/2007 |
| CN | 101002888 A | 7/2007 |
| CN | 101563100 A | 10/2009 |
| CN | 101573134 A | 11/2009 |
| CN | 101918548 A | 12/2010 |
| CN | 102121023 A | 7/2011 |
| CN | 102154253 A | 8/2011 |
| CN | 102250210 A | 11/2011 |
| CN | 102872020 A | 1/2013 |
| CN | 103384722 A | 11/2013 |
| CN | 103764163 A | 4/2014 |
| CN | 104789544 A | 7/2015 |
| CN | 105008323 A | 10/2015 |
| CN | 105705520 A | 6/2016 |

(Continued)

OTHER PUBLICATIONS

Martin-Fernandez et al., Scientific Reports, 2016; 6: 39255; doi: 10.1038/srep39255; 7 pages total (Year: 2016).*
Ma et al., Blood, 2014; 124: 3155-3164 (Year: 2014).*
Bhattacharya et al. (PLoS ONE 12(3): e0171355. https://doi.org/10.1371/journal.pone.0171355; 22 pages total (Year: 2017).*
Zhang et al., J Am Soc Nephrol, 2006; 17: 475-486 (Year: 2006).*
Michael J. Fowler, Clinical Diabetes, 2008; 26: 77-82 (Year: 2008).*
Dyck et al., Neurology, 1993; 43: 817-824 (Year: 1993).*
Izenberg et al., Semin Neruol 2015; 35: 424-430 (Year: 2015).*
Ajjan, R.A. et al. (Jul. 4, 2013)."Diabetes Is Associated With Posttranslational Modifications In Plasminogen Resulting In Reduced Plasmin Generation and Enzyme-Specific Activity." *Blood* 122(1):134-142.

(Continued)

*Primary Examiner* — Christina M Borgeest
(74) *Attorney, Agent, or Firm* — Morrison & Foerster LLP

(57) ABSTRACT

The present invention relates to the use of plasminogen in the prevention and/or treatment of diabetic neuropathic pain and neurohypersensitivity, and in the repair of nerve tissue injury. Therefore, plasminogen may become a new strategy for preventing and treating diabetic neuropathic pain.

20 Claims, 13 Drawing Sheets

Specification includes a Sequence Listing.

(56) References Cited

FOREIGN PATENT DOCUMENTS

| | | |
|---|---|---|
| EP | 3395360 A1 | 10/2018 |
| JP | 2002510209 A | 4/2002 |
| JP | 2009-196927 A | 9/2009 |
| JP | 2019500422 A | 1/2019 |
| JP | 2020502140 A | 1/2020 |
| JP | 2020502150 A | 1/2020 |
| JP | 2020502151 A | 1/2020 |
| JP | 2020510628 A | 4/2020 |
| TW | 200803890 A | 1/2008 |
| TW | 201625294 A | 7/2016 |
| TW | 201822800 A | 7/2018 |
| TW | 201822801 A | 7/2018 |
| TW | 201822802 A | 7/2018 |
| TW | 201822803 A | 7/2018 |
| TW | 201822804 A | 7/2018 |
| TW | 201822807 A | 7/2018 |
| TW | 201822808 A | 7/2018 |
| WO | WO199900420 A1 | 1/1999 |
| WO | WO200018436 A1 | 4/2000 |
| WO | WO-2003/020297 A2 | 3/2003 |
| WO | WO-2003/020297 A3 | 3/2003 |
| WO | WO2003066842 A2 | 8/2003 |
| WO | WO2003095637 A1 | 11/2003 |
| WO | WO2004039956 A2 | 5/2004 |
| WO | WO2003066842 A3 | 6/2004 |
| WO | WO2004052228 A2 | 6/2004 |
| WO | WO2004052228 A3 | 10/2004 |
| WO | 2007101005 A2 | 9/2007 |
| WO | WO-2008/026999 A2 | 3/2008 |
| WO | WO-2008/026999 A3 | 3/2008 |
| WO | 2007101005 A3 | 6/2008 |
| WO | WO2004039956 A3 | 4/2009 |
| WO | WO2009073471 A1 | 6/2009 |
| WO | WO2012093132 A1 | 7/2012 |
| WO | WO2013024074 A1 | 2/2013 |
| WO | WO2014070983 A1 | 5/2014 |
| WO | WO2014070986 A1 | 5/2014 |
| WO | WO2015023752 A1 | 2/2015 |
| WO | WO2016095013 A1 | 6/2016 |
| WO | 2017077380 A1 | 5/2017 |
| WO | WO2017101866 A1 | 6/2017 |
| WO | WO2017101868 A1 | 6/2017 |

OTHER PUBLICATIONS

Andreasen, P.A. et al. (1997). "The Urokinase-Type Plasminogen Activator System In Cancer Metastasis: A Review," *Int. J. Cancer* 72:1-22.
Chen, W. (Apr. 15, 2007). "Pilot Production and Pharmacodynamics Study Of Recombinant Human Microplasminogen," Doctoral Dissertation, Fudan University, 127 pages. (With English Abstract).
Collen, D. et al. (Dec. 15, 1991) "Review Article: Basic and Clinical Aspects of Fibrinolysis and Thrombolysis," *Blood* 78(12):3114-3124.
Collen, D. (2001). "Ham-Wasserman Lecture: Role Of The Plasminogen System In Fibrin-Homeostasis and Tissue Remodeling," *Hematology* pp. 1-9.
Davalos, D. et al. (2012, e-pub. Oct. 31, 2011). "Fibrinogen As A Key Regulator Of Inflammation In Disease," *Semin. Immunopathol.* 34:43-62.
Du, Z. et al. (Dec. 31, 1997). "Changes Of Plasm tPA and PAI Activities In Patients With Diabetic Retinopathy," *Eye Science* 13(1): 17-20.
Gao, C. et al. (Feb. 2007). "Relationship Between Type Diabetic Retinopathy and Plasma Fibrinolysis," *Progress In Modern Biomedicine* 7(2):257-258. (With English Abstract).
Hay, E.D. (1991). Cell Biology Of Extracellular Matrix, 2nd Ed. Springer Science+Business Media, LLC., 15 pages. Table of Contents.
He, C. et al. (Apr. 1989). "Tissue Cooperation In A Proteolytic Cascade Activating Human Interstitial Collagenase," *Proc. Natl. Acad. Sci. USA* 86:2632-2636.

Hunt, J.A. et al. (2008, e-pub. Aug. 14, 2008). "Simplified Recombinant Plasmin Production and Functional Comparison Of A Novel Thrombolytic Molecule With Plasma-Derived Plasmin," *Thromb. Haemost.* 100:413-419.
Jin, X. et al. (Aug. 2002). "Catabolic Enzymes Of Extracellular Matrix and Diabetic Nephropathy," *Medical Journal Of The Chinese Coal Industry* 5(8):825-826. With English Translation.
Knudsen, B.S. et al. (Aug. 15, 1986). "Binding of Plasminogen to Extracellular Matrix," *The Journal Of Biological Chemistry* 261 (23): 10765-10771.
Lee, H.B. et al. (2005). "Plasminogen Activator Inhibitor-1 and Diabetic Nephropathy," *Nephrology* 10:S11-S13.
Li, J. et al. (Sep. 2008). "Catabolic Enzymes Of Extracellular Matrix and Diatetic Nephropathy," *Medical Recapitulate* 14(17):2611-2613. (English Translation Abstract Only).
Marder, V. J. et al. (2010). "Direct Fibrinolytic Agents: Biochemical Attributes, Preclinical Foundation and Clinical Potential," *J. Thromb. Haemost.* 8:433-444.
Mignatti, P. et al. (Jan. 1993). "Biology and Biochemistry of Proteinases in Tumor Invasion," *Physiological Reviews* 73(1): 161-195.
Nagai, N. et al. (2002). "Recombinant Human Microplasmin: Production and Potential Therapeutic Properties," *Journal Of Thrombosis and Haemostasis* 1:307-313.
Raum, D. et al. (May 30, 1980). "Synthesis Of Human Plasminogen By The Liver," *Science* 208(4447):1036-1037, 4 pages.
Rifkin, D.B. et al. (1990). "Growth Factor Control Of Extracellular Proteolysis," *Cell Differentiation and Development* 32:313-318.
Rifkin, D.B. et al. (1999). "Proteolytic Control Of Growth Factor Availability," *APMIS* 107:80-85.
Ryu, J.K. et al. (Sep. 10, 2015). "Blood Coagulation Protein Fibrinogen Promotes Autoimmunity and Demyelination Via Chemokine Release And Antigen Presentation," *Nature Communication* 6:8164, 15 pages.
Saksela, O. et al. (1988). "Cell-Associated Plasminogen Activation: Regulation and Physiological Functions," *Ann. Rev. Cell Biol.* 4:93-126.
Shen, Y. et al. (Jun. 14, 2012). "Plasminogen Is A Key Proinflammatory Regulator That Accelerates The Healing Of Acute and Diabetic Wounds," *Blood* 119(24):5879-5887.
Shi, L. et al. (Nov. 30, 2005). "Comparison of Curative Effects of Kallidinogenase Between Patients with Early Diabetic Nephropathy and Patients with Clinical Diabetic Nephropathy," *Journal Of Jilin University (Medicine Edition)*, 31(6):934-936. (With English Abstract).
Singh, R. et al. (Dec. 21, 2014). "Diabetic Peripheral Neuropathy: Current Perspective and Future Directions," *Pharmacological Research* 80:21-35.
Sottrup-Jensen, L. et al. (Jul. 1975). "Amino-acid Sequence Of Activation Cleavage Site In Plasminogen: Homology With 'Pro' Part Of Prothrombin," *Proc. Natl. Acad. Sci. USA* 72(7):2577-2581.
Stoppelli, M.P. et al. (Aug. 1985). "Differentiation-enhanced Binding Of The Amino-Terminal Fragment Of Human Urokinase Plasminogen Activator To A Specific Receptor On U937 Monocytes," *Proc. Natl. Acad. Sci. USA* 82:4939-4973.
Tyagi, S.C. (1997). "Proteinases and Myocardial Extracellular Matrix Turnover," *Molecular and Cellular Biochemistry* 168:1-12.
Valvi, D. et al. (Mar. 6, 2012). "Fibrinogen, Chronic Obstructive Pulmonary Disease (COPD) and Outcomes In Two United States Cohorts," *International Journal Of COPD* 7:173-182.
Vassalli, J.-D. et al. (Jan. 1985). "A Cellular Binding Site for the $M_r$ 55,000 Form of the Human Plasminogen Activator, Urokinase," *The Journal Of Cell Biology* 100:86-92.
Wang, X. (Mar. 31, 2014). "Medical Treatment Of Painful Diabetic Neuropathy," *Journal of Community Medicine* 12(6):82 & 83, with English Translation Abstract.
Werb, Z. et al. (May 5, 1977). "Endogenous Activation Of Latent Collagenase By Rheumatoid Synovial Cells," *The New England Journal Of Medicine* 296(18):1017-1023.
Wiman, B. et al. (1975). "Structural Relationship between 'Glutamic Acid' and 'Lysine' Forms of Human Plasminogen and Their Interaction with the NH,-Terminal Activation Peptide as Studied by Affinity Chromatography," *Eur. J. Biochem* 50:489-494.

(56) References Cited

OTHER PUBLICATIONS

Xu, A. et al. (Feb. 28, 2014). "New Progress In The Treatment Of Diabetic Neuropathic Pain," *Chinese Journal OF Clinical Research* 27(2):227,228 & 230, with English Translation Abstract.

Yin, G. et al. (2005) "Cloning Construction and Purification Of Recombinant Human Plasminogen Kringle 5 Gene," *Academic Journal Of Shanghai Second Medical University* 25(2):151-154. (English Translation of the Abstract).

International Search Report, dated Mar. 21, 2017, for PCT Application No. PCT/CN2016/110449, filed Dec. 16, 2016, 6 pages.

International Search Report, dated Mar. 2, 2017, for PCT Application No. PCT/CN2016/110450, filed Dec. 16, 2016, 4 pages.

International Search Report, dated Feb. 24, 2017, for PCT Application No. PCT/CN2016/110452, filed Dec. 16, 2016, 4 pages.

U.S. Appl. No. 16/063,569, Li, J., filed Jun. 18, 2018. (Copy not submitted herewith pursuant to the waiver of 37 C.F.R. § 1.98(a)(2)(iii) issued by the Office on Sep. 21, 2004).

U.S. Appl. No. 16/063,534, Li, J., filed Jun. 18, 2018. (Copy not submitted herewith pursuant to the waiver of 37 C.F.R. § 1.98(a)(2)(iii) issued by the Office on Sep. 21, 2004).

U.S. Appl. No. 16/062,410, Li, J., filed Jun. 14, 2018. (Copy not submitted herewith pursuant to the waiver of 37 C.F.R. § 1.98(a)(2)(iii) issued by the Office on Sep. 21, 2004).

U.S. Appl. No. 16/062,421, Li, J., filed Jun. 14, 2018. (Copy not submitted herewith pursuant to the waiver of 37 C.F.R. § 1.98(a)(2)(iii) issued by the Office on Sep. 21, 2004).

U.S. Appl. No. 16/062,389, Li, J., filed Jun. 14, 2018. (Copy not submitted herewith pursuant to the waiver of 37 C.F.R. § 1.98(a)(2)(iii) issued by the Office on Sep. 21, 2004).

U.S. Appl. No. 16/062,049, Li, J., filed Jun. 13, 2018. (Copy not submitted herewith pursuant to the waiver of 37 C.F.R. § 1.98(a)(2)(iii) issued by the Office on Sep. 21, 2004).

U.S. Appl. No. 16/062,052, Li, J., filed Jun. 13, 2018. (Copy not submitted herewith pursuant to the waiver of 37 C.F.R. § 1.98(a)(2)(iii) issued by the Office on Sep. 21, 2004).

Akassoglou, K. et al. (May 29, 2000). "Tissue Plasminogen Activator-Mediated Fibrinolysis Protects Against Axonal Degeneration and Demyelination after Sciatic Nerve Injury," J Cell Biol. 149(5):1157-1166.

Auwerx, J. et al. (Jan./Feb. 1988). "Tissue-Type Plasminogen Activator Antigen and Plasminogen Activator Inhibitor in Diabetes Mellitus," Arteriosclerosis 8(1):68-72.

Brazionis, L. et al. (Apr. 2008). "Plasminogen Activator Inhibitor-1 Activity in Type 2 Diabetes A Different Relationship With Coronary Heart Disease and Diabetic Retinopathy," Arterioscler Thromb Vase. Biol. 28:786-791.

Fisher, E.J. et al. (1997). "Displacement of Tissue Bound Plasminogen By Glucose: A Possible Mechanism in the Pathogenesis of Diabetic Nephropathy," Endocrinology and Metabolism 4:371-376. 8 pages.

Gutiérrez-Fernández, A. et al. (Oct. 7, 2009). "Plasminogen Enhances Neuritogenesis on Laminin-1," J Neurosci. 29(40):12393-12400, 17 pages.

Hafer-Macko, C.E. et al. (Jul. 17, 2007). "Microvascular Tissue Plasminogen Activator Is Reduced In Diabetic Neuropathy," Neurology 69(3):268-274.

Kimiyoshi, A. et al. (2009). "Diabetes and Peripheral Neuropathy," Forefront of Medicine and Medical Care 98 (2):399-405, 20 pages. English Translation.

Lugea, A. et al. (Sep. 2006). "Pancreas Recovery Following Caerulein-Induced Pancreatitis is Impaired in Plasminogen Deficient Mice," Gastroenterology 131(3):885-899, 32 pages.

Ma, L.-J. et al. (Feb. 2004). "Prevention of Obesity and Insulin Resistance in Mice Lacking Plasminogen Activator Inhibitor 1," Diabetes 53:336-346.

Miles, L.A. et al. (Nov. 11, 2016). "Abstract 19088 the Plasminogen Receptor, Plg-Rkt, Regulates Metabolic Homeostasis and Promotes Healthy Adipose Function," Circulation 134(Suppl 1), 2 pages.

Mirsky, A.I. et al. (1958). "The Destruction Of Glucagon, Adrenocorticotropin and Somatotropin By Human Blood Plasma," J. Clin. Invest. 28:14-20.

NCBI Reference Sequence—NP_000292.1 (May 4, 2019). "Plasminogen Isoform 1 Precursor [*Homo sapiens*]," 4 pages.

Schott, D. et al. (Dec. 3, 1998). "Therapy With A Purified Plasminogen Concentrate In An Infant With Ligneous Conjunctivitis And Homozygous Plasminogen Deficiency," The New England Journal of Medicine 339(23):1679-1686.

Siconolfi, L.B. et al. (Jun. 15, 2001). "Mice Lacking tPA, uPA, or Plasminogen Genes Showed Delayed Functional Recovery after Sciatic Nerve Crush, "J Neurosci, 21(12):4348-4355.

Sima, J. et al. (Apr. 23, 2004, e-pub. Mar. 23, 2004). "The Effect Of Angiostatin On Vascular Leakage and VEGF Expression In Rat Retina," FEBS Letters 564(1-2):19-23.

Wang, Q. (Sep. 2005). "Rest and Protection Of Pancreatic Islet Beta-Cell," Chinese Nursing Research 19 (9A): 1706-1708. * English Abstract.

Zhou, H. et al. (Aug. 2011). "Treatment of 62 Cases of Type 2 Diabetes With Plasmin," 30(Suppl):35-36. * English Abstract.

Zou, T. et al. (Jan. 2006). "Exogenous Tissue Plasminogen Activator Enhances Peripheral Nerve Regeneration and Functional Recovery After Injury In Mice," J. Neuropathol. Exp. Neurol. 65(1):78-86.

Aisina, R.B. et al. (2014). "Structure and Function of Plasminogen/Plasmin System," Russian Journal of Bioorganic Chemistry 40(6):590-604.

Gao, G. et al. (Apr. 2002). "Difference in Ischemic Regulation of Vascular Endothelial Growth Factor and Pigment Epithelium-Derived Factor in Brown Norway and Sprague Dawley Rats Contributing to Difference Susceptibilities to Retinal Neovascularization," Diabetes 51:1218-1225.

Hou, X. (Dec. 31, 2012), "Effect Of Type 2 Diabetes Insulin Pump Therapy On Glucose And Lipid Metabolism and Plasminogen," Journal Of Heze Medical College 24(1):21-22. English Abstract.

Liu, C. et al. (Jul. 31, 2012). "Comparision Of The Affect Of Gumepiride and Metformin On Fibrinolytic Function In Patients With Newly Diagnosed Type 2 Diabetes Mellitus," Modem Hospital 12:8-9. English Abstract.

Polat, S.B. et al. (Dec. 31, 2014). "Evaluation of Serum Fibrinogen, Plasminogen, α2-Anti-Plasmin, and Plasminogen Activator Inhibitor Levels (PAI) and Their Correlation with Presence of Retinopathy in Patients with Type 1 DM," Journal of Diabetes Research 2014(317292):1-6.

Yan, X.-F. et al, (Nov. 30, 2013). "Beta Ceil Function In Relation To Plasminogen Activator Inhibitor-1 and Tissue-Plasminogen Activator In Postmenopausal Females With Different Glucose Tolerance," Chin J Hypertens 21 (11):1045-1048. English Abstract.

Zhang, Y. et. al, (Mar. 20, 2008). "Relationship Between Fibrinolysis Change and Insulin Resistance In Type 2 Diabetes Mellitus With Microangiopathy," Clinical Focus, 23(6):397-399. English Abstract.

Zhao, Y. et al. (Dec. 31, 2007). "Clinical Observation Of Plasmin In The Treatment Of 36 Cases Of Progressive Cerebral Infarction," Journal Of North Sichuan Medical College, 22(6):549-550. English Abstract.

Extended European Search Report, dated Aug. 7, 2020, for European Patent Application No. 17880561.0, 8 pages.

Fu, Z. et al. (Dec. 4, 2002). "Effects of Plasmin Capsules on Antioxidation and Endothelial Function in Patients With High Altitude Polycythemia," The 41st Hospital of PLA pp. 33-35. English Abstract.

Li, J. et al. (Mar. 2005). "The Plasminogen Activator/Plasmin System is Essential for Development of the Joint Inflammatory Phase of Collagen Type II-Induced Arthritis," American Journal of Pathology 166(3):783-792.

Pinkney, J.H. et al. (Sep. 1997). "Endothelial Dysfunction: Cause of the Insulin Resistance Syndrome," SciTech Premium Collection 46:S9-S13.

Robertson, R.P. et al. (2007, e-pub. Apr. 9, 2007). "Pancreatic Islet β-Cell and Oxidative Stress: The Importance of Glutathione Peroxidase," FEBS Letters 581:3743-3748.

Shaw, M.A. et al. (Apr. 5, 2017, e-pub. Mar. 8, 2017). "Plasminogen Deficiency Delays the Onset and Protects From Demyelination and Paralysis in Autoimmune Neuroinflammatory Disease," Journal of Neuroscience 37 (14):3776-3788.

(56) References Cited

OTHER PUBLICATIONS

Sun, Y. et al. (2010) "Advancement on Thrombolytic Characteristic, Function and Clinical Application of Different Fibrinolytic Enzyemes," China Journal of Chinese Materia Medica 35(6):794-798. English Abstract.

* cited by examiner

TREATMENT OF DIABETIC NERVE INJURY COMPRISING ADMINISTERING PLASMINOGEN

CROSS REFERENCE TO RELATED APPLICATIONS

This application is a National Phase application under 35 U.S.C. § 371 of International Application No. PCT/CN2016/110449, filed Dec. 16, 2016, which claims priority to International Application No. PCT/CN2015/097943, filed Dec. 18, 2015, each of which is incorporated herein by reference in its entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 794922000100SEQLIST.TXT, date recorded: Jun. 13, 2018, size: 46 KB).

TECHNICAL FIELD

The present invention relates to the effects of plasminogen or plasmin in the repair of nerve tissue injury and prevention and/or treatment of diabetic nerve injury-related disorders.

BACKGROUND ART

Diabetes mellitus is a chronic disease with disordered metabolisms of carbohydrates, fats and proteins caused by relatively or absolutely insufficient insulin in the body or decreased sensitivity of target cells to insulin, or structural defects in insulin itself[1]. The annual cost for the treatment of diabetes mellitus in the United States is 176 billion dollars, and the indirect loss caused by diabetes mellitus is also as high as 69 billion dollars[2]. Diabetic neuropathy is a disease involving the metabolic disorders of the body characterized by diabetic hyperglycemia that affects the nervous system, and it is also one of the most common chronic complications of diabetes mellitus[3]. 60%-75% of diabetics eventually develop into diabetic neuropathy[4]. Diabetic neuropathy is the most important factor in non-traumatic lower limb amputation. Diabetic neuropathy mainly includes diabetic central neuropathy and diabetic peripheral neuropathy (DNP), especially the latter is more common. Diabetic central neuropathy refers to lesions caused by damage to neurons and nerve fibers in the cerebrum, cerebellum and brain stem, and neurons in the spinal cord in the context of diabetes mellitus. Diabetic peripheral neuropathy refers to the presence of symptoms and/or signs associated with peripheral neurological dysfunction in diabetics, excluding other causes, which are mainly caused by damage or infection of peripheral sensory nerves.

Pain is one of the main symptoms of diabetic neuropathy and is mainly caused by diabetic nerve injury. As mentioned above, diabetic neuropathic pain is correspondingly divided into diabetic central neuropathic pain and diabetic peripheral neuropathic pain. The latter is more common and seriously affects the quality of life of patients, in particular, impairs sleep and reduces life enjoyment. Long-term chronic pain symptoms alter the mental, emotional and other aspects of patients, and reduce their ability to live and socialize at the same time.

For diabetic neuropathy, the specific pathogenesis of pain at different stages has not been fully understood yet. Currently, clinically used drugs for the treatment of diabetic neuropathic pain mainly include the following categories: (1) antiepileptic drugs, such as gabapentin and pregabalin; (2) opioid analgesics, such as tramadol, morphines, and oxycodone; (3) local anesthetic drugs, such as lidocaine; (4) antidepressants, such as amitriptyline, paroxetine, and venlafaxine; and (5) non-steroidal anti-inflammatory drugs (NSAIDs), such as naproxen and nambumetone. However, traditional drugs still have many defects. For example, gabapentin and other antiepileptic drugs have a high incidence of side effects and adverse reactions and are expensive; opioids and non-steroidal anti-inflammatory drugs have limited or insufficient efficacy on peripheral and central neuropathic pains; paroxetine, venlafaxine and other antidepressants are prone to leading to central serotonin syndrome and have many medication taboos; and so on. Therefore, although there has been some progress in the development of drugs for relieving diabetic neuropathic pain in recent years, there is still an urgent need for an effective drug for repairing diabetic nerve injury and preventing diabetic nerve injury-related disorders.

Plasmin is a key component of the plasminogen activation system (PA system). It is a broad-spectrum protease that is capable of hydrolyzing several components of the extracellular matrix (ECM), including fibrin, gelatin, fibronectin, laminin, and proteoglycan[5]. In addition, plasmin can activate some pro-metalloproteinases (pro-MMPs) to form active metalloproteinases (MMPs). Therefore, plasmin is considered to be an important upstream regulator of extracellular proteolysis[6,7]. Plasmin is formed by the proteolysis of plasminogen by two physiological PAs: tissue plasminogen activator (tPA) or urokinase-type plasminogen activator (uPA). Due to the relatively high level of plasminogen in plasma and other body fluids, it is traditionally believed that the regulation of the PA system is primarily achieved through the levels of PA synthesis and activity. The synthesis of PA system components is strictly regulated by different factors, such as hormones, growth factors and cytokines. In addition, there are also specific physiological inhibitors of plasmin and PAs. The main inhibitor of plasmin is α2-antiplasmin. There are uPA-specific cell surface receptors (uPARs) that have direct hydrolytic activity on certain cell surfaces[8,9].

Plasminogen (plg) is a single-stranded glycoprotein composed of 791 amino acids and has a molecular weight of about 92 kDa[10,11]. Plasminogen is mainly synthesized in the liver and is abundantly present in the extracellular fluid. The content of plasminogen in plasma is about 2 μM. Therefore, plasminogen is a huge potential source of proteolytic activity in tissues and body fluids[12,13]. Plasminogen exists in two molecular forms: glutamic acid-plasminogen (Glu-plasminogen) and lysine-plasminogen (Lys-plasminogen). The naturally secreted and uncleaved forms of plasminogen have an amino-terminal (N-terminal) glutamic acid and are therefore referred to as glutamic acid-plasminogen. However, in the presence of plasmin, glutamic acid-plasminogen is hydrolyzed to lysine-plasminogen at Lys76-Lys77. Compared with glutamic acid-plasminogen, lysine-plasminogen has a higher affinity for fibrin and can be activated by PAs at a higher rate. The Arg560-Val561 peptide bond of these two forms of plasminogen can be cleaved by uPA or tPA, resulting in the formation of plasmin as a disulfide-linked double-strand protease[14]. The amino-terminal portion of plasminogen contains five homotrimeric rings, i.e., the so-called kringles, and the carboxy-terminal portion contains a protease domain. Some kringles contain lysine-binding sites that mediate the specific interaction of plasminogen with fibrin and its inhibitor α2-AP. A newly discovered 38 kDa fragment of plasminogen, comprising kringles 1-4, is a potent inhibitor of angiogenesis. This fragment is named as angiostatin and can be produced by proteolysis of plasminogen by several proteases.

The main substrate of plasmin is fibrin, and the dissolution of fibrin is the key to prevent pathological thrombosis[15]. Plasmin also has substrate specificity for several components of ECM, including laminin, fibronectin, proteoglycan and gelatin, indicating that plasmin also plays an important role in ECM remodeling[12,16,17]. Indirectly, plasmin can also degrade other components of ECM by converting certain protease precursors into active proteases, including MMP-1, MMP-2, MMP-3 and MMP-9. Therefore, it has been proposed that plasmin may be an important upstream regulator of extracellular proteolysis[18]. In addition, plasmin has the ability to activate certain potential forms of growth factors[19-21] In vitro, plasmin can also hydrolyze components of the complement system and release chemotactic complement fragments.

The db/db mouse is one of the most widely used experimental animal models of diabetes mellitus. It is highly similar to humans in terms of the pathogenetic process, pathogenesis, etc. of diabetic neuralgia. Therefore, db/db mice are used for related studies, and the results are representative. The db/db mice develop into diabetic mice at 4-6 weeks, have hyperalgesia at 8-12 weeks, and have hypoalgesia after 12 weeks.[22-26]

Through research, the present inventors have surprisingly found that plasminogen has significant effects in nerve repair and in the treatment of diabetic nerve injury and its related disorders, and has good safety. Therefore, plasminogen may be a new strategy for repairing diabetic nerve tissue injury and treating and/or preventing its related disorders.

SUMMARY OF THE INVENTION

In one aspect, the present invention relates to a method for preventing and/or repairing diabetic nerve injury, comprising administering a therapeutically effective amount of plasminogen or plasmin to a subject. In one aspect, the present invention relates to the use of plasminogen or plasmin for preventing and/or repairing diabetic nerve injury, comprising administering a therapeutically effective amount of plasminogen or plasmin to a subject.

In one embodiment, the diabetic nerve injury includes nerve tissue injury and neuroinflammation. The present invention also relates to a method for treating and/or preventing a diabetic nerve injury-related disorder, comprising administering a therapeutically effective amount of plasminogen or plasmin to a subject. In one embodiment, the diabetic nerve injury-related disorder includes limb pain, hypoesthesia, numbness, burning, coldness and diabetic neuropathic pain, including, but not limited to, spontaneous pain, hypoalgesia, hyperalgesia, etc. induced by diabetic complications. In one embodiment, the plasminogen has at least 80%, 85%, 90%, 95%, 96%, 97%, 98% or 99% sequence identity with SEQ ID No. 2, 6, 8, 10 or 12, and still has the activity of plasminogen. In one embodiment, the plasminogen is a protein that comprises a plasminogen active fragment and still has the activity of plasminogen. In one embodiment, the plasminogen is selected from Glu-plasminogen, Lys-plasminogen, mini-plasminogen, micro-plasminogen, δ-plasminogen or any combination thereof. In one embodiment, the plasminogen is administered systemically or locally, for example, by topical, intravenous, intramuscular, subcutaneous, inhalation, intraspinal, local injection, intraarticular injection or rectal administration. In one embodiment, the plasminogen can be administered in combination with other drugs or therapies. In one embodiment, the other drugs or therapies include neurotrophic drugs, analgesics, drugs for the treatment of diabetes mellitus, anti-infective drugs, anti-hypertensive drugs, anti-hyperlipidemic drugs, and physical therapies such as electromagnetic therapy and infrared therapy.

In one embodiment, the subject is a mammal, preferably human.

In one embodiment, the subject has a low level of plasmin or plasminogen. Specifically, the low level is innate, secondary and/or local.

In one embodiment, the plasminogen has at least 80%, 85%, 90%, 95%, 96%, 97%, 98% or 99% sequence identity with SEQ ID No. 2, 6, 8, 10 or 12, and still has the activity of plasminogen. In one embodiment, the plasminogen is a protein that has 1-100, 1-90, 1-80, 1-70, 1-60, 1-50, 1-45, 1-40, 1-35, 1-30, 1-25, 1-20, 1-15, 1-10, 1-5, 1-4, 1-3, 1-2 or 1 amino acid added, deleted and/or substituted in SEQ ID No.2, 6, 8, 10 or 12, and still has the activity of plasminogen. In one embodiment, the plasminogen is a protein that comprises a plasminogen active fragment and still has the activity of plasminogen. In one embodiment, the plasminogen is selected from Glu-plasminogen, Lys-plasminogen, mini-plasminogen, micro-plasminogen, δ-plasminogen or any combination thereof. In one embodiment, the plasminogen is a conservatively substituted variant selected from the variants of Glu-plasminogen, Lys-plasminogen, mini-plasminogen, δ-plasminogen or micro-plasminogen. In one embodiment, the plasminogen is a human natural plasminogen, such as an ortholog of plasminogen shown in SEQ ID No.2, e.g., an ortholog of plasminogen from primates or rodents, for example, an ortholog of plasminogen from gorillas, rhesus monkeys, murine, cows, horses and dogs. Most preferably, the amino acid sequence of the plasminogen of the present invention is as shown in SEQ ID No.2, 6, 8, 10 or 12.

In one embodiment, the plasminogen is administered in combination with a suitable polypeptide carrier or stabilizer. In one embodiment, the plasminogen is administered at a dosage of 0.0001-2000 mg/kg, 0.001-800 mg/kg, 0.01-600 mg/kg, 0.1-400 mg/kg, 1-200 mg/kg, 1-100 mg/kg or 10-100 mg/kg (by per kg of body weight) or 0.0001-2000 mg/cm$^2$, 0.001-800 mg/cm$^2$, 0.01-600 mg/cm$^2$, 0.1-400 mg/cm$^2$, 1-200 mg/cm$^2$, 1-100 mg/cm$^2$ or 10-100 mg/cm$^2$ (by per square centimeter of body surface area) daily, preferably the dosage is repeated at least once, preferably the dosage is administered at least daily. In the case of local administration, the above dosages may also be further adjusted depending on the circumstances.

In another aspect, the present invention relates to the use of plasminogen or plasmin in the manufacture of a medicament for preventing and/or repairing diabetic nerve injury. In one aspect, the present invention relates to a method for manufacturing a medicament, comprising preparing a medicament for preventing and/or repairing diabetic nerve injury using plasminogen or plasmin together with a pharmaceutically acceptable carrier.

In one embodiment, the diabetic nerve injury includes nerve tissue injury and neuroinflammation. The present invention also relates to the use of plasminogen or plasmin in the manufacture of a medicament for treating and/or preventing a diabetic nerve injury-related disorder. In one embodiment, the diabetic nerve injury-related disorder includes limb pain, hypoesthesia, numbness, burning, coldness and diabetic neuropathic pain, including, but not limited to, spontaneous pain, hypoalgesia and hyperalgesia induced by diabetic complications. In one embodiment, the plasminogen has at least 80%, 85%, 90%, 95%, 96%, 97%, 98% or 99% sequence identity with SEQ ID No. 2, 6, 8, 10 or 12, and still has the activity of plasminogen. In one embodiment, the plasminogen is a protein that comprises a plasminogen active fragment and still has the activity of plasminogen. In one embodiment, the plasminogen is selected from Glu-plasminogen, Lys-plasminogen, mini-plasminogen, micro-plasminogen, δ-plasminogen or any combination thereof. In one embodiment, the plasminogen is administered systemically or locally, for example, by topical, intravenous, intramuscular, subcutaneous, inhalation, intraspinal, local injection, intraarticular injection or rectal administration. In one embodiment, the plasminogen can be administered in combination with other drugs or therapies. In one embodiment, the other drugs or therapies include neurotrophic drugs, analgesics, drugs for the treatment of diabetes mellitus, anti-infective drugs, anti-hypertensive drugs, anti-hyperlipidemic drugs, and physical therapies such as electromagnetic therapy and infrared therapy.

In one embodiment, the subject is a mammal, preferably human.

In one embodiment, the subject has a low level of plasmin or plasminogen. Specifically, the low level is innate, secondary and/or local.

In one embodiment, the plasminogen has at least 80%, 85%, 90%, 95%, 96%, 97%, 98% or 99% sequence identity with SEQ ID No. 2, 6, 8, 10 or 12, and still has the activity of plasminogen. In one embodiment, the plasminogen is a protein that has 1-100, 1-90, 1-80, 1-70, 1-60, 1-50, 1-45, 1-40, 1-35, 1-30, 1-25, 1-20, 1-15, 1-10, 1-5, 1-4, 1-3, 1-2 or 1 amino acid added, deleted and/or substituted in SEQ ID No.2, 6, 8, 10 or 12, and still has the activity of plasminogen. In one embodiment, the plasminogen is a protein that comprises a plasminogen active fragment and still has the activity of plasminogen. In one embodiment, the plasminogen is selected from Glu-plasminogen, Lys-plasminogen, mini-plasminogen, micro-plasminogen, δ-plasminogen or any combination thereof. In one embodiment, the plasminogen is a conservatively substituted variant selected from the variants of Glu-plasminogen, Lys-plasminogen, mini-plasminogen, δ-plasminogen or micro-plasminogen. In one embodiment, the plasminogen is a human natural plasminogen, such as an ortholog of plasminogen shown in SEQ ID No.2, e.g., an ortholog of plasminogen from primates or rodents, for example, an ortholog of plasminogen from gorillas, rhesus monkeys, murine, cows, horses and dogs. Most preferably, the amino acid sequence of the plasminogen of the present invention is as shown in SEQ ID No.2, 6, 8, 10 or 12.

In one embodiment, the plasminogen is administered in combination with a suitable polypeptide carrier or stabilizer. In one embodiment, the plasminogen is administered at a dosage of 0.0001-2000 mg/kg, 0.001-800 mg/kg, 0.01-600 mg/kg, 0.1-400 mg/kg, 1-200 mg/kg, 1-100 mg/kg or 10-100 mg/kg (by per kg of body weight) or 0.0001-2000 mg/cm$^2$, 0.001-800 mg/cm$^2$, 0.01-600 mg/cm$^2$, 0.1-400 mg/cm$^2$, 1-200 mg/cm$^2$, 1-100 mg/cm$^2$ or 10-100 mg/cm$^2$ (by per square centimeter of body surface area) daily, preferably the dosage is repeated at least once, preferably the dosage is administered at least daily. In the case of local administration, the above dosages may also be further adjusted depending on the circumstances.

In another aspect, the present invention relates to plasminogen for preventing and/or repairing diabetic nerve injury in a subject, as well as a pharmaceutical composition which comprises plasminogen or plasmin and is useful in the prevention and/or repair of diabetic nerve injury in a subject. In one embodiment, the diabetic nerve injury includes nerve tissue injury and neuroinflammation. The present invention also relates to plasminogen for treating and/or preventing a diabetic nerve injury-related disorder in a subject, as well as a pharmaceutical composition which comprises plasminogen and is useful in the treatment and/or prevention of a diabetic nerve injury-related disorder in a subject. In one embodiment, the diabetic nerve injury-related disorder includes limb pain, hypoesthesia, numbness, burning, coldness and diabetic neuropathic pain, including, but not limited to, spontaneous pain, hypoalgesia and hyperalgesia induced by diabetic complications. In one embodiment, the plasminogen has at least 80%, 85%, 90%, 95%, 96%, 97%, 98% or 99% sequence identity with SEQ ID No. 2, 6, 8, 10 or 12, and still has the activity of plasminogen. In one embodiment, the plasminogen is a protein that comprises a plasminogen active fragment and still has the activity of plasminogen. In one embodiment, the plasminogen is selected from Glu-plasminogen, Lys-plasminogen, mini-plasminogen, micro-plasminogen, δ-plasminogen or any combination thereof. In one embodiment, the plasminogen is administered systemically or locally, for example, by topical, intravenous, intramuscular, subcutaneous, inhalation, intraspinal, local injection, intraarticular injection or rectal administration. In one embodiment, the plasminogen can be administered in combination with other drugs or therapies. In one embodiment, the other drugs or therapies include neurotrophic drugs, analgesics, drugs for the treatment of diabetes mellitus, anti-infective drugs, anti-hypertensive drugs, anti-hyperlipidemic drugs, and physical therapies such as electromagnetic therapy and infrared therapy.

In one embodiment, the subject is a mammal, preferably human.

In one embodiment, the subject has a low level of plasmin or plasminogen. Specifically, the low level is innate, secondary and/or local.

In one embodiment, the plasminogen has at least 80%, 85%, 90%, 95%, 96%, 97%, 98% or 99% sequence identity with SEQ ID No. 2, 6, 8, 10 or 12, and still has the activity of plasminogen. In one embodiment, the plasminogen is a protein that has 1-100, 1-90, 1-80, 1-70, 1-60, 1-50, 1-45, 1-40, 1-35, 1-30, 1-25, 1-20, 1-15, 1-10, 1-5, 1-4, 1-3, 1-2 or 1 amino acid added, deleted and/or substituted in SEQ ID No.2, 6, 8, 10 or 12, and still has the activity of plasminogen. In one embodiment, the plasminogen is a protein that comprises a plasminogen active fragment and still has the activity of plasminogen. In one embodiment, the plasminogen is selected from Glu-plasminogen, Lys-plasminogen, mini-plasminogen, micro-plasminogen, δ-plasminogen or any combination thereof. In one embodiment, the plasminogen is a conservatively substituted variant selected from the variants of Glu-plasminogen, Lys-plasminogen, mini-plasminogen, δ-plasminogen or micro-plasminogen. In one embodiment, the plasminogen is a human natural plasminogen, such as an ortholog of plasminogen shown in SEQ ID No.2, e.g., an ortholog of plasminogen from primates or rodents, for example, an ortholog of plasminogen from gorillas, rhesus monkeys, murine, cows, horses and dogs. Most preferably, the amino acid sequence of the plasminogen of the present invention is as shown in SEQ ID No.2, 6, 8, 10 or 12.

In one embodiment, the plasminogen is administered in combination with a suitable polypeptide carrier or stabilizer. In one embodiment, the plasminogen is administered at a dosage of 0.0001-2000 mg/kg, 0.001-800 mg/kg, 0.01-600 mg/kg, 0.1-400 mg/kg, 1-200 mg/kg, 1-100 mg/kg or 10-100 mg/kg (by per kg of body weight) or 0.0001-2000 mg/cm$^2$, 0.001-800 mg/cm$^2$, 0.01-600 mg/cm$^2$, 0.1-400 mg/cm$^2$, 1-200 mg/cm$^2$, 1-100 mg/cm$^2$ or 10-100 mg/cm$^2$ (by per square centimeter of body surface area) daily, preferably the dosage is repeated at least once, preferably the dosage is administered at least daily. In the case of local administration, the above dosages may also be further adjusted depending on the circumstances.

In another aspect, the present invention relates to an article of manufacture or a kit of a pharmaceutical composition which comprises plasminogen or plasmin and is useful in the prevention and/or repair of diabetic nerve injury in a subject. In one embodiment, the diabetic nerve injury includes nerve tissue injury and neuroinflammation. The present invention also relates to an article of manufacture or a kit of a pharmaceutical composition which comprises plasminogen or plasmin and is useful in the treatment and/or prevention of a diabetic nerve injury-related disorder in a subject. In one embodiment, the diabetic nerve injury-related disorder includes limb pain, hypoesthesia, numbness, burning, coldness and diabetic neuropathic pain, including, but not limited to, spontaneous pain, hypoalgesia and hyperalgesia induced by diabetic complications. In one embodiment, the plasminogen has at least 80%, 85%, 90%, 95%, 96%, 97%, 98% or 99% sequence identity with SEQ ID No. 2, 6, 8, 10 or 12, and still has the activity of plasminogen. In one embodiment, the plasminogen is a protein that comprises a plasminogen active fragment and still has the activity of plasminogen. In one embodiment, the plasminogen is selected from Glu-plasminogen, Lys-plasminogen, mini-plasminogen, micro-plasminogen, δ-plasminogen or any combination thereof. In one embodiment, the plasminogen is administered systemically or locally, for example, by topical, intravenous, intramuscular, subcutaneous, inhalation, intraspinal, local injection, intraarticular injection or rectal administration. In one embodiment, the plasminogen can be administered in combination with other drugs or therapies. In one embodiment, the other drugs or therapies include neurotrophic drugs, analgesics, drugs for the treatment of diabetes mellitus, anti-infective drugs, anti-hypertensive drugs, anti-hyperlipidemic drugs, and physical therapies such as electromagnetic therapy and infrared therapy.

In one embodiment, the subject is a mammal, preferably human.

In one embodiment, the subject has a low level of plasmin or plasminogen. Specifically, the low level is innate, secondary and/or local.

In one embodiment, the plasminogen has at least 80%, 85%, 90%, 95%, 96%, 97%, 98% or 99% sequence identity with SEQ ID No. 2, 6, 8, 10 or 12, and still has the activity of plasminogen. In one embodiment, the plasminogen is a protein that has 1-100, 1-90, 1-80, 1-70, 1-60, 1-50, 1-45, 1-40, 1-35, 1-30, 1-25, 1-20, 1-15, 1-10, 1-5, 1-4, 1-3, 1-2 or 1 amino acid added, deleted and/or substituted in SEQ ID No.2, 6, 8, 10 or 12, and still has the activity of plasminogen. In one embodiment, the plasminogen is a protein that comprises a plasminogen active fragment and still has the activity of plasminogen. In one embodiment, the plasminogen is selected from Glu-plasminogen, Lys-plasminogen, mini-plasminogen, micro-plasminogen, δ-plasminogen or any combination thereof. In one embodiment, the plasminogen is a conservatively substituted variant selected from the variants of Glu-plasminogen, Lys-plasminogen, mini-plasminogen, δ-plasminogen or micro-plasminogen. In one embodiment, the plasminogen is a human natural plasminogen, such as an ortholog of plasminogen shown in SEQ ID No.2, e.g., an ortholog of plasminogen from primates or rodents, for example, an ortholog of plasminogen from gorillas, rhesus monkeys, murine, cows, horses and dogs. Most preferably, the amino acid sequence of the plasminogen of the present invention is as shown in SEQ ID No.2, 6, 8, 10 or 12.

In one embodiment, the article of manufacture or kit comprises a container containing an effective dosage of plasminogen. Preferably, the article of manufacture or kit further comprises a container containing one or more other drugs. The kit can also comprise instructions for use, which indicate that the plasminogen can be used to treat the nerve injury caused by diabetes mellitus and nerve injury-related disorders, and can further indicate that the plasminogen can be administered before, simultaneously with and/or after administration of other drugs or therapies.

In one aspect, the present invention relates to the use of plasminogen or plasmin in the manufacture of a medicament, article of manufacture or kit for preventing and/or treating injury (damage) to body tissues and internal organs caused by diabetic angiopathy in a subject. In one embodiment, the injury (damage) to tissues and internal organs includes injury (damage) to the brain, heart, liver, lungs, kidneys, nerves, retina, skin and gastrointestinal tract. In one aspect, the present invention relates to the use of plasminogen or plasmin in the manufacture of a medicament, article of manufacture or kit for preventing and/or treating a diabetic complication in a subject. In one embodiment, the diabetic complication is diabetic encephalopathy, diabetic cardiopathy, diabetic hepatopathy, diabetic nephropathy, diabetic pneumonopathy, diabetic neuropathy, diabetic angiopathy, diabetic retinopathy or diabetic dermopathy induced by diabetes mellitus.

In one aspect, the present invention relates to a method for manufacturing a medicament, comprising preparing a medicament, article of manufacture or kit for preventing and/or treating injury (damage) to body tissues and internal organs caused by diabetic angiopathy in a subject using plasminogen or plasmin and a pharmaceutically acceptable carrier. In one embodiment, the injury (damage) to tissues and internal organs includes injury (damage) to the brain, heart, liver, lungs, kidneys, nerves, retina, skin and gastrointestinal tract. In one aspect, the present invention relates to a method for manufacturing a medicament, comprising preparing a medicament, article of manufacture or kit for preventing and/or treating a diabetic complication in a subject using plasminogen or plasmin and a pharmaceutically acceptable carrier. In one embodiment, the diabetic complication is diabetic encephalopathy, diabetic cardiopathy, diabetic hepatopathy, diabetic nephropathy, diabetic pneumonopathy, diabetic neuropathy, diabetic angiopathy, diabetic retinopathy or diabetic dermopathy induced by diabetes mellitus.

In one aspect, the present invention relates to plasminogen or plasmin, and a pharmaceutical composition, article of manufacture or kit comprising the plasminogen or plasmin, which are useful in the prevention and/or treatment of injury (damage) to body tissues and internal organs caused by diabetic angiopathy in a subject. In one embodiment, the injury (damage) to tissues and internal organs includes injury (damage) to the brain, heart, liver, kidneys, lungs, nerves, retina, gastrointestinal tract and skin. In one aspect, the present invention relates to plasminogen, and a pharmaceutical composition, article of manufacture or kit comprising the plasminogen, which are useful in the prevention and/or treatment of a diabetic complication in a subject. In one embodiment, the diabetic complication is diabetic encephalopathy, diabetic cardiopathy, diabetic hepatopathy, diabetic pneumonopathy, diabetic nephropathy, diabetic neuropathy, diabetic angiopathy, diabetic retinopathy or diabetic dermopathy induced by diabetes mellitus.

In one aspect, the present invention relates to a method for preventing and/or treating injury (damage) to body tissues and internal organs caused by diabetic angiopathy in a subject, comprising administering plasminogen or plasmin or a pharmaceutical composition, article of manufacture or kit comprising the plasminogen or plasmin to the subject. The present invention also relates to the use of plasminogen or plasmin, or a pharmaceutical composition, article of manufacture or kit comprising the plasminogen or plasmin for preventing and/or treating injury (damage) to body tissues and internal organs caused by diabetic angiopathy in a subject. In one embodiment, the injury (damage) to tissues and internal organs includes injury (damage) to the brain, heart, liver, lungs, kidneys, nerves, retina, gastrointestinal tract and skin. In one aspect, the present invention relates to a method for preventing and/or treating a diabetic complication in a subject, comprising administering plasminogen or plasmin, or a pharmaceutical composition, article of manufacture or kit comprising the plasminogen or plasmin to the subject. The present invention also includes the use of plasminogen or plasmin, or a pharmaceutical composition, article of manufacture or kit comprising the plasminogen or plasmin for preventing and/or treating a diabetic complication in a subject. In one embodiment, the diabetic complication is diabetic encephalopathy, diabetic cardiopathy, diabetic hepatopathy, diabetic pneumonopathy, diabetic nephropathy, diabetic neuropathy, diabetic angiopathy, diabetic retinopathy or diabetic dermopathy induced by diabetes mellitus.

In one embodiment, the plasminogen has at least 80%, 85%, 90%, 95%, 96%, 97%, 98% or 99% sequence identity with SEQ ID No. 2, 6, 8, 10 or 12, and still has the activity of plasminogen. In one embodiment, the plasminogen is a protein that has 1-100, 1-90, 1-80, 1-70, 1-60, 1-50, 1-45, 1-40, 1-35, 1-30, 1-25, 1-20, 1-15, 1-10, 1-5, 1-4, 1-3, 1-2 or 1 amino acid added, deleted and/or substituted in SEQ ID No.2, 6, 8, 10 or 12, and still has the activity of plasminogen. In one embodiment, the plasminogen is a protein that comprises a plasminogen active fragment and still has the activity of plasminogen. In one embodiment, the plasminogen is selected from Glu-plasminogen, Lys-plasminogen, mini-plasminogen, micro-plasminogen, δ-plasminogen or any combination thereof. In one embodiment, the plasminogen is a conservatively substituted variant selected from the variants of Glu-plasminogen, Lys-plasminogen, mini-plasminogen, δ-plasminogen or micro-plasminogen. In one embodiment, the plasminogen is a human natural plasminogen, such as an ortholog of plasminogen shown in SEQ ID No.2, e.g., an ortholog of plasminogen from primates or rodents, for example, an ortholog of plasminogen from gorillas, rhesus monkeys, murine, cows, horses and dogs. Most preferably, the amino acid sequence of the plasminogen of the present invention is as shown in SEQ ID No.2, 6, 8, 10 or 12.

In one embodiment, the subject has a low level of plasmin or plasminogen. Specifically, the low level is innate, secondary and/or local.

The present invention explicitly encompasses all the combinations of technical features belonging to the embodiments of the present invention, and these combined technical solutions have been explicitly disclosed in the present application, as if the above technical solutions were individually and explicitly disclosed. In addition, the present invention also explicitly encompasses all the subcombinations of the various embodiments and elements thereof, and these subcombinations have been disclosed herein, as if each of such subcombinations was individually and explicitly disclosed herein.

DETAILED DESCRIPTION OF EMBODIMENTS

1. Definition

"Diabetes mellitus" is a series of dysmetabolic syndromes of carbohydrates, proteins, fats, water, electrolytes and the like that are caused by islet hypofunction, insulin resistance and the like resulting from the effects of genetic factors, immune dysfunction, microbial infections and toxins thereof, free radical toxins, mental factors and other various pathogenic factors on the body, and is mainly characterized by hyperglycemia clinically.

"Diabetic complications" are damages to or dysfunctions of other organs or tissues of the body caused by poor blood glucose control during diabetes mellitus, including damages to or dysfunctions of the liver, kidneys, heart, retina, nervous system damage and the like. According to statistics of the World Health Organization, there are up to more than 100 diabetic complications, and diabetes mellitus is a disease currently known to have the most complications.

"Diabetic microangiopathy" refers to microangiopathy caused by varying degrees of abnormalities in the microcirculation of various body organs or tissues of diabetics. The process of microangiopathy formation roughly comprises functional changes in microcirculation, endothelial injury, thickening of the basement membrane, increased blood viscosity, aggregation of red blood cells, and adhesion and aggregation of platelets, eventually leading to microthrombosis and/or microvascular occlusion.

The above-mentioned "diabetic microangiopathy" causes local vascular injury to tissues or organs, poor blood flow, hypoxia of cells, and formation of blood clots, thrombi and inflammation, and further affects the functions of peripheral tissues and organs, thereby causing "diabetic complications". Therefore, when mentioned in the technical solutions claimed in the present invention, the terms "diabetic angiopathy" and "diabetic complications" both cover the thrombus induced by diabetes mellitus.

"Diabetic neuropathy" (or referred to as "diabetic nervous disease") is a disease involving the metabolic disorders of the body characterized by diabetic hyperglycemia that affects the nervous system, and is caused by the nervous system injury resulting from diabetes mellitus.

"Diabetic nerve injury" includes sensory nerve impairment, motor nerve impairment and autonomic nerve impairment. Of these, sensory nerve impairment is usually severer. A common symptom is pain, including burning-like pain, electric shock-like pain, needle punching-like pain, other various patient experiences and the like.

"Diabetic nerve injury-related disorders" are a series of disorders involving the metabolic disorders of the body characterized by diabetic hyperglycemia that affects the nervous system, and are caused by nervous system injury resulting from diabetes mellitus, including, but not limited to: limb pain, hypoesthesia, numbness, burning, coldness and diabetic neuropathic pain, including, but not limited to, spontaneous pain, hypoalgesia, hyperalgesia, etc. induced by diabetic complications.

"Diabetic neuropathic pain" is the most common form of diabetic neuropathy, and is usually caused by impaired diabetic sensory nerves. The main pain is usually accompanied by loss of temperature and tactile sensation. The pain occurs mostly in the lower limbs, and it also occurs in the upper limbs and the trunk. The pain can be generally divided into peripheral and central neuropathic pain. Peripheral neuropathic pain is caused by injury to peripheral nerves, and central neuropathic pain is caused by injury to the central nervous system and/or spinal cord.

"Plasmin" is a very important enzyme that exists in the blood and can hydrolyze fibrin clots into fibrin degradation products and D-dimers.

"Plasminogen" is the zymogenic form of plasmin, and based on the sequence in the swiss prot and calculated from the amino acid sequence (SEQ ID No.4) of the natural human plasminogen containing a signal peptide, is a glycoprotein composed of 810 amino acids, which has a molecular weight of about 90 kD and is synthesized mainly in the liver and capable of circulating in the blood; and the cDNA sequence encoding this amino acid sequence is as shown in SEQ ID No.3. Full-length plasminogen contains seven domains: a C-terminal serine protease domain, an N-terminal Pan Apple (PAp) domain and five Kringle domains (Kringles 1-5). Referring to the sequence in the swiss prot, the signal peptide comprises residues Met1-Gly19, PAp comprises residues Glu20-Val98, Kringle 1 comprises residues Cys103-Cys181, Kringle 2 comprises residues Glu184-Cys262, Kringle 3 comprises residues Cys275-Cys352, Kringle 4 comprises residues Cys377-Cys454, and Kringle 5 comprises residues Cys481-Cys560. According to the NCBI data, the serine protease domain comprises residues Val581-Arg804.

Glu-plasminogen is a natural full-length plasminogen and is composed of 791 amino acids (without a signal peptide of 19 amino acids); the cDNA sequence encoding this sequence is as shown in SEQ ID No.1; and the amino acid sequence is as shown in SEQ ID No.2. In vivo, Lys-plasminogen, which is formed by hydrolysis of amino acids at positions 76-77 of Glu-plasminogen, is also present, as shown in SEQ ID No.6; and the cDNA sequence encoding this amino acid sequence is as shown in SEQ ID No.5. δ-plasminogen is a fragment of full-length plasminogen that lacks the structure of Kringle 2-Kringle 5 and contains only Kringle 1 and the serine protease domain[27,30]. The amino acid sequence (SEQ ID No.8) of δ-plasminogen has been reported in the literature[30], and the cDNA sequence encoding this amino acid sequence is as shown in SEQ ID No.7. Mini-plasminogen is composed of Kringle 5 and the serine protease domain, and has been reported in the literature to comprise residues Val443-Asn791 (with the Glu residue of the Glu-plasminogen sequence that does not contain a signal peptide as the starting amino acid)[28]; the amino acid sequence is as shown in SEQ ID No.10; and the cDNA sequence encoding this amino acid sequence is as shown in SEQ ID No.9. Micro-plasminogen comprises only the serine protease domain, the amino acid sequence of which has been reported in the literature to comprise residues Ala543-Asn791 (with the Glu residue of the Glu-plasminogen sequence that does not contain a signal peptide as the starting amino acid)[29], and the sequence of which has been also reported in patent document CN 102154253 A to comprise residues Lys531-Asn791 (with the Glu residue of the Glu-plasminogen sequence that does not contain a signal peptide as the starting amino acid) (the sequence in this patent application refers to the patent document CN 102154253 A); the amino acid sequence is as shown in SEQ ID No. 12; and the cDNA sequence encoding this amino acid sequence is as shown in SEQ ID No.11.

In the present invention, "plasmin" is used interchangeably with "fibrinolysin" and "fibrinoclase", and the terms have the same meaning; and "plasminogen" is used interchangeably with "fibrinolytic zymogen" and "fibrinoclase zymogen", and the terms have the same meaning.

In the course of circulation, plasminogen is in a closed, inactive conformation, but when bound to thrombi or cell surfaces, it is converted into an active plasmin in an open conformation under the mediation of a plasminogen activator (PA). The active plasmin cn further hydrolyze the fibrin clots to fibrin degradation products and D-dimers, thereby dissolving the thrombi. The PAp domain of plasminogen comprises an important determinant that maintains plasminogen in an inactive, closed conformation, and the KR domain is capable of binding to lysine residues present on receptors and substrates. A variety of enzymes that can serve as plasminogen activators are known, including: tissue plasminogen activator (tPA), urokinase plasminogen activator (uPA), kallikrein, coagulation factor XII (Hagmann factor), and the like.

"Plasminogen active fragment" refers to an active fragment in the plasminogen protein that is capable of binding to a target sequence in a substrate and exerting the proteolytic function. The technical solutions of the present invention involving plasminogen encompass technical solutions in which plasminogen is replaced with a plasminogen active fragment. The plasminogen active fragment of the present invention is a protein comprising a serine protease domain of plasminogen. Preferably, the plasminogen active fragment of the present invention comprises SEQ ID NO: 14, or an amino acid sequence having an amino acid sequence identity of at least 80%, 90%, 95%, 96%, 97%, 98% or 99% with SEQ ID NO: 14. Therefore, plasminogen of the present invention comprises a protein containing the plasminogen active fragment and still having plasminogen activity.

At present, methods for determining plasminogen and its activity in blood include: detection of tissue plasminogen activator activity (t-PAA), detection of tissue plasminogen activator antigen (t-PAAg) in plasma, detection of tissue plasminogen activity (plgA) in plasma, detection of tissue plasminogen antigen (plgAg) in plasma, detection of activity of the inhibitor of tissue plasminogen activators in plasma, detection of inhibitor antigens of tissue plasminogen activators in plasma and detection of plasmin-anti-plasmin (PAP) complex in plasma. The most commonly used detection method is the chromogenic substrate method: streptokinase (SK) and a chromogenic substrate are added to a test plasma, the plasminogen in the test plasma is converted into PLM by the action of SK, PLM acts on the chromogenic substrate, and then it is determined that the increase in absorbance is directly proportional to plasminogen activity using a spectrophotometer. In addition, plasminogen activity in blood can also be determined by immunochemistry, gel electrophoresis, immunonephelometry, radioimmuno-diffusion and the like.

"Orthologues or orthologs" refer to homologs between different species, including both protein homologs and DNA homologs, and are also known as orthologous homologs and vertical homologs. The term specifically refers to proteins or genes that have evolved from the same ancestral gene in different species. The plasminogen of the present invention includes human natural plasminogen, and also includes orthologues or orthologs of plasminogens derived from different species and having plasminogen activity.

"Conservatively substituted variant" refers to one in which a given amino acid residue is changed without altering the overall conformation and function of the protein or enzyme, including, but not limited to, replacing an amino acid in the amino acid sequence of the parent protein by an amino acid with similar properties (such as acidity, alkalinity and hydrophobicity). Amino acids with similar properties are well known. For example, arginine, histidine and lysine are hydrophilic basic amino acids and are interchangeable. Similarly, isoleucine is a hydrophobic amino acid that can be replaced by leucine, methionine or valine. Therefore, the similarity of two proteins or amino acid sequences with similar functions may be different. For example, the similarity (identity) is 70%-99% based on the MEGALIGN algorithm. "Conservatively substituted variant" also includes a polypeptide or enzyme having amino acid identity of 60% or more, preferably 75% or more, more preferably 85% or more, even more preferably 90% or more as determined by the BLAST or FASTA algorithm, and having the same or substantially similar properties or functions as the natural or parent protein or enzyme.

"Isolated" plasminogen refers to the plasminogen protein that is isolated and/or recovered from its natural environment. In some embodiments, the plasminogen will be purified (1) to a purity of greater than 90%, greater than 95% or greater than 98% (by weight), as determined by the Lowly method, such as more than 99% (by weight); (2) to a degree sufficiently to obtain at least 15 residues of the N-terminal or internal amino acid sequence using a spinning cup sequenator; or (3) to homogeneity, which is determined by sodium dodecyl sulfate-polyacrylamide gel electrophoresis (SDS-PAGE) under reducing or non-reducing conditions using Coomassie blue or silver staining Isolated plasminogen also includes plasminogen prepared from recombinant cells by bioengineering techniques and separated by at least one purification step.

The terms "polypeptide", "peptide" and "protein" are used interchangeably herein and refer to polymeric forms of amino acids of any length, which may include genetically encoded and non-genetically encoded amino acids, chemically or biochemically modified or derivatized amino acids, and polypeptides having modified peptide backbones. The term includes fusion proteins, including, but not limited to, fusion proteins having heterologous amino acid sequences, fusions having heterologous and homologous leader sequences (with or without N-terminal methionine residues), and the like.

The "percent amino acid sequence identity (%)" with respect to the reference polypeptide sequence is defined as the percentage of amino acid residues in the candidate sequence identical to the amino acid residues in the reference polypeptide sequence when a gap is introduced as necessary to achieve maximal percent sequence identity and no conservative substitutions are considered as part of sequence identity. The comparison for purposes of determining percent amino acid sequence identity can be achieved in a variety of ways within the skill in the art, for example using publicly available computer softwares, such as BLAST, BLAST-2, ALIGN or Megalign (DNASTAR) software. Those skilled in the art can determine appropriate parameters for aligning sequences, including any algorithm needed to achieve the maximum comparison over the full length of the sequences being compared. However, for purposes of the present invention, the percent amino acid sequence identity value is generated using the sequence comparison computer program ALIGN-2.

In the case of comparing amino acid sequences using ALIGN-2, the % amino acid sequence identity of a given amino acid sequence A relative to a given amino acid sequence B (or may be expressed as a given amino acid sequence A having or containing a certain % amino acid sequence identity relative to, with or for a given amino acid sequence B) is calculated as follows:

fraction $X/Y \times 100$ wherein X is the number of identically matched amino acid residues scored by the sequence alignment program ALIGN-2 in the alignment of A and B using the program, and wherein Y is the total number of amino acid residues in B. It will be appreciated that where the length of amino acid sequence A is not equal to the length of amino acid sequence B, the % amino acid sequence identity of A relative to B will not be equal to the % amino acid sequence identity of B relative to A. Unless specifically stated otherwise, all the % amino acid sequence identity values used herein are obtained using the ALIGN-2 computer program as described in the previous paragraph.

As used herein, the terms "treatment" and "treating" refer to obtaining a desired pharmacological and/or physiologic effect. The effect may be complete or partial prevention of a disease or its symptoms and/or partial or complete cure of the disease and/or its symptoms, and includes: (a) prevention of the disease from developing in a subject that may have a predisposition to the disease but has not been diagnosed as having the disease; (b) suppression of the disease, i.e., blocking its formation; and (c) alleviation of the disease and/or its symptoms, i.e., eliminating the disease and/or its symptoms.

The terms "individual", "subject" and "patient" are used interchangeably herein and refer to mammals, including, but not limited to, murine (rats and mice), non-human primates, humans, dogs, cats, hoofed animals (e.g., horses, cattle, sheep, pigs, goats) and so on.

"Therapeutically effective amount" or "effective amount" refers to an amount of plasminogen sufficient to achieve the prevention and/or treatment of a disease when administered to a mammal or another subject to treat the disease. The "therapeutically effective amount" will vary depending on the plasminogen used, the severity of the disease and/or its symptoms, as well as the age, body weight of the subject to be treated, and the like.

2. Preparation of the Plasminogen of the Present Invention

Plasminogen can be isolated and purified from nature for further therapeutic uses, and can also be synthesized by standard chemical peptide synthesis techniques. When chemically synthesized, a polypeptide can be subjected to liquid or solid phase synthesis. Solid phase polypeptide synthesis (SPPS) is a method suitable for chemical synthesis of plasminogen, in which the C-terminal amino acid of a sequence is attached to an insoluble support, followed by the sequential addition of the remaining amino acids in the sequence. Various forms of SPPS, such as Fmoc and Boc, can be used to synthesize plasminogen. Techniques for solid phase synthesis are described in Barany and Solid-Phase Peptide Synthesis; pp. 3-284 in The Peptides: Analysis, Synthesis, Biology. Vol. 2: Special Methods in Peptide Synthesis, Part A., Merrifield et al. J. Am. Chem. Soc., 85: 2149-2156 (1963); Stewart et al. Solid Phase Peptide Synthesis, 2nd ed. Pierce Chem. Co., Rockford, Ill. (1984); and Ganesan A. 2006 Mini Rev. Med Chem. 6:3-10 and Camarero J A et al. 2005 Protein Pept Lett. 12:723-8. Briefly, small insoluble porous beads are treated with a functional unit on which a peptide chain is constructed. After repeated cycles of coupling/deprotection, the attached solid phase free N-terminal amine is coupled to a single N-protected amino acid unit. This unit is then deprotected to expose a new N-terminal amine that can be attached to another amino acid. The peptide remains immobilized on the solid phase before it is cut off.

Standard recombinant methods can be used to produce the plasminogen of the present invention. For example, a nucleic acid encoding plasminogen is inserted into an expression vector, so that it is operably linked to a regulatory sequence in the expression vector. Expression regulatory sequence includes, but is not limited to, promoters (e.g., naturally associated or heterologous promoters), signal sequences, enhancer elements and transcription termination sequences. Expression regulation can be a eukaryotic promoter system in a vector that is capable of transforming or transfecting eukaryotic host cells (e.g., COS or CHO cells). Once the vector is incorporated into a suitable host, the host is maintained under conditions suitable for high-level expression of the nucleotide sequence and collection and purification of plasminogen.

A suitable expression vector is usually replicated in a host organism as an episome or as an integral part of the host chromosomal DNA. In general, an expression vector contains a selective marker (e.g., ampicillin resistance, hygromycin resistance, tetracycline resistance, kanamycin resistance or neomycin resistance) to facilitate detection of those exogenous cells transformed with a desired DNA sequence.

*Escherichia coli* is an example of prokaryotic host cells that can be used to clone a polynucleotide encoding the plaminogen. Other microbial hosts suitable for use include *Bacillus*, for example, *Bacillus subtilis* and other species of enterobacteriaceae (such as *Salmonella* spp. and *Serratia* spp.), and various *Pseudomonas* spp. In these prokaryotic hosts, expression vectors can also be generated which will typically contain an expression control sequence (e.g., origin of replication) that is compatible with the host cell. In addition, there will be many well-known promoters, such as the lactose promoter system, the tryptophan (trp) promoter system, the beta-lactamase promoter system or the promoter system from phage lambda. Optionally in the case of manipulation of a gene sequence, a promoter will usually control expression, and has a ribosome binding site sequence and the like to initiate and complete transcription and translation.

Other microorganisms, such as yeast, can also be used for expression. *Saccharomyces* (e.g., *S. cerevisiae*) and *Pichia* are examples of suitable yeast host cells, in which a suitable vector has an expression control sequence (e.g., promoter), an origin of replication, a termination sequence and the like, as required. A typical promoter comprises 3-phosphoglycerate kinase and other glycolytic enzymes. Inducible yeast promoters specifically include promoters derived from alcohol dehydrogenase, isocytochrome C, and enzymes responsible for maltose and galactose utilization.

In addition to microorganisms, mammalian cells (e.g., mammalian cells cultured in cell culture in vitro) can also be used to express and generate the plasminogen of the present invention (e.g., a polynucleotide encoding the subject plasminogen). See Winnacker, From Genes to Clones, VCH Publishers, N.Y., N.Y. (1987). Suitable mammalian host cells include CHO cell lines, various Cos cell lines, HeLa cells, myeloma cell lines and transformed B cells or hybridomas. Expression vectors for these cells may comprise an expression control sequence, such as an origin of replication, promoter and enhancer (Queen et al. Immunol. Rev. 89:49 (1986)), as well as necessary processing information sites, such as a ribosome binding site, RNA splice site, polyadenylation site and transcription terminator sequence. Examples of suitable expression control sequences are promoters derived from white immunoglobulin gene, SV40, adenovirus, bovine papilloma virus, cytomegalovirus and the like. See Co et al. J. Immunol. 148:1149 (1992).

Once synthesized (chemically or recombinantly), the plasminogen of the present invention can be purified according to standard procedures in the art, including ammonium sulfate precipitation, affinity column, column chromatography, high performance liquid chromatography (HPLC), gel electrophoresis and the like. The plasminogen is substantially pure, e.g., at least about 80% to 85% pure, at least about 85% to 90% pure, at least about 90% to 95% pure, or 98% to 99% pure or purer, for example free of contaminants such as cell debris, macromolecules other than the plasminogen and the like.

3. Pharmaceutical Formulations

A therapeutic formulation can be prepared by mixing plasminogen of a desired purity with an optional pharmaceutical carrier, excipient or stabilizer (Remington's Pharmaceutical Sciences, 16th edition, Osol, A. ed. (1980)) to form a lyophilized preparation or an aqueous solution. Acceptable carriers, excipients and stabilizers are non-toxic to the recipient at the dosages and concentrations employed, and include buffers, such as phosphates, citrates and other organic acids; antioxidants, including ascorbic acid and methionine; preservatives (e.g., octadecyl dimethyl benzyl ammonium chloride; hexane chloride diamine; benzalkonium chloride and benzethonium chloride; phenol, butanol or benzyl alcohol; alkyl p-hydroxybenzoates, such as methyl or propyl p-hydroxybenzoate; catechol; resorcinol; cyclohexanol; 3-pentanol; and m-cresol); low molecular weight polypeptides (less than about 10 residues); proteins, such as serum albumin, gelatin or immunoglobulins; hydrophilic polymers, such as polyvinylpyrrolidone; amino acids, such as glycine, glutamine, asparagine, histidine, arginine or lysine; monosaccharides, disaccharides and other carbohydrates, including glucose, mannose or dextrins; chelating agents, such as EDTA; sugars, such as sucrose, mannitol, fucose or sorbitol; salt-forming counterions, such as sodium; metal complexes (e.g., zinc-protein complexes); and/or non-ionic surfactants, such as TWEEN™, PLURONICS™ or polyethylene glycol (PEG).

The formulations of the invention may also comprise one or more active compounds required for the particular disorder to be treated, preferably those that are complementary in activity and have no side effects with one another, for example anti-hypertensive drugs, anti-arrhythmic drugs, drugs for treating diabetes mellitus, and the like.

The plasminogen of the present invention may be encapsulated in microcapsules prepared by techniques such as coacervation or interfacial polymerization, for example, it may be incorporated in a colloid drug delivery system (e.g., liposomes, albumin microspheres, microemulsions, nanoparticles and nanocapsules), or incorporated in hydroxymethylcellulose or gel-microcapsules and poly-(methyl methacrylate) microcapsules in macroemulsions. These techniques are disclosed in Remington's Pharmaceutical Sciences, 16th edition, Osol, A. Ed. (1980).

The plasminogen of the present invention for in vivo administration must be sterile. This can be easily achieved by filtration through a sterile filtration membrane before or after freeze drying and reconstitution.

The plasminogen of the present invention can be prepared into a sustained-release preparation. Suitable examples of sustained-release preparations include solid hydrophobic polymer semi-permeable matrices having a shape and containing glycoproteins, such as films or microcapsules. Examples of sustained-release matrices include polyesters, hydrogels (e.g., poly(2-hydroxyethyl-methacrylate)) (Langer et al. J. Biomed. Mater. Res., 15: 167-277 (1981); and Langer, Chem. Tech., 12:98-105 (1982)), or poly(vinyl alcohol), polylactides (U.S. Pat. No. 3,773,919, and EP 58,481), copolymer of L-glutamic acid and ethyl-L-glutamic acid (Sidman et al. Biopolymers 22:547(1983)), nondegradable ethylene-vinyl acetate (Langer et al. supra), or degradable lactic acid-glycolic acid copolymers such as Lupron Depot™ (injectable microspheres composed of lactic acid-glycolic acid copolymer and leuprolide acetate), and poly D-(−)-3-hydroxybutyric acid. Polymers, such as ethylene-vinyl acetate and lactic acid-glycolic acid, are able to persistently release molecules for 100 days or longer, while some hydrogels release proteins for a shorter period of time. A rational strategy for protein stabilization can be designed based on relevant mechanisms. For example, if the aggregation mechanism is discovered to be formation of an intermolecular S—S bond through thio-disulfide interchange, stability is achieved by modifying sulthydryl residues, lyophilizing from acidic solutions, controlling moisture content, using appropriate additives, and developing specific polymer matrix compositions.

4. Administration and Dosage

The pharmaceutical composition of the present invention can be administered in different ways, for example by intravenous, intraperitoneal, subcutaneous, intracranial, intrathecal, intraarterial (e.g., via carotid), intramuscular, intranasal, topical or intradermal administration or spinal cord or brain delivery. An aerosol preparation, such as a nasal spray preparation, comprises purified aqueous or other solutions of the active agent along with a preservative and isotonic agent. Such preparations are adjusted to a pH and isotonic state compatible with the nasal mucosa.

In some cases, the plasminogen pharmaceutical composition of the present invention may be modified or formulated in such a manner to provide its ability to cross the blood-brain barrier. Such plasminogen compositions can be administered to an individual suffering from thrombosis and/or a thrombosis-related disease via a variety of enteral and parenteral routes of administration, including oral, intravenous and the like.

Preparations for parenteral administration include sterile aqueous or non-aqueous solutions, suspensions and emulsions. Examples of non-aqueous solvents are propylene glycol, polyethylene glycol, vegetable oils such as olive oil, and injectable organic esters such as ethyl oleate. Aqueous carriers include water, and alcoholic/aqueous solutions, emulsions or suspensions, including saline and buffered media. Parenteral vehicles include sodium chloride solution, Ringer's dextrose, dextrose and sodium chloride, or fixed oils. Intravenous vehicles include liquid and nutrient supplements, electrolyte supplements and the like. Preservatives and other additives may also be present, for example, such as antimicrobial agents, antioxidants, chelating agents and inert gases.

In some embodiments, the plasminogen of the invention is formulated with an agent that promotes the plasminogen to cross the blood-brain barrier. In some cases, the plasminogen of the present invention is fused directly or via a linker to a carrier molecule, peptide or protein that promotes the fusion to cross the blood brain barrier. In some embodiments, the plasminogen of the present invention is fused to a polypeptide that binds to an endogenous blood-brain barrier (BBB) receptor. The polypeptide that is linked to plasminogen and binds to an endogenous BBB receptor promotes the fusion to cross the BBB. Suitable polypeptides that bind to endogenous BBB receptors include antibodies (e.g., monoclonal antibodies) or antigen-binding fragments thereof that specifically bind to endogenous BBB receptors. Suitable endogenous BBB receptors include, but are not limited to, insulin receptors. In some cases, antibodies are encapsulated in liposomes. See, for example, US Patent Publication No. 2009/0156498.

The medical staff will determine the dosage regimen based on various clinical factors. As is well known in the medical field, the dosage of any patient depends on a variety of factors, including the patient's size, body surface area, age, the specific compound to be administered, sex, frequency and route of administration, overall health and other drugs administered simultaneously. The dosage range of the pharmaceutical composition comprising plasminogen of the present invention may be, for example, about 0.0001 to 2000 mg/kg, or about 0.001 to 500 mg/kg (such as 0.02 mg/kg, 0.25 mg/kg, 0.5 mg/kg, 0.75 mg/kg, 10 mg/kg and 50 mg/kg) of the subject's body weight daily. For example, the dosage may be 1 mg/kg body weight or 50 mg/kg body weight, or in the range of 1 mg/kg-50 mg/kg, or at least 1 mg/kg. Dosages above or below this exemplary range are also contemplated, especially considering the above factors. The intermediate dosages in the above range are also included in the scope of the present invention. A subject may be administered with such dosages daily, every other day, weekly or based on any other schedule determined by empirical analysis. An exemplary dosage schedule includes 1-10 mg/kg for consecutive days. During administration of the drug of the present invention, the therapeutic effect and safety are required to be assessed real-timely and regularly.

5. Treatment Efficacy and Treatment Safety

One embodiment of the present invention relates to the judgment of treatment efficacy and treatment safety after treating a subject with plasminogen.

Treatment efficacy assessment: A subject is evaluated for average daily pain from the week when the treatment begins (baseline week) to the pre-set treatment phase, and the evaluation can be carried out using the 11-point VAS scale pain score, LANSS scale, neuropathic pain scale (NPS), Likert scale (graded by 0-10 points) or the like. For example, on the VAS scale, 0 means no pain, and 11 means intolerable pain, in which:

0 point: no pain;

3 points or less: the pain is slight and tolerable;

4-6 points: the subject feels painful and the pain affects sleep but still tolerable; and 7-10 points: the subject experiences increasing pain, and the pain is intolerable and affects appetite and sleep.

It is also possible to use a finer VAS scale for scoring, for example to evaluate pain on a 100-mm scale.

Pain index can also be used as the main evaluation index, and secondary evaluation indexes are set at the same time, such as joint mobility, functional status and quality of life.

Safety assessment: In addition, the present invention also relates to the judgment of the safety of the therapeutic regimen during and after treating a subject with plasminogen and its variants, including, but not limited to, adverse event monitoring, clinical laboratory evaluation, electrocardiogram (ECG), vital signs measurements, physical and neurological examinations, etc., and statistics of serum half-life, half-life of treatment, median toxic dose (TD50) and median lethal dose (LD50) of the drug in the subject. An adverse event is defined as any adverse medical event in a drug-administered patient or clinical trial subject that does not necessarily have a causal relationship with the treatment. Adverse events usually include, but are not limited to, headaches, dizziness, upper respiratory tract infections, nausea and the like.

6. Articles of Manufacture or Kits

One embodiment of the present invention relates to an article of manufacture or a kit comprising the plasminogen/plasmin of the present invention. The article of manufacture preferably includes a container, label or package insert. Suitable containers include bottles, vials, syringes and the like. The container can be made of various materials, such as glass or plastic. The container contains a composition that is effective to treat the disease or disorder of the present invention and has a sterile access (for example, the container may be an intravenous solution bag or vial containing a plug that can be pierced by a hypodermic injection needle). At least one active agent in the composition is plasminogen/plasmin. The label on or attached to the container indicates that the composition is used to treat the diabetic neuropathy of the present invention. The article may further comprise a second container containing a pharmaceutically acceptable buffer, such as phosphate buffered saline, Ringer's solution and glucose solution. It may further comprise other substances required from a commercial and user perspective, including other buffers, diluents, filters, needles and syringes. In addition, the article comprises a package insert with instructions for use, including, for example, instructions to a user of the composition to administer the plasminogen composition and other drugs to treat an accompanying disease to a patient.

EXAMPLES

Example 1

Effect of Plasminogen on Body Weight of Experimental Animals

Figure 1:
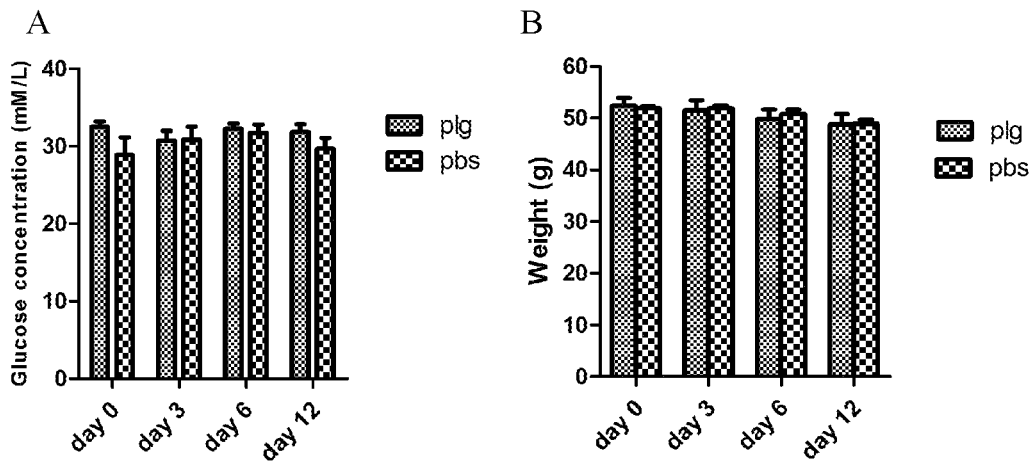
FIG. 1 shows changes in body weight after administration of plasminogen to 14-15-week-old diabetic mice.

Ten male db/db mice aged 14-15 weeks were randomly divided into two groups, five in the control group administered with vehicle PBS and five in the group administered with plasminogen, respectively. The day when the experiment began was recorded on Day 0, and the mice were weighed and grouped. From the second day of the experiment, plasminogen or PBS was administered to the mice, and the day was recorded as Day 1. Mice in the group administered with plasminogen were injected with plasminogen at a dose of 1 mg/0.1 mL/mouse/day via the tail vein, and an equal volume of PBS was administered to mice in the control group administered with vehicle PBS. The mice were weighed on days 0, 3, 6 and 12, respectively. The results showed that there was no significant difference in body weight between mice in the group administered with plasminogen and those in the control group administered with vehicle PBS on days 0, 3, 6 and 12 (FIG. 1), indicating that plasminogen has little effect on animal body weight.

Example 2

Figure 2:
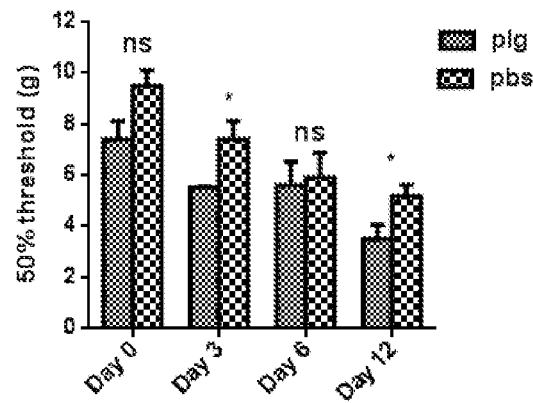
FIG. 2 shows changes in the ability to respond to mechanical allodynia after administration of plasminogen to 14-15-week-old diabetic mice.

Plasminogen Promotes the Repair of the Ability of Diabetic Mice to Respond to Algesia Ten male db/db mice aged 14-15 weeks were randomly divided into two groups, five in the control group administered with vehicle PBS and five in the group administered with plasminogen, respectively. The day when the experiment began was recorded on Day 0, and the mice were weighed and grouped. From the second day of the experiment, plasminogen or PBS was administered to the mice, and the day was recorded as Day 1. Mice in the group administered with plasminogen were injected with plasminogen at a dose of 1 mg/0.1 mL/mouse/day via the tail vein, and an equal volume of PBS was administered to mice in the control group administered with vehicle PBS. On days 0, 3, 6 and 12 after administration of plasminogen, animals were detected for their sensitivity to mechanical injury using Von-Frey filaments (Stoelting, USA). With 2.0 g force as the starting force, the left foot was first detected. If there were 4 paw withdrawals for 5 stimulations, it was positive and it was recorded as the threshold of the animal's sensitivity to mechanical injury. If the stimulus response with 2.0 g force was negative, the right foot was stimulated with a large force; if it was positive, it was recorded as its threshold; and if it was negative, it will continue to stimulate its left foot with a large force, and the left and right feet of diabetic mice were thus alternately stimulated until a positive reaction occurred PI. The statistical results of the experiment with Von Frey filaments showed that mice in the group administered with plasminogen were observed to have a significantly lower 50% algesia threshold than those in the control group administered with vehicle PBS both after 3 days of administration and 11 days of administration (FIG. 2), indicating that plasminogen repairs the ability of diabetic mice to respond to mechanical allodynia.

Example 3

Plasminogen Restores Neural Response of Diabetic Mice to Cold Stimulation

Ten male db/db mice aged 14-15 weeks were randomly divided into two groups, five in the control group administered with vehicle PBS and five in the group administered with plasminogen, respectively. The day when the experiment began was recorded on Day 0, and the mice were weighed and grouped. From the second day of the experiment, plasminogen or PBS was administered to the mice, and the day was recorded as Day 1. Mice in the group administered with plasminogen were injected with plasminogen at a dose of 1 mg/0.1 mL/mouse/day via the tail vein, and an equal volume of PBS was administered to mice in the control group administered with vehicle PBS. On days 0, 3, 6 and 12 after administration of plasminogen, a drop of acetone was squeezed out with a needleless syringe and the planta of each diabetic mouse was slightly touched to cover the entire planta with acetone. Starting from the left foot, the left and right feet were stimulated alternately every 3 minutes for a total of 10 stimulations, and the number of paw withdrawals was counted. Percentage of response=number of paw withdrawals/number of stimulations×100%.

Figure 3:
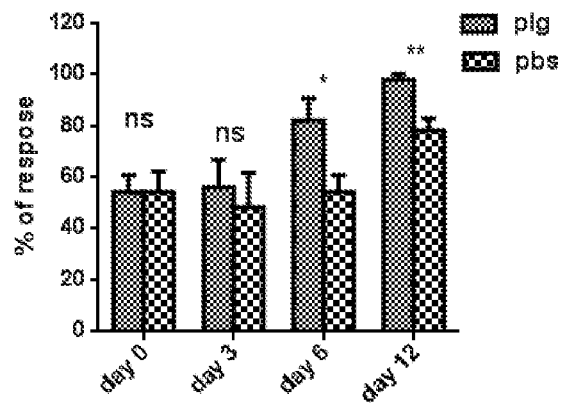
FIG. 3 shows the detection results of the ability to respond to cold stimulation on days 0, 3, 6 and 12 after administration of plasminogen to 14-15-week-old diabetic mice.

The experimental results showed that there was no significant difference in the response to acetone stimulation between mice in the group administered with plasminogen and those in the control group on days 0 and 3; however, a significant difference was observed from day 6, and an extremely significant difference was observed on day 12 (FIG. 3). These results indicated that mice were showed to be significantly sensitive to cold sensation 6 days after administration of plasminogen, and to have an extremely significant difference in response on day 12, indicating that plasminogen remarkably repairs the injury in neural response of diabetic mice to cold stimulation.

Example 4

Plasminogen Repairs Response of Diabetic Mice to Mechanical Hyperalgesia

Figure 4:
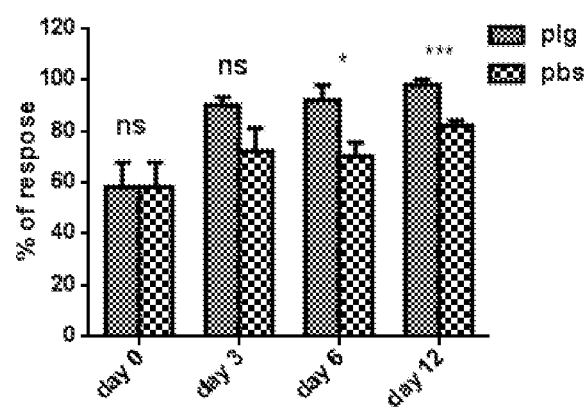
FIG. 4 shows the detection results of the ability to respond to mechanical hyperalgesia on days 0, 3, 6 and 12 after administration of plasminogen to 14-15-week-old diabetic mice.

Ten male db/db mice aged 14-15 weeks were randomly divided into two groups, five in the control group administered with vehicle PBS and five in the group administered with plasminogen, respectively. The day when the experiment began was recorded on Day 0, and the mice were weighed and grouped. From the second day of the experiment, plasminogen or PBS was administered to the mice, and the day was recorded as Day 1. Mice in the group administered with plasminogen were injected with plasminogen at a dose of 1 mg/0.1 mL/mouse/day via the tail vein, and an equal volume of PBS was administered to mice in the control group administered with vehicle PBS. On days 0, 3, 6 and 12 after administration of plasminogen, db/db mice were stimulated at the planta with an American-standard 27 gauge-needle with a force that gently touched the planta of the mice but failed to pierce the corium layer. Starting from the left foot, the left and right feet were stimulated alternately every 3 minutes for a total of 10 stimulations, and the number of paw withdrawals was counted. Percentage of response=number of paw withdrawals/number of stimulations×100%. Difference in acupuncture response between mice in the group administered with plasminogen and those in the control group administered with vehicle PBS was extremely significant, and the P value was <0.0001 (FIG. 4), indicating that plasminogen extremely significantly repairs the injury in neuromechanical hyperalgesia response caused by diabetes mellitus.

Example 5

Effect of Plasminogen on Body Weight of Late Diabetic Mice with Nerve Injury

Figure 5:
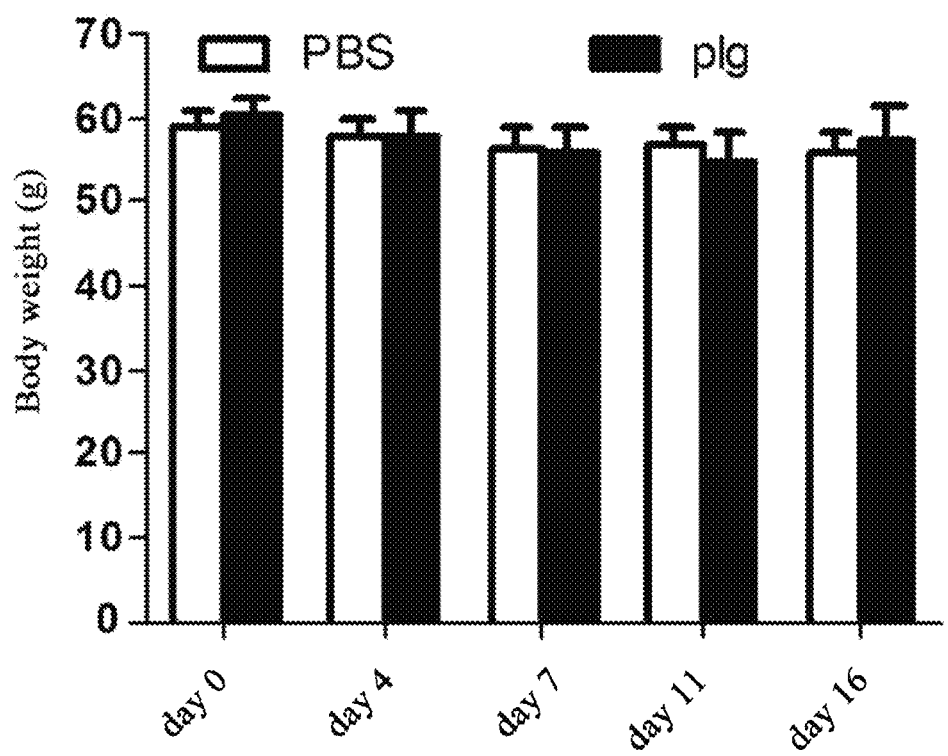
FIG. 5 shows changes in body weight after administration of plasminogen to 24-25-week-old diabetic mice.

Ten male db/db mice aged 24-25 weeks were randomly divided into two groups, five in the control group administered with vehicle PBS and five in the group administered with plasminogen, respectively. The day when the experiment began was recorded on Day 0, and the mice were weighed and grouped. From the second day of the experiment, plasminogen or PBS was administered to the mice for 15 consecutive days, and the day was recorded as Day 1. Mice in the group administered with plasminogen were injected with plasminogen at a dose of 2 mg/0.2 mL/mouse/day via the tail vein, and an equal volume of PBS was administered to mice in the control group administered with vehicle PBS. The mice were weighed on days 0, 4, 7, 11 and 16 after administration of plasminogen, respectively. The results showed that there was no significant difference in body weight between mice in the group administered with plasminogen and those in the control group administered with vehicle PBS on days 0, 4, 7, 11 and 16 (FIG. 5), indicating that plasminogen has little effect on animal body weight.

Example 6

Plasminogen Promotes the Repair of the Ability of Late Diabetic Mice with Nerve Injury to Respond to Mechanical Allodynia Ten male db/db mice aged 24-25 weeks were randomly divided into two groups, five in the control group administered with vehicle PBS and five in the group administered with plasminogen, respectively. The day when the experiment began was recorded on Day 0, and the mice were weighed and grouped. From the second day of the experiment, plasminogen or PBS was administered to the mice for 15 consecutive days, and the day was recorded as Day 1. Mice in the group administered with plasminogen were injected with plasminogen at a dose of 2 mg/0.2 mL/mouse/day via the tail vein, and an equal volume of PBS was administered to mice in the control group administered with vehicle PBS. On days 0, 4, 7, 11 and 16 after administration of plasminogen, animals were detected for their sensitivity to mechanical injury using Von-Frey filaments (Stoelting, USA). With 2.0 g force as the starting force, the left foot was first detected. If there were 2 paw withdrawals for 5 stimulations, it was positive; and if it was positive, the right foot was then stimulated with a smaller force. If it was negative, the right foot was stimulated with a larger force, the left and right feet were thus alternately stimulated for a total of 6 stimulations at a stimulation interval of 5 minutes, and then the 50% paw withdrawal threshold was calculated according to the method introduced in S. R. Chaplan et. al. (1994)[32].

Figure 6:
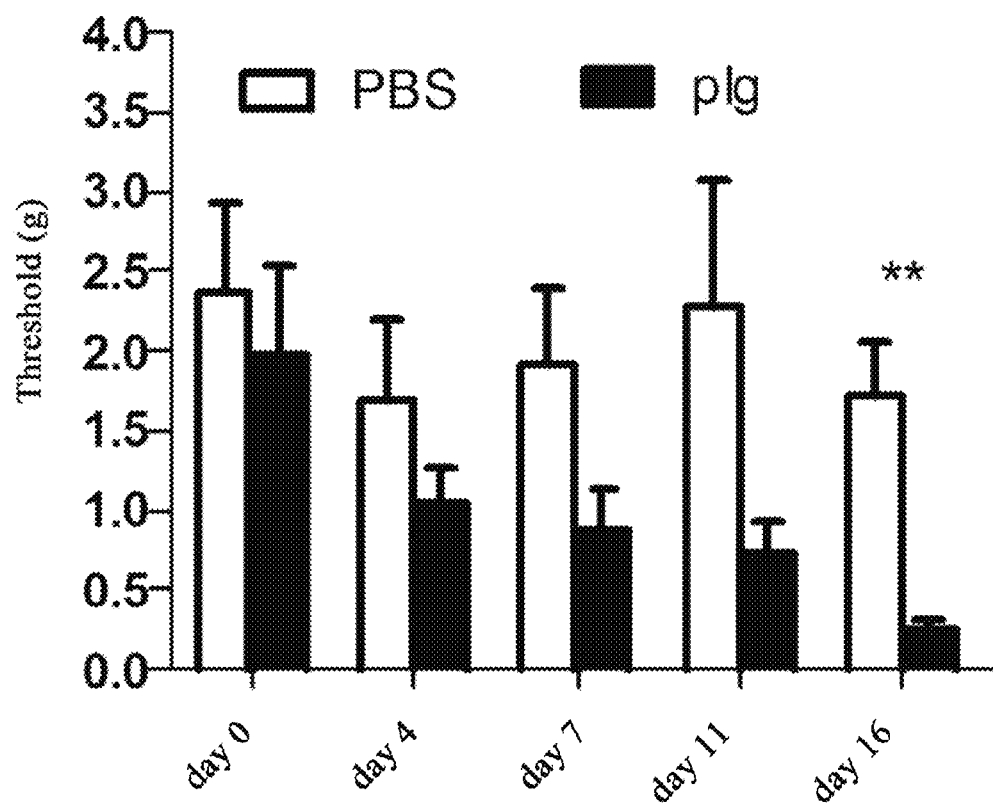
FIG. 6 shows the detection results of the ability to respond to mechanical allodynia on days 0, 4, 7, 11 and 16 after administration of plasminogen to 24-25-week-old diabetic mice.

The study found that compared with mice in the control group administered with vehicle PBS, diabetic mice in the group administered with plasminogen showed uniform increase in the response to mechanical allodynia, and an extremely significant difference was found on day 16 compared with mice in the control group administered with vehicle PBS (FIG. 6), indicating that plasminogen repairs the ability of late diabetic mice with nerve injury to respond to mechanical allodynia.

Example 7

Plasminogen Repairs Response of Late Diabetic Mice with Nerve Injury to Cold Stimulation Ten male db/db mice aged 24-25 weeks were randomly divided into two groups, five in the control group administered with vehicle PBS and five in the group administered with plasminogen, respectively. The day when the experiment began was recorded on Day 0, and the mice were weighed and grouped. From the second day of the experiment, plasminogen or PBS was administered to the mice for 15 consecutive days, and the day was recorded as Day 1. Mice in the group administered with plasminogen were injected with plasminogen at a dose of 2 mg/0.2 mL/mouse/day via the tail vein, and an equal volume of PBS was administered to mice in the control group administered with vehicle PBS. On days 0, 4, 7, 11 and 16 after administration, a drop of acetone was squeezed out with a needleless syringe and the planta of each db/db mouse was slightly touched to cover the entire planta with acetone. Starting from the left foot, the left and right feet were stimulated alternately every 3 minutes for a total of 10 stimulations, and the number of paw withdrawals was counted. Percentage of response=number of paw withdrawals/number of stimulations×100%.

Figure 7:
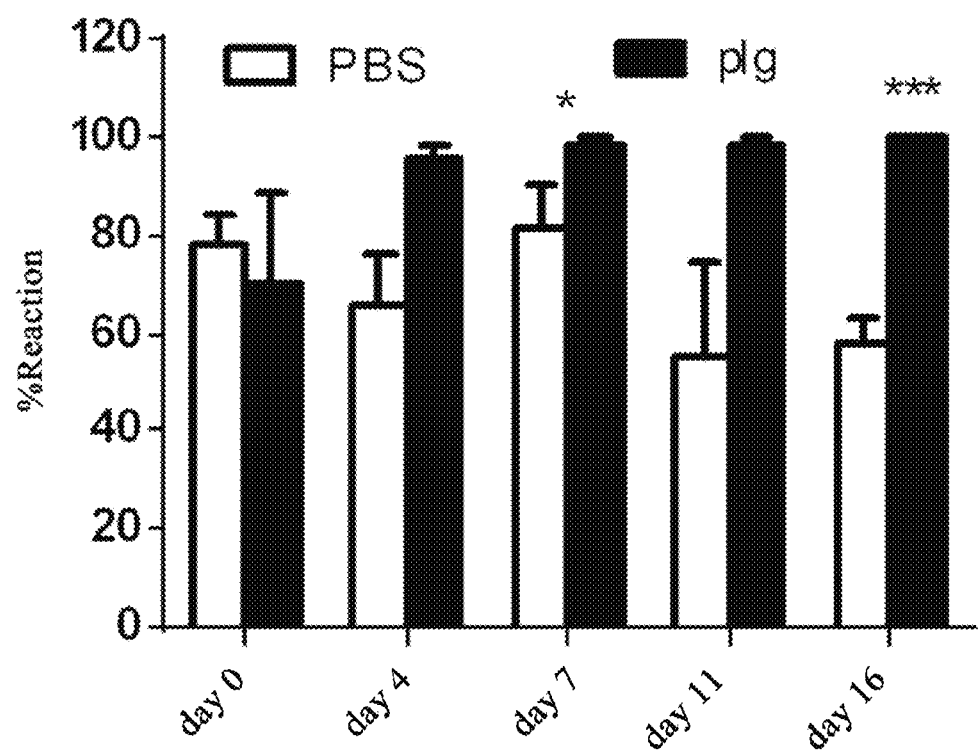
FIG. 7 shows the detection results of the ability to respond to cold stimulation on days 0, 4, 7, 11 and 16 after administration of plasminogen to 24-25-week-old diabetic mice.

The experimental results showed that there was no significant difference in the response to acetone stimulation between mice in the group administered with plasminogen and those in the control group administered with vehicle PBS on days 0 and 4; however, a significant difference was observed from day 7, and an extremely significant difference was observed on day 16, and the P value was <0.0001 (FIG. 7), indicating that after 15 days of administration, diabetic mice almost completely restored response to cold stimulation, suggesting that plasminogen extremely significantly repairs the injury in nerve for cold stimulation in late diabetes mellitus.

Example 8

Plasminogen Repairs Response of Late Diabetic Mice with Nerve Injury to Mechanical Hyperalgesia Ten male db/db mice aged 24-25 weeks were randomly divided into two groups, five in the control group administered with vehicle PBS and five in the group administered with plasminogen, respectively. The day when the experiment began was recorded on Day 0, and the mice were weighed and grouped. From the second day of the experiment, plasminogen or PBS was administered to the mice for 15 consecutive days, and the day was recorded as Day 1. Mice in the group administered with plasminogen were injected with plasminogen at a dose of 2 mg/0.2 mL/mouse/day via the tail vein, and an equal volume of PBS was administered to mice in the control group administered with vehicle PBS. On days 0, 4, 7, 11 and 16 after administration of plasminogen, db/db mice were stimulated at the planta with a 27-gauge needle with a force that gently touched the planta of the mice but failed to pierce the corium layer. Starting from the left foot, the left and right feet were stimulated alternately every 3 minutes for a total of 10 stimulations, and the number of paw withdrawals was counted. Percentage of response=number of paw withdrawals/number of stimulations×100%.

Figure 8:
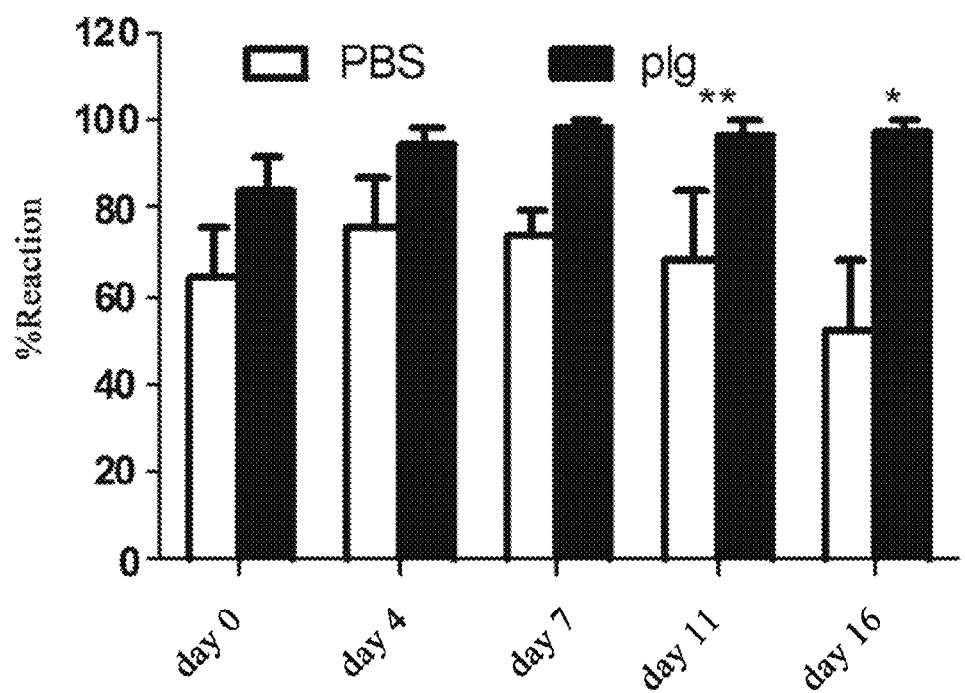
FIG. 8 shows the detection results of the ability to respond to mechanical hyperalgesia on days 0, 4, 7, 11 and 16 after administration of plasminogen to 24-25-week-old diabetic mice.

The experimental results showed that different degrees of restoration of response to acupuncture stimulation were observed in late diabetic mice with nerve injury on day 7 or earlier after administration of plasminogen, and an extremely significant difference and a significant difference in acupuncture stimulation response were observed between mice in the group administered with plasminogen and those in the control group administered with vehicle PBS on days 11 and 16 (FIG. 8), indicating that plasminogen extremely significantly repairs response of late diabetic mice to mechanical hyperalgesia.

Example 9

Protective Effect of Plasminogen on Nerve Tissue Injury of Late Diabetic Mice with Nerve Injury Ten male db/db mice aged 24-25 weeks were randomly divided into two groups, five in the control group administered with vehicle PBS and five in the group administered with plasminogen, respectively. The day when the experiment began was recorded on Day 0, and the mice were weighed and grouped. From the second day of the experiment, plasminogen or PBS was administered to the mice for 15 consecutive days, and the day was recorded as Day 1. Mice in the group administered with plasminogen were injected with plasminogen at a dose of 2 mg/0.2 mL/mouse/day via the tail vein, and an equal volume of PBS was administered to mice in the control group administered with vehicle PBS. Mice were sacrificed on day 16, and sciatic nerves were fixed in 10% neutral formalin fixative for 24 hours. The fixed sciatic nerves were paraffin-embedded after dehydration with alcohol gradient and permeabilization with xylene. The thickness of the tissue sections was 5 μm. The sections were dewaxed and rehydrated, stained with hematoxylin and eosin (HE staining), differentiated with 1% hydrochloric acid in alcohol, and returned to blue with ammonia water. The sections were sealed after dehydration with alcohol gradient and observed under a microscope at 400×.

Figure 9:
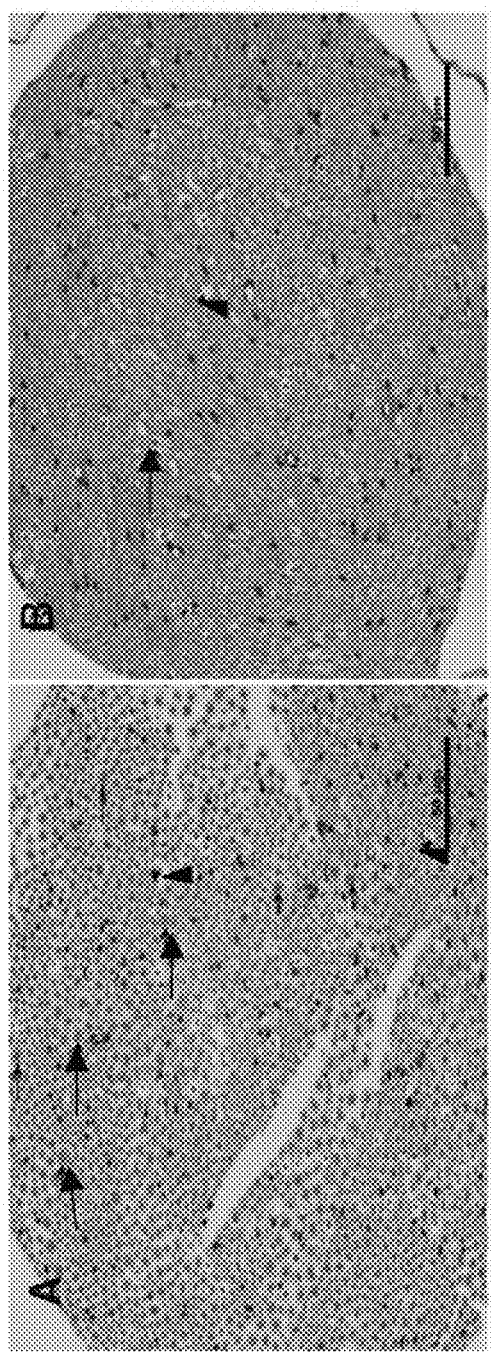
FIG. 9 shows the observed results of HE staining of the sciatic nerve after administration of plasminogen to 24-25-week-old diabetic mice for 15 consecutive days.

The experimental results showed that mice in the control group administered with vehicle PBS had widened sciatic nerve fiber gap, wherein a large number of myelin sheaths and axons were swollen (↑), and a small number of axons were disintegrated (▲) (FIG. 9A). However, mice in the plasminogen group had closely arranged nerve fibers, and only a small amount of myelin sheaths and axons were swollen and disintegrated (FIG. 9B). This indicated that plasminogen has a certain repair effect on nerve tissue injury of late diabetic mice.

Example 10

Plasminogen Reduces the Fibrin Level in Nerve Tissues of Late Diabetic Mice with Nerve Injury Ten male db/db mice aged 24-25 weeks were randomly divided into two groups, five in the control group administered with vehicle PBS and five in the group administered with plasminogen, respectively. The day when the experiment began was recorded on Day 0, and the mice were weighed and grouped. From the second day of the experiment, plasminogen or PBS was administered to the mice for 15 consecutive days, and the day was recorded as Day 1. Mice in the group administered with plasminogen were injected with plasminogen at a dose of 2 mg/0.2 mL/mouse/day via the tail vein, and an equal volume of PBS was administered to mice in the control group administered with vehicle PBS. Mice were sacrificed on day 16, and sciatic nerves were fixed in 10% neutral formalin fixative for 24 hours. The fixed sciatic nerves were paraffin-embedded after dehydration with alcohol gradient and permeabilization with xylene. The thickness of the tissue sections was 5 μm. The sections were dewaxed and rehydrated and washed with water once, and then the tissues were circled with a PAP pen. The sections were incubated with hydrogen peroxide diluted with 3% TBS for 15 minutes, and washed with water three times. The sections were blocked with 10% normal goat serum (Vector laboratories, Inc., USA) for 1 hour, and excess serum was aspirated. The sections were incubated with rabbit anti-mouse fibrin (fibrinogen) antibody (Abcam) for 1 hour at room temperature or overnight at 4° C. and washed with TBS three times. The sections were incubated with a secondary antibody, goat anti-rabbit IgG (HRP) antibody (Abcam), for 1 hour at room temperature and washed with TBS three times. The sections were developed with a DAB kit (Vector laboratories, Inc., USA). After washing with water three times, the sections were counterstained with hematoxylin for 30 seconds and flushed with running water for 5 minutes. After gradient dehydration, permeabilization and sealing, the sections were observed under a microscope at 400×.

Fibrinogen is the precursor of fibrin, and in the presence of tissue injury, as a stress response to the body's injury, fibrinogen is hydrolyzed into fibrin [33-35]. Therefore, the fibrinogen level can be used as a sign of the degree of injury.

Figure 10:
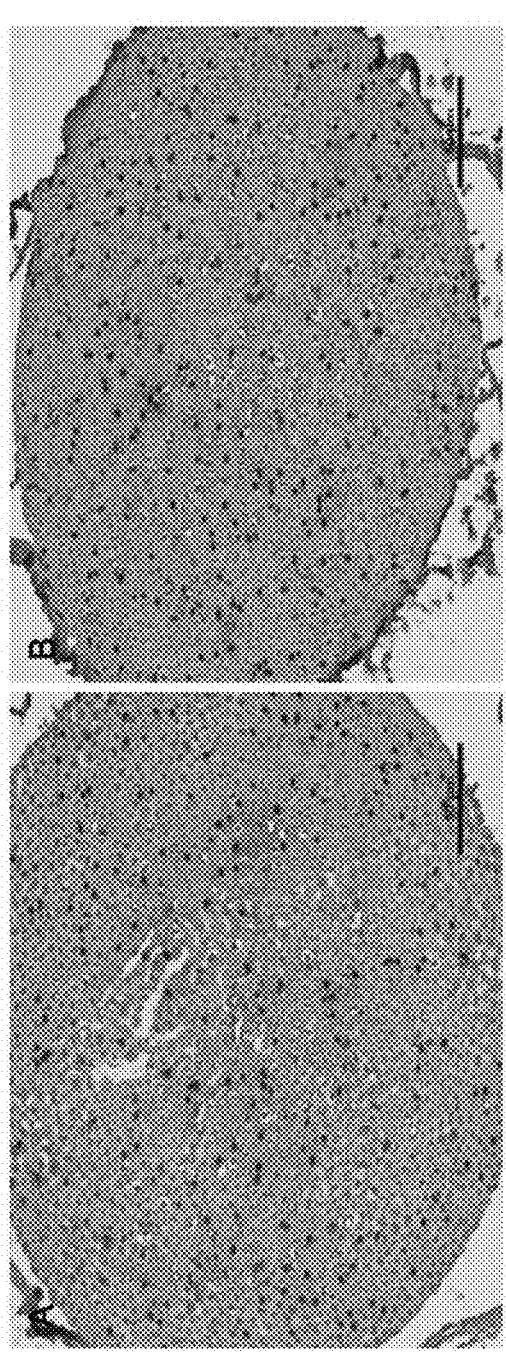
FIG. 10 shows the observed results of fibrin immunostaining of the sciatic nerve after administration of plasminogen to 24-25-week-old diabetic mice for 15 consecutive days.

The study found that compared with mice in the control group administered with vehicle PBS (FIG. 10A), those in the group administered with plasminogen (FIG. 10B) had a decreased fibrin level in the sciatic nerve, indicating that plasminogen repairs the nerve tissue injury to a certain degree.

Example 11

Plasminogen Reduces the Fibrin Level in Liver Tissues in Late Diabetes Mellitus

Ten male db/db mice aged 24-25 weeks were randomly divided into two groups, five in the control group administered with vehicle PBS and five in the group administered with plasminogen, respectively. The day when the experiment began was recorded on Day 0, and the mice were weighed and grouped. From the second day of the experiment, plasminogen or PBS was administered to the mice for 31 consecutive days, and the day was recorded as Day 1. Mice in the group administered with plasminogen were injected with plasminogen at a dose of 2 mg/0.2 mL/mouse/day via the tail vein, and an equal volume of PBS was administered to mice in the control group administered with vehicle PBS. Mice were sacrificed on day 32, and liver tissues were fixed in 10% neutral formalin fixative for 24 hours. The fixed liver tissues were paraffin-embedded after dehydration with alcohol gradient and permeabilization with xylene. The thickness of the tissue sections was 5 μm. The sections were dewaxed and rehydrated and washed with water once. The sections were incubated with 3% hydrogen peroxide for 15 minutes and wash with water twice for 5 minutes each time. The sections were blocked with 10% normal goat serum solution (Vector laboratories, Inc., USA) for 1 hour; and after the time was up, the goat serum solution was discarded, and the tissues were circled with a PAP pen. The sections were incubated with rabbit anti-mouse fibrin (fibrinogen) antibody (Abcam) overnight at 4° C. and washed with TBS twice for 5 minutes each time. The sections were incubated with a secondary antibody, goat anti-rabbit IgG (HRP) antibody (Abcam), for 1 hour at room temperature and washed with TBS twice for 5 minutes each time. The sections were developed with a DAB kit (Vector laboratories, Inc., USA). After washing with water three times, the sections were counterstained with hematoxylin for 30 seconds and flushed with running water for 5 minutes. After gradient dehydration, permeabilization and sealing, the sections were observed under a microscope at 200×.

Fibrinogen is the precursor of fibrin, and in the presence of tissue injury, as a stress response to the body's injury, fibrinogen is hydrolyzed into fibrin[33-35]. Therefore, the fibrin level can be used as a sign of the degree of injury.

Figure 11:
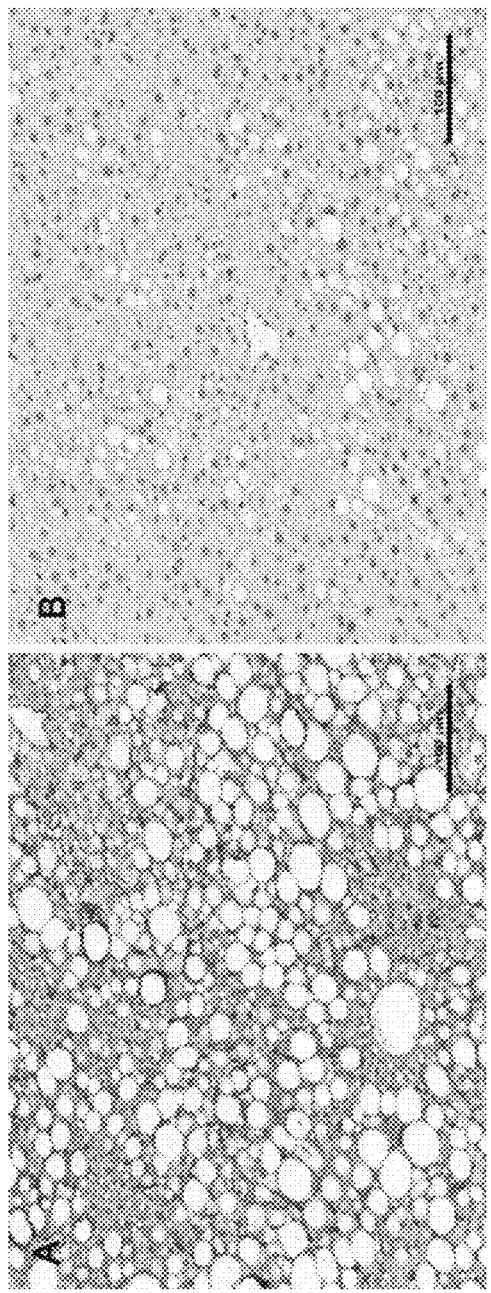
FIG. 11 shows the observed results of fibrin immunostaining of the liver after administration of plasminogen to 24-25-week-old diabetic mice for 31 consecutive days.

The study found that compared with mice in the control group administered with vehicle PBS (FIG. 11A), those in the group administered with plasminogen (FIG. 11B) had a lighter fibrin-positive staining in the liver tissues, indicating that injection of plasminogen can significantly reduce fibrin deposited in the liver tissues of diabetic mice, reflecting the significant repair effect of plasminogen on the liver tissue injury of diabetic mice.

Example 12

Plasminogen Reduces Inflammation of Liver Tissues of Late Diabetic Mice

Ten male db/db mice aged 24-25 weeks were randomly divided into two groups, five in the control group administered with vehicle PBS and five in the group administered with plasminogen, respectively. The day when the experiment began was recorded on Day 0, and the mice were weighed and grouped. From the second day of the experiment, plasminogen or PBS was administered to the mice for 31 consecutive days, and the day was recorded as Day 1.

Mice in the group administered with plasminogen were injected with plasminogen at a dose of 2 mg/0.2 mL/mouse/day via the tail vein, and an equal volume of PBS was administered to mice in the control group administered with vehicle PBS. Mice were sacrificed 31 days after administration of plasminogen, and liver tissues were fixed in 10% neutral formalin fixative for 24 hours. The fixed liver tissues were paraffin-embedded after dehydration with alcohol gradient and permeabilization with xylene. The thickness of the tissue sections was 5 µm. The sections were dewaxed and rehydrated and washed with water once. The sections were incubated with 3% hydrogen peroxide for 15 minutes and wash with water twice for 5 minutes each time. The sections were blocked with 10% normal goat serum (Vector laboratories, Inc., USA) for 1 hour, and after the time was up, the serum was thrown away, and the tissues were circled with a PAP pen. The sections were incubated with a rabbit polyclonal antibody against F4/80 (Abcam) overnight at 4° C. and washed with TBS twice for 5 minutes each time. The sections were incubated with a secondary antibody, goat anti-rabbit IgG (HRP) antibody (Abcam), for 1 hour at room temperature and washed with TBS twice. The sections were developed with a DAB kit (Vector laboratories, Inc., USA). After washing with water three times, the sections were counterstained with hematoxylin for 30 seconds and flushed with running water for 5 minutes. After gradient dehydration, permeabilization and sealing, the sections were observed under a microscope at 400×.

Figure 12:
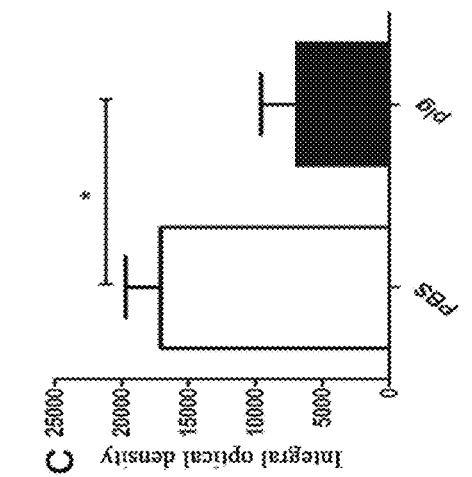
FIG. 12 shows the observed results of F4/80 immunostaining of the liver after administration of plasminogen to 24-25-week-old diabetic mice for 31 consecutive days.
Figure 12:
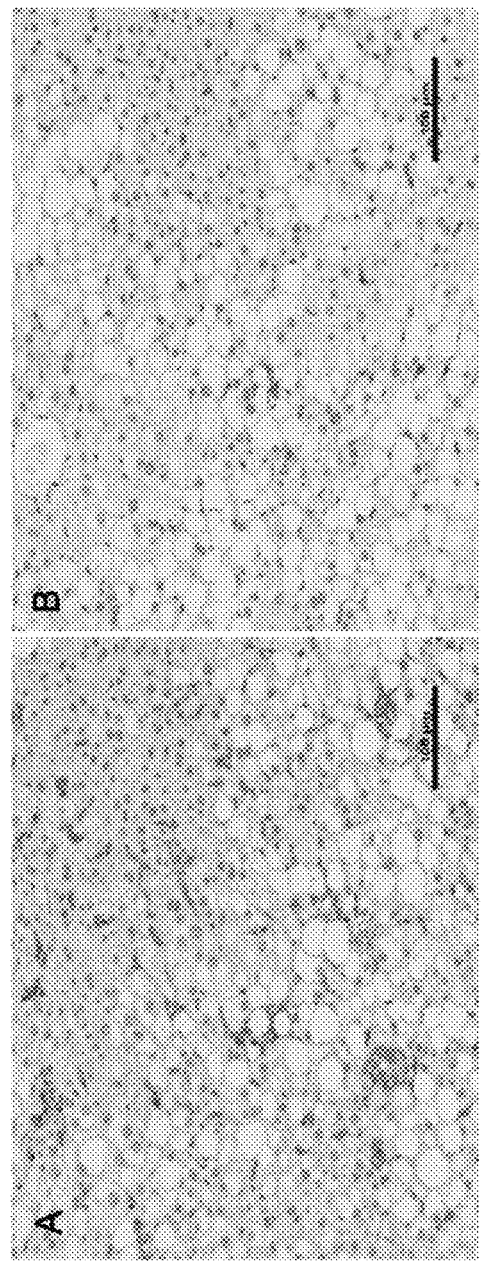

F4/80 is a macrophage marker that can indicate the extent and stage of an inflammatory response. The results showed that compared with mice in the control group administered with vehicle PBS (FIG. 12A), the F4/80 positive expression was significantly reduced in those in the group administered with plasminogen (FIG. 12B), indicating that inflammation of the liver tissues is reduced after administration of plasminogen. FIG. 12C shows the results of quantitative analysis of F4/80 immunohistochemical positive expression, in which the expression of F4/80 in mice in the group administered with plasminogen was significantly reduced with statistical difference, indicating that injection of plasminogen can significantly reduce the liver inflammation of diabetic mice.

Example 13

Plasminogen Promotes Fibrin Hydrolysis in the Kidneys of Late Diabetic Mice

Twenty male db/db mice aged 24-25 weeks were randomly divided into two groups, ten in the control group administered with vehicle PBS and ten in the group administered with plasminogen, respectively. The day when the experiment began was recorded on Day 0, and the mice were weighed and grouped. From the second day of the experiment, plasminogen or PBS was administered to the mice for 31 consecutive days, and the day was recorded as Day 1. Mice in the group administered with plasminogen were injected with plasminogen at a dose of 2 mg/0.2 mL/mouse/day via the tail vein, and an equal volume of PBS was administered to mice in the control group administered with vehicle PBS. Mice were sacrificed on day 32, and the kidneys were fixed in 10% neutral formalin fixative for 24 hours. The fixed kidney tissues were paraffin-embedded after dehydration with alcohol gradient and permeabilization with xylene. The thickness of the tissue sections was 5 µm. The sections were dewaxed and rehydrated and washed with water once. The sections were incubated with 3% hydrogen peroxide for 15 minutes and wash with water twice for 5 minutes each time. The sections were blocked with 10% normal goat serum solution (Vector laboratories, Inc., USA) for 1 hour; and after the time was up, the goat serum solution was discarded, and the tissues were circled with a PAP pen. The sections were incubated with rabbit anti-mouse fibrin (fibrinogen) antibody (Abcam) overnight at 4° C. and washed with TBS twice for 5 minutes each time. The sections were incubated with a secondary antibody, goat anti-rabbit IgG (HRP) antibody (Abcam), for 1 hour at room temperature and washed with TBS twice for 5 minutes each time. The sections were developed with a DAB kit (Vector laboratories, Inc., USA). After washing with water three times, the sections were counterstained with hematoxylin for 30 seconds and flushed with running water for 5 minutes. After gradient dehydration, permeabilization and sealing, the sections were observed under a microscope at 200×.

Fibrinogen is the precursor of fibrin, and in the presence of tissue injury, as a stress response to the body's injury, fibrinogen is hydrolyzed into fibrin and deposited at the injury site[33-35]. Therefore, the fibrin level can be used as a sign of the degree of injury.

Figure 13:
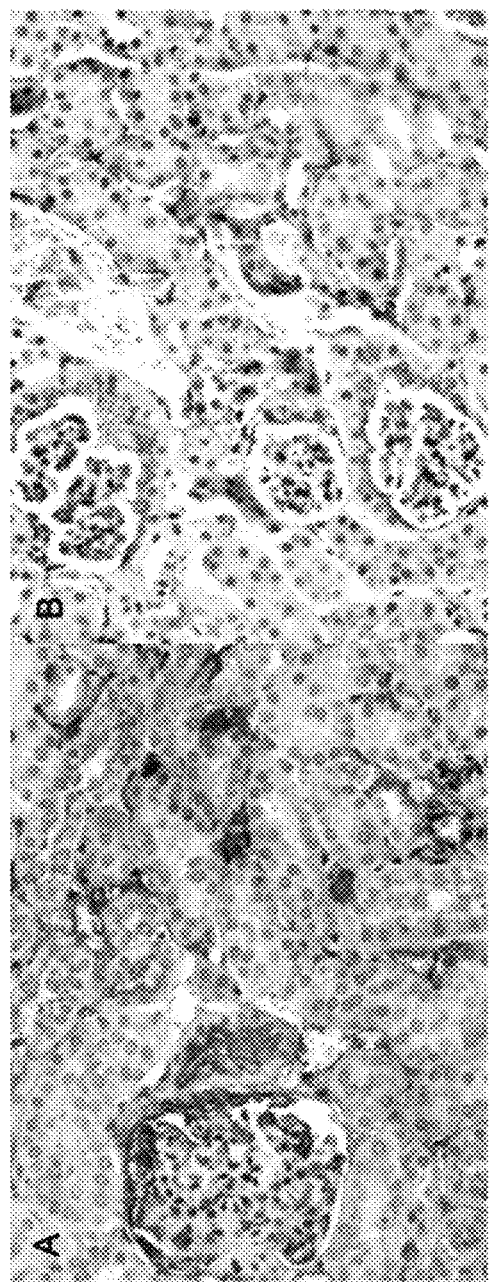
FIG. 13 shows the observed results of fibrin immunostaining of the kidneys after administration of plasminogen to 24-25-week-old diabetic mice for 31 consecutive days.

The results showed that compared with mice in the control group administered with vehicle PBS (FIG. 13A), mice in the group administered with plasminogen (FIG. 13B) had a lighter fibrinogen-positive staining, indicating that injection of plasminogen can significantly reduce fibrin deposited in the kidneys of diabetic mice, reflecting that plasminogen has a significant repair effect on the body's injury of diabetic mice.

Example 14

Plasminogen Promotes the Expression of Bcl-2, an Apoptosis Inhibitory Protein, in the Kidneys of Late Diabetic Mice Twenty male db/db mice aged 24-25 weeks were randomly divided into two groups, ten in the control group administered with vehicle PBS and ten in the group administered with plasminogen, respectively. The day when the experiment began was recorded on Day 0, and the mice were weighed and grouped. From the second day of the experiment, plasminogen or PBS was administered to the mice for 31 consecutive days, and the day was recorded as Day 1. Mice in the group administered with plasminogen were injected with plasminogen at a dose of 2 mg/0.2 mL/mouse/day via the tail vein, and an equal volume of PBS was administered to mice in the control group administered with vehicle PBS. Mice were sacrificed on day 32, and the kidneys were fixed in 10% neutral formalin fixative for 24 hours. The fixed kidney tissues were paraffin-embedded after dehydration with alcohol gradient and permeabilization with xylene. The thickness of the tissue sections was 5 µm. The sections were dewaxed and rehydrated and washed with water once. The sections were incubated with 3% hydrogen peroxide for 15 minutes and wash with water twice for 5 minutes each time. The sections were blocked with 10% normal goat serum solution (Vector laboratories, Inc., USA) for 1 hour; and after the time was up, the goat serum solution was discarded, and the tissues were circled with a PAP pen. The sections were incubated with rabbit anti-mouse Bcl-2 antibody (Abcam) at 4° C. overnight and washed with TBS twice for 5 minutes each time. The sections were incubated with a secondary antibody, goat anti-rabbit IgG (HRP) antibody (Abcam), for 1 hour at room temperature and washed with TBS twice for 5 minutes each time. The sections were developed with a DAB kit (Vector laboratories, Inc., USA). After washing with water three times, the sections were counterstained with hematoxylin for 30 seconds and flushed with running water for 5 minutes. After gradient dehydration, permeabilization and sealing, the sections were observed under a microscope at 200×.

Figure 14:
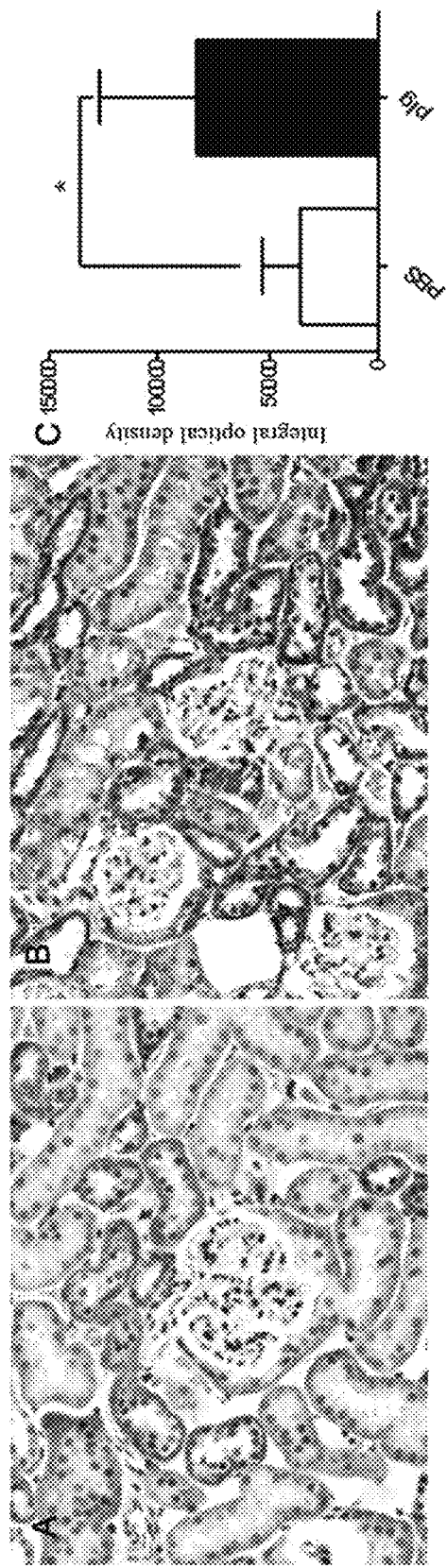
FIG. 14 shows the observed results of Bcl-2 immunostaining of the kidneys after administration of plasminogen to 24-25-week-old diabetic mice for 31 consecutive days.

Bcl-2 is an apoptosis inhibitory protein, and its expression will be down-regulated under the action of an apoptosis stimulating factor[36,37]. The Bcl-2 immunohistochemical results showed that the positive expression staining of tubular epithelial cells in mice in the group administered with plasminogen (FIG. 14B) was significantly darker than that of tubular epithelial cells in those in the control group administered with vehicle PBS (FIG. 14A), and the former had a wider range of staining. The results of quantitative analysis were consistent with the observations, and there were significant differences (as shown in FIG. 14C). This indicated that plasminogen can promote the expression of Bcl-2, an apoptosis inhibitory molecule, in the kidneys of diabetic mice, and thus can inhibit the apoptosis in the kidney tissues of diabetic mice.

Example 15

Plasminogen Improves Injury of the Retina of Late Diabetic Mice

Twenty male db/db mice aged 24-25 weeks were randomly divided into two groups, ten in the control group administered with vehicle PBS and ten in the group administered with plasminogen, respectively. The day when the experiment began was recorded on Day 0, and the mice were weighed and grouped. From the second day of the experiment, plasminogen or PBS was administered to the mice for 31 consecutive days, and the day was recorded as Day 1. Mice in the group administered with plasminogen were injected with plasminogen at a dose of 2 mg/0.2 mL/mouse/day via the tail vein, and an equal volume of PBS was administered to mice in the control group administered with vehicle PBS. Mice were sacrificed on day 32, and the left eyeballs were fixed in paraformaldehyde fixative for 24 hours. The retina was detached from the fixed eyeballs and placed in an 1 mL EP tube containing 3% pancreatin (Solarbio), and shaken for digestion in a shaker at 37° C. for 2-3 h. After the retina was softened and detached, the retina was carefully transferred into an EP tube filled with distilled water and shaken in a shaker at 37° C. for 2-3 h to detach excess tissues from the retina. The retina was gently pipetted, leaving only the blood vessel layer, and then spread on a glass slide and air dried. The retina was stained in periodic acid-Schiff solution (PAS staining), differentiated with 1% hydrochloric acid in alcohol, and returned to blue with ammonia water. The slide was sealed after dehydration with alcohol gradient and permeabilization with xylene, and observed under a microscope at 400×.

Figure 15:
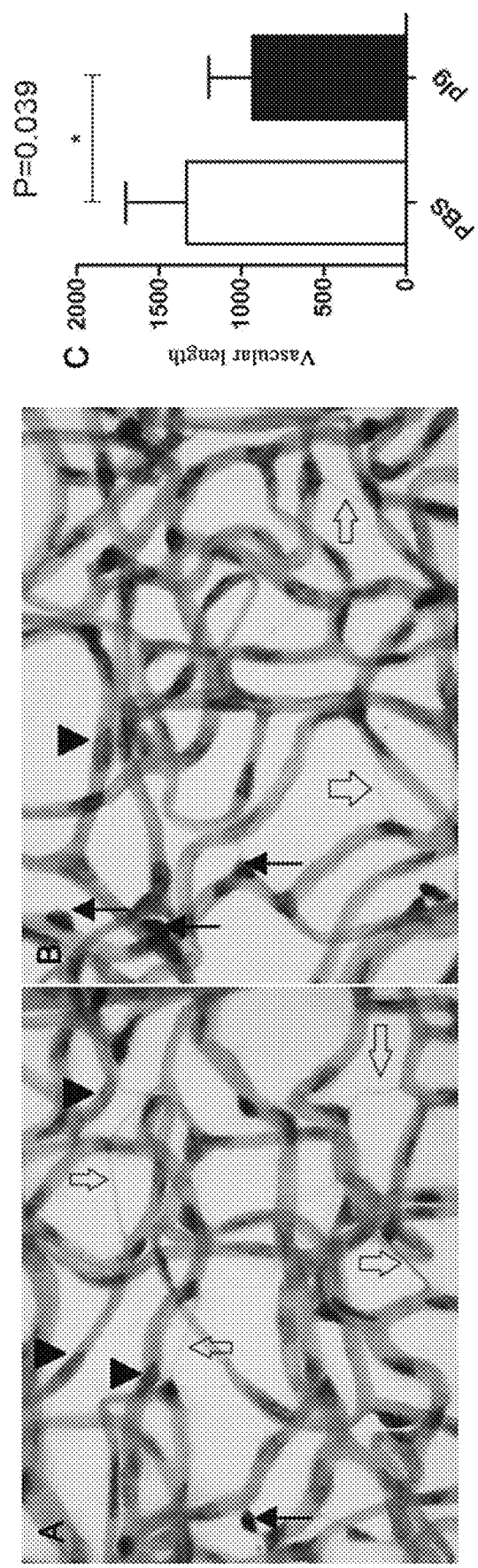
FIG. 15 shows the observed results of PAS staining of the retina after administration of plasminogen to 24-25-week-old diabetic mice for 31 consecutive days.

From the experimental results, it can be seen that compared with the plasminogen group (FIG. 15B), the retinal capillary diameters of the db/db mice in the control group administered with vehicle PBS (FIG. 15A) were different, in which the vascular walls were thickened and darkly stained, the vascular endothelial cells (Δ) were proliferated, and the pericytes (↑) were decreased remarkably; however, mice in the group administered with plasminogen had remarkably reduced pathological changes. It was found from quantitative analysis that compared with mice in the control group administered with vehicle PBS, those in the group administered with plasminogen had significantly reduced cell-free vascular length (FIG. 15C), and the statistical analysis results showed a significant difference. This indicated that plasminogen can significantly promote the repair of retinal injury of late diabetic mice.

Example 16

Plasminogen Promotes Dissolution of Microthrombi Caused by Diabetes Mellitus

Ten male db/db mice aged 24-25 weeks were randomly divided into two groups, five in the control group administered with vehicle PBS and five in the group administered with plasminogen, respectively. The day when the experiment began was recorded on Day 0, and the mice were weighed and grouped. From the second day of the experiment, plasminogen or PBS was administered to the mice for 15 consecutive days, and the day was recorded as Day 1. Mice in the group administered with plasminogen were injected with plasminogen at a dose of 2 mg/0.2 mL/mouse/day via the tail vein, and an equal volume of PBS was administered to mice in the control group administered with vehicle PBS. On day 16, blood was taken from the removed eyeballs, and the whole blood was left standing to obtain serum for detecting the D-dimer content in the blood.

Figure 16:
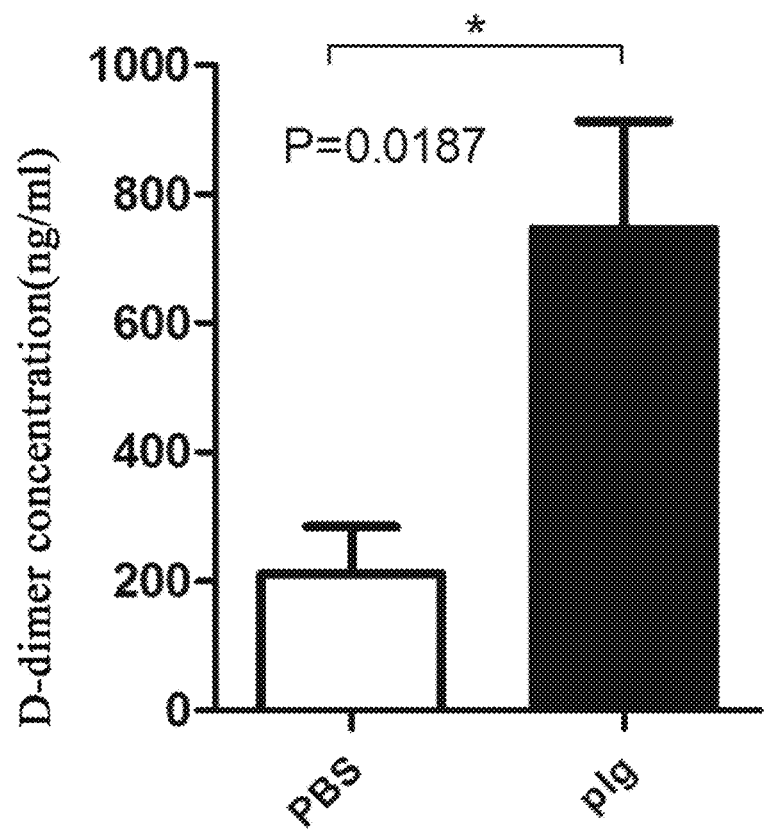
FIG. 16 shows the detection results of D-dimer content in serum after administration of plasminogen to 24-25-week-old diabetic mice for 15 consecutive days.

The results showed that the D-dimer content in the serum of mice in the group administered with plasminogen was significantly increased after 15 days of administration (FIG. 16), indicating that after administration of plasminogen, microthrombi caused by diabetes mellitus were significantly dissolved.

Example 17

Plasminogen Repairs Myocardial Injury in Late Diabetes Mellitus

Twenty-eight male db/db mice aged 24-25 weeks were randomly divided into two groups, twelve in the control group administered with vehicle PBS and sixteen in the group administered with plasminogen, respectively. The day when the experiment began was recorded on Day 0, and the mice were weighed and grouped. From the second day of the experiment, plasminogen or PBS was administered to the mice for 31 consecutive days, and the day was recorded as Day 1. Mice in the group administered with plasminogen were injected with plasminogen at a dose of 2 mg/0.2 mL/mouse/day via the tail vein, and an equal volume of PBS was administered to mice in the control group administered with vehicle PBS. On day 32, blood was taken from the removed eyeballs and centrifuged at 3500 r/min for 15-20 minutes, and the supernatant was used for the determination of cardiac troponin I concentration.

Figure 17:
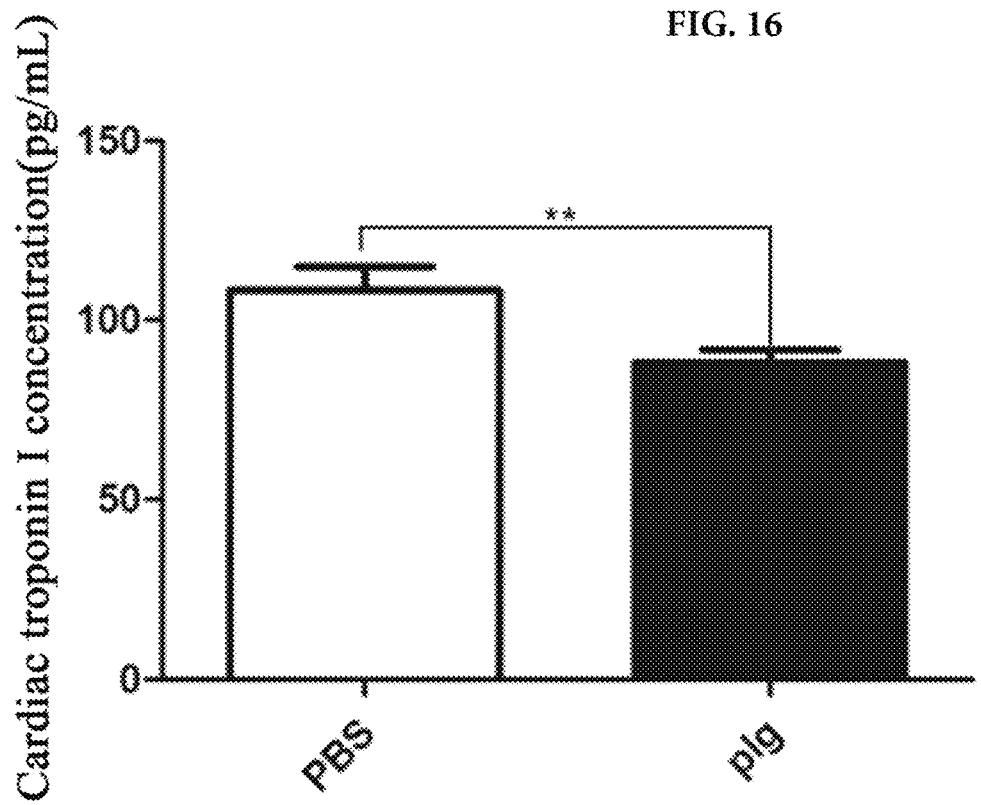
FIG. 17 shows the detection results of cardiac troponin I concentration in serum after administration of plasminogen to 24-25-week-old diabetic mice for 31 days.

Cardiac troponin I (CTNI) is an important marker of myocardial injury, and its serum concentration can reflect the extent of myocardial injury [38]. The results showed that the cardiac troponin I concentration in the group administered with plasminogen was significantly lower than that in the control group administered with vehicle PBS, and there was an extremely significant statistical difference (FIG. 17). This indicated that plasminogen can extremely significantly promote the repair of myocardial injury of late diabetic mice.

Example 18

Plasminogen Reduces Injury of the Kidneys of Late Diabetic Mice

Eight male db/db mice aged 24-25 weeks were randomly divided into two groups, four in the control group administered with vehicle PBS and four in the group administered with plasminogen, respectively. The day when the experiment began was recorded on Day 0, and the mice were weighed and grouped. From the second day of the experiment, plasminogen or PBS was administered to the mice for 31 consecutive days, and the day was recorded as Day 1. Mice in the group administered with plasminogen were injected with plasminogen at a dose of 2 mg/0.2 mL/mouse/day via the tail vein, and an equal volume of PBS was administered to mice in the control group administered with vehicle PBS. Detection of physiological indexes was finished on day 32, mice were sacrificed, and the kidneys were fixed in 10% neutral formalin fixative for 24 hours. The fixed kidney tissues were paraffin-embedded after dehydration with alcohol gradient and permeabilization with xylene. The thickness of the tissue sections was 5 μm. The sections were dewaxed and rehydrated and washed with water once. The sections were incubated with 3% hydrogen peroxide for 15 minutes and wash with water twice for 5 minutes each time. The sections were incubated with goat anti-mouse IgM (HRP) antibody (Abcam) for 1 hour at room temperature and washed with TBS twice for 5 minutes each time. The sections were developed with a DAB kit (Vector laboratories, Inc., USA). After washing with water three times, the sections were counterstained with hematoxylin for 30 seconds and flushed with running water for 5 minutes. After gradient dehydration, permeabilization and sealing, the sections were observed under a microscope at 400×.

IgM antibodies play an important role during the clearance of apoptotic and necrotic cells[39-41]. Therefore, its expression can reflect the injury of tissues and organs.

Figure 18:
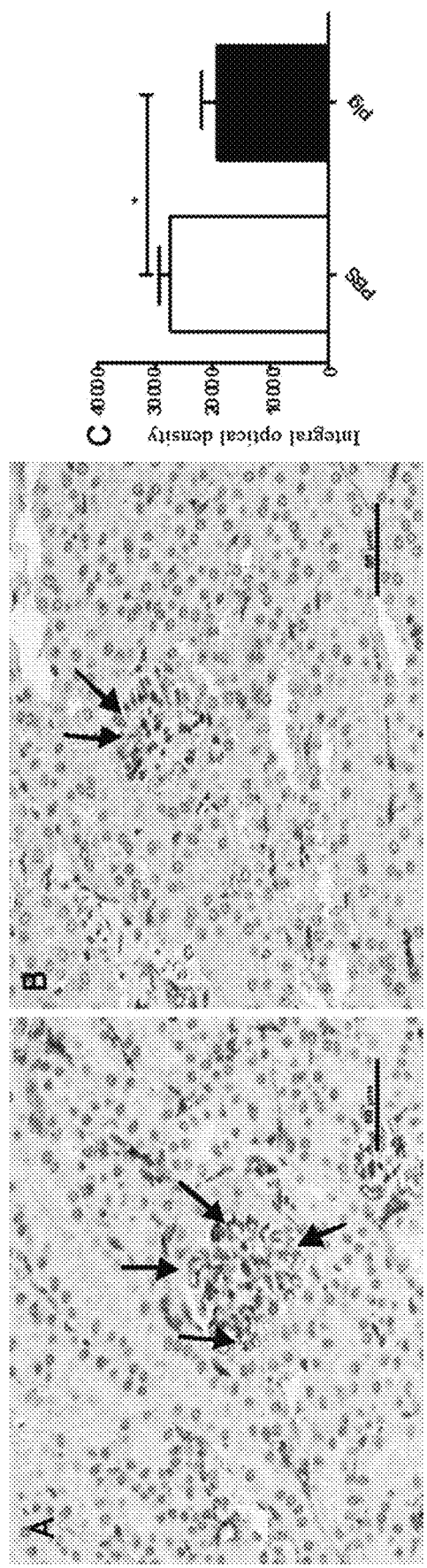
FIG. 18 shows the observed results of IgM immunostaining of the kidneys after administration of plasminogen to 24-25-week-old diabetic mice for 31 days.

The results showed that the positive staining of glomerular IgMs in mice in the group administered with plasminogen (FIG. 18B) was lighter than that of glomerular IgMs in mice in the control group administered with vehicle PBS (FIG. 18A), the range was also smaller, and the statistical analysis results were consistent with the observations (FIG. 18C), indicating that the glomerular injury is remarkably improved after injection of plasminogen, reflecting the significant repair function of plasminogen on the body's injury of diabetic mice.

Example 19

Plasminogen Promotes the Repair of Liver Injury of Diabetic Mice

Nine male db/db mice aged 25-28 weeks were randomly divided into two groups, three in the control group administered with vehicle PBS and six in the group administered with plasminogen, respectively. The day when the experiment began was recorded on Day 0, and the mice were weighed and grouped. From the second day of the experiment, plasminogen or PBS was administered to the mice for 31 consecutive days, and the day was recorded as Day 1. Mice in the group administered with plasminogen were injected with plasminogen at a dose of 2 mg/0.2 mL/mouse/day via the tail vein, and an equal volume of PBS was administered to mice in the control group administered with vehicle PBS. Whole blood was taken from the removed eyeballs 31 days after administration of plasminogen. After the serum was precipitated, it was centrifuged at 3500 r/min for 10 minutes at 4° C., and the supernatant was taken for detection. In this experiment, the content of alanine transaminase (ALT) in serum was detected by Reitman-Frankel colorimetry using an alanine transaminase detection kit (Nanjing Jiancheng Biological Engineering Research Institute, Catalog No. C009-2).

Figure 19:
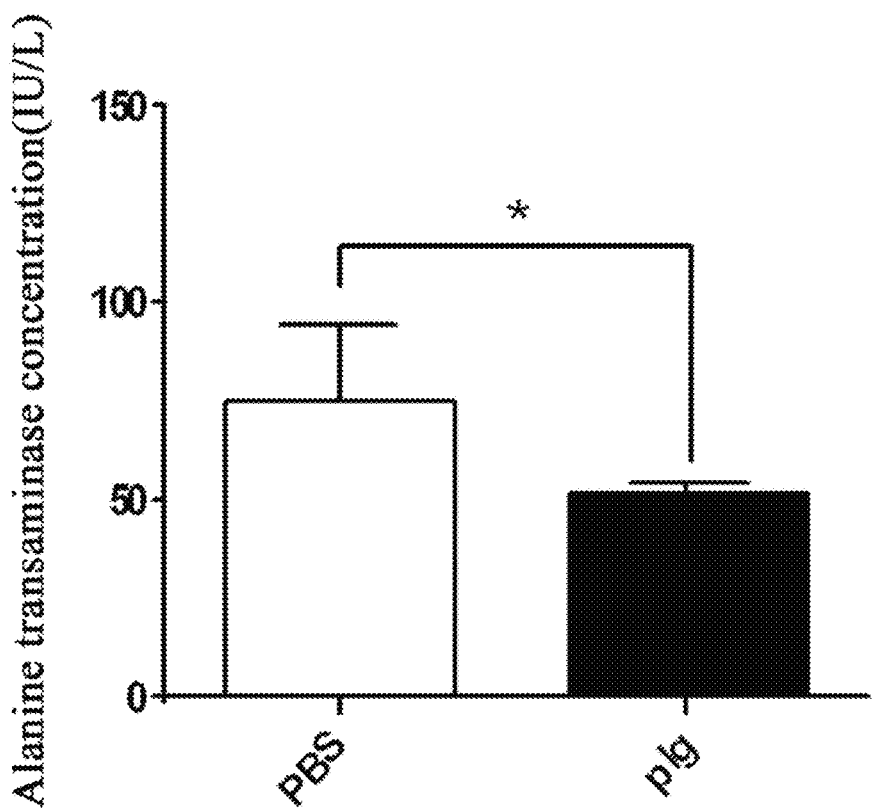
FIG. 19 shows the detection results of alanine transaminase (ALT) in serum after administration of plasminogen to 24-25-week-old diabetic mice for 31 days.

Alanine transaminase is an important index of liver health status[42,43], and the normal reference value interval of alanine transaminase is 9-50 U/L. The detection results showed that the ALT content in serum of mice in the control group administered with vehicle PBS was significantly higher than the normal physiological index, whereas the content in mice in the group administered with plasminogen had returned to normal levels in the body; and the content in mice in the group administered with plasminogen was significantly lower than that in mice in the control group administered with vehicle PBS, and there was a statistical difference (FIG. 19). This indicated that injection of plasminogen can effectively repair the liver injury in model mice with late diabetic diabetes.

Example 20

Plasminogen Promotes the Repair of the Ability of Diabetic Mice to Respond to Algesia Eight male db/db mice aged 8 weeks were randomly divided into two groups, four in the control group administered with vehicle PBS and four in the group administered with plasminogen, respectively. The day when the experiment began was recorded on Day 0, and the mice were weighed and grouped. From the second day of the experiment, plasminogen or PBS was administered to the mice for 8 consecutive days, and the day was recorded as Day 1. Mice in the group administered with plasminogen were injected with plasminogen at a dose of 2 mg/0.2 mL/mouse/day via the tail vein, and an equal volume of PBS was administered to mice in the control group administered with vehicle PBS. On days 0, 3, 6 and 9 after administration of plasminogen, animals were detected for their sensitivity to mechanical injury using Von-Frey filaments (Stoelting, USA). With 2.0 g force as the starting force, the left foot was first detected. If there were 2 paw withdrawals for 5 stimulations, it was positive; and if it was positive, the right foot was then stimulated with a smaller force. If it was negative, the right foot was stimulated with a larger force, the left and right feet were thus alternately stimulated for a total of 6 stimulations at a stimulation interval of 5 minutes, and then the 50% paw withdrawal threshold was calculated according to the method introduced in S. R. Chaplan et. al. (1994)[32].

The db/db mice developed into diabetic mice at around 4 weeks, had hyperalgesia at 8-12 weeks, and had hypoalgesia after 12 weeks[45,46]. Therefore, we selected 8-week-old db/db mice in the hyperalgesia period for the experiment.

Figure 20:
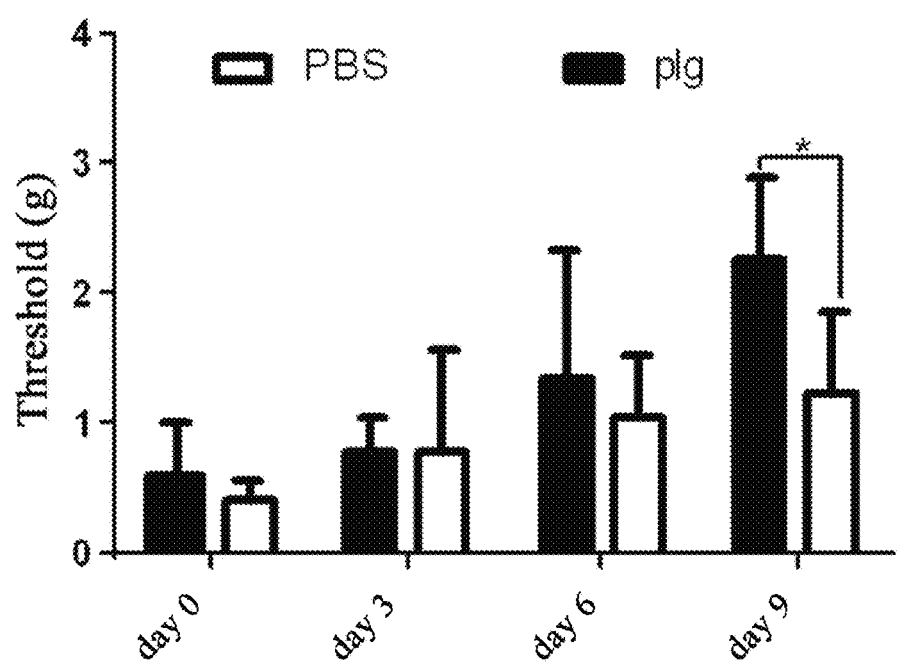
FIG. 20 shows changes in the ability to respond to mechanical allodynia after administration of plasminogen to 8-week-old diabetic mice for 9 days.

The results showed that compared with mice in the control group administered with vehicle PBS, those in the group administered with plasminogen had significantly increased algesia threshold (FIG. 20). This indicated that plasminogen can significantly reduce hyperalgesia (oversensitivity) caused by nerve injury in early diabetes mellitus.

REFERENCES

[1] Md. Shahidul Islam, 2013. Animal Models of Diabetic Neuropathy: Progress Since 1960s. Journal of Diabetes Research.

[2] Eizirik D L, Miani M, Cardozo A K. 2013. Signalling danger: Endoplasmic reticulum stress and the unfolded protein response in pancreatic islet inflammation. Diabetologia 56:234-241.

[3] Said G. Diabetic neuropathy. Nat Clin Pract Neurol 2007; 3:331-40.
[4] Vincent A M, Callaghan B C, Smith A L, Feldman E L. 2011. Diabetic neuropathy: Cellular mechanisms as therapeutic targets. Nat Rev Neurol 7:573-583.
[5] Alexander C M and Werb, Z. (1991). Extracellular matrix degradation. In Cell Biology of Extracellular Matrix, Hay E D, ed. (New York: Plenum Press), pp. 255-302.
[6] Werb, Z., Mainardi, C. L., Vater, C. A., and Harris, E. D., Jr. (1977). Endogenous activiation of latent collagenase by rheumatoid synovial cells. Evidence for a role of plasminogen activator. N. Engl. J. Med. 296, 1017-1023.
[7] He, C. S., Wilhelm, S. M., Pentland, A. P., Marmer, B. L., Grant, G A., Eisen, A. Z., and Goldberg, G I. (1989). Tissue cooperation in a proteolytic cascade activating human interstitial collagenase. Proc. Natl. Acad. Sci. U.S.A 86, 2632-2636.
[8] Stoppelli, M. P., Corti, A., Soffientini, A., Cassani, G., Blasi, F., and Assoian, R. K. (1985). Differentiation-enhanced binding of the amino-terminal fragment of human urokinase plasminogen activator to a specific receptor on U937 monocytes. Proc. Natl. Acad. Sci. U.S.A 82, 4939-4943.
[9] Vassalli, J. D., Baccino, D., and Belin, D. (1985). A cellular binding site for the Mr 55, 000 form of the human plasminogen activator, urokinase. J. Cell Biol. 100, 86-92.
[10] Wiman, B. and Wallen, P. (1975). Structural relationship between "glutamic acid" and "lysine" forms of human plasminogen and their interaction with the NH2-terminal activation peptide as studied by affinity chromatography. Eur. J. Biochem. 50, 489-494.
[11] Saksela, O. and Rifkin, D. B. (1988). Cell-associated plasminogen activation: regulation and physiological functions. Annu. Rev. Cell Biol. 4, 93-126.
[12] Raum, D., Marcus, D., Alper, C. A., Levey, R., Taylor, P. D., and Starzl, T. E. (1980). Synthesis of human plasminogen by the liver. Science 208, 1036-1037
[13] Wallen P (1980). Biochemistry of plasminogen. In Fibrinolysis, Kline D L and Reddy KKN, eds. (Florida: CRC
[14] Sottrup-Jensen, L., Zajdel, M., Claeys, H., Petersen, T. E., and Magnusson, S. (1975). Amino-acid sequence of activation cleavage site in plasminogen: homology with "pro" part of prothrombin. Proc. Natl. Acad. Sci. U.S.A 72, 2577-2581.
[15] Collen, D. and Lijnen, H. R. (1991). Basic and clinical aspects of fibrinolysis and thrombolysis. Blood 78, 3114-3124.
[16] Alexander, C. M. and Werb, Z. (1989). Proteinases and extracellular matrix remodeling. Curr. Opin. Cell Biol. 1, 974-982.
[17] Mignatti, P. and Rifkin, D. B. (1993). Biology and biochemistry of proteinases in tumor invasion. Physiol Rev. 73, 161-195.
[18] Collen, D. (2001). Ham-Wasserman lecture: role of the plasminogen system in fibrin-homeostasis and tissue remodeling. Hematology. (Am. Soc. Hematol. Educ. Program.) 1-9.
[19] Rifkin, D. B., Moscatelli, D., Bizik, J., Quarto, N., Blei, F., Dennis, P., Flaumenhaft, R., and Mignatti, P. (1990). Growth factor control of extracellular proteolysis. Cell Differ. Dev. 32, 313-318.
[20] Andreasen, P. A., Kjoller, L., Christensen, L., and Duffy, M. J. (1997). The urokinase-type plasminogen activator system in cancer metastasis: a review. Int. J. Cancer 72, 1-22.
[21] Rifkin, D. B., Mazzieri, R., Munger, J. S., Noguera, I., and Sung, J. (1999). Proteolytic control of growth factor availability. APMIS 107, 80-85.
[22] Cheng H T, Dauch J R, Hayes J M, Hong Y, Feldman E L. 2009. Nerve growth factor mediates mechanical allodynia in a mouse model of type 2 diabetes. J Neuropathol Exp Neurol 68:1229-1243.
[23] Ii M, Nishimura H, Kusano K F, Qin G, Yoon Y S, Wecker A, Asahara T, Losordo D W. 2005. Neuronal nitric oxide synthase mediates statin-induced restoration of vasa nervorum and reversal of diabetic neuropathy. Circulation 112:93-102.
[24] Kan M, Guo G, Singh B, Singh V, Zochodne D W. 2012. Glucagon-like peptide 1, insulin, sensory neurons, and diabetic neuropathy. J Neuropathol Exp Neurol 71:494-510.
[25] Sullivan K A, Hayes J M, Wiggin T D, Backus C, Su Oh S, Lentz S I, Brosius F 3rd, Feldman E L. 2007. Mouse models of diabetic neuropathy. Neurobiol Dis 28:276-285.
[26] Wang L, Chopp M, Szalad A, Liu Z, Bolz M, Alvarez F M, Lu M, Zhang L, Cui Y, Zhang R L, Zhang Z G 2011. Phosphodiesterase-5 is a therapeutic target for peripheral neuropathy in diabetic mice. Neuroscience 193: 399-410.
[27] Marder V J, Novokhatny V. Direct fibrinolytic agents: biochemical attributes, preclinical foundation and clinical potential [J]. Journal of Thrombosis and Haemostasis, 2010, 8(3): 433-444.
[28] Sottrup-Jensen L, Claeys H, Zajdel M, et al. The primary structure of human plasminogen: Isolation of two lysine-binding fragments and one "mini"-plasminogen (MW, 38, 000) by elastase-catalyzed-specific limited proteolysis [J]. Progress in chemical fibrinolysis and thrombolysis, 1978, 3: 191-209.
[29] Nagai N, Demarsin E, Van Hoef B, et al. Recombinant human microplasmin: production and potential therapeutic properties [J]. Journal of Thrombosis and Haemostasis, 2003, 1(2): 307-313.
[30] Hunt J A, Petteway Jr S R, Scuderi P, et al. Simplified recombinant plasmin: production and fu-nctional comparison of a novel thrombolytic molecule with plasma-derived plasmin [J]. Thromb Haemost, 2008, 100(3): 413-419.
[31] Yoon Choi a, Young Wook Yoon a, Heung Sik Na, Sun Ho Kim, Jin M O Chung. Behavioral signs of ongoing pain and cold allodynia in a rat model of neuropathic pain, Pain, 59 (1994) 369-376.
[32] S. R. Chaplan, et al. Quantitative assessment of tactile allodynia in the rat paw, Journal of Neuroscience Methods 53 (1994) 55-63.
[33] Jae Kyu Ryu, Mark A. Petersen, Sara G. Murray et al. Blood coagulation protein fibrinogen promotes autoimmunity and demyelination via chemokine release and antigen presentation. NATURE COMMUNICATIONS, 2015, 6:8164.
[34] Dimitrios Davalos, Katerina Akassoglou. Fibrinogen as a key regulator of inflammation in disease. Seminars in Immunopathology, 2012. 34(1):43-62.
[35] Valvi D, Mannino D M, Mullerova H, et al. Fibrinogen, chronic obstructive pulmonary disease (COPD) and outcomes in two United States cohorts. Int J Chron Obstruct Pulmon Dis 2012; 7:173-82.
[36] Moungjaroen J, Nimmannit U, Callery P S, Wang L, Azad N, Lipipun V, Chanvorachote P, Rojanasakul Y (2006). Reactive oxygen species mediate caspase activation and apoptosis induced by lipoic acid in human lung

[37] Wang L, Chanvorachote P, Toledo D, Stehlik C, Mercer R R, Castranova V, Rojanasakul Y (2008). Peroxide is a key mediator of Bcl-2 down-regulation and apoptosis induction by cisplatinin human lung cancer cells. Mol Pharmacol 73, 119-127.

[38] R. Langhorn and J. L. Willesen. Cardiac Troponins in Dogs and Cats. J Vet Intern Med 2016; 30:36-50.

[39] Zwart B, Ciurana C, Rensink I, Manoe R, Hack C E, et al. (2004) Complement activation by apoptotic cells occurs predominantly via IgM and is limited to late apoptotic (secondary necrotic) cells. Autoimmunity 37: 95-102.

[40] Zhang M, Takahashi K, Alicot E M, Vorup-Jensen T, Kessler B, et al. (2006) Activation of the lectin pathway by natural IgM in a model of ischemia/reperfusion injury. J Immunol 177: 4727-4734.

[41] Kim S J, Gershov D, Ma X, Brot N, Elkon K B (2002) I-PLA2 Activation during Apoptosis Promotes the Exposure of Membrane Lysophosphatidylcholine Leading to Binding by Natural Immunoglobulin M Antibodies and Complement Activation. The Journal of Experimental Medicine 196: 655-665.

[42] Karmen A, Wroblewski F Ladue J S (January 1955). Transaminase activity in human blood. The Journal of Clinical Investigation. 34 (1): 126-31

[43] Wang C S, Chang T T, Yao W J, Wang S T, Chou P (April 2012). Impact of increasing alanine aminotransferase levels within normal range on incident diabetes. Journal of the Formosan Medical Association Taiwan Yi Zhi. 111 (4): 201-8.

[44] Roy S, Sato T, Paryani G, Kao R: Downregulation of fibronectin overexpression reduces basement membrane thickening and vascular lesions in retinas of galactose-fed rats. Diabetes 2003, 52: 1229-1234.

[45] Cheng H T, Dauch J R, Hayes J M, Hong Y, Feldman E L. 2009. Nerve growthfactor mediates mechanical allodynia in a mouse model of type 2 diabetes. J Neuropathol Exp Neurol 68: 1229-1243.

[46] Ii M, Nishimura H, Kusano K F, Qin G; Yoon Y S, Wecker A, Asahara T, Losordo D W. 2005. Neuronal nitric oxide synthase mediatesstatin-induced restoration of vasa nervorum and reversal of diabetic neuropathy. Circulation 112:93-102.

The invention claimed is:

1. A method for repairing diabetic nerve injury, comprising administering an effective amount of plasminogen and an additional therapy and drug to a subject, wherein the plasminogen comprises a plasminogen active fragment comprising SEQ ID NO: 14 and has plasminogen activity, wherein the additional therapy comprises physical therapy selected from the group consisting of electromagnetic therapy and infrared therapy, and wherein the additional drug is selected from the group consisting of neurotrophic drugs, analgesics, drugs for the treatment of diabetes mellitus, anti-infective drugs, anti-hypertensive drugs, and anti-hyperlipidemic drugs.

2. The method of claim 1, wherein the plasminogen is administered intravenously.

3. The method of claim 1, wherein the plasminogen is selected from Glu-plasminogen, Lys-plasminogen, mini-plasminogen, micro-plasminogen, δ (delta)-plasminogen or any combination thereof.

4. The method of claim 1, wherein the plasminogen has at least 95% sequence identity with SEQ ID NOs: 2, 6, 8, 10, or 12, and still has the plasminogen activity.

5. A method for repairing diabetic nerve injury, comprising administering an effective amount of plasminogen and one or more additional drugs or therapies to a subject, wherein the plasminogen comprises a plasminogen active fragment comprising SEQ ID NO: 14 and has plasminogen activity, wherein the plasminogen is administered locally, and wherein the one or more additional drugs or therapies comprise neurotrophic drugs, analgesics, drugs for the treatment of diabetes mellitus, anti-infective drugs, anti-hypertensive drugs, anti-hyperlipidemic drugs, or physical therapies.

6. The method of claim 5, wherein the diabetic nerve injury is associated with a disorder comprising limb pain, hypoesthesia, numbness, burning, coldness, or diabetic neuropathic pain.

7. The method of claim 5, wherein the plasminogen has the amino acid sequence of SEQ ID NO: 6.

8. The method of claim 5, wherein the plasminogen has at least 80% sequence identity with SEQ ID NO: 8, and still has the plasminogen activity.

9. The method of claim 5, wherein the plasminogen has the amino acid sequence of SEQ ID NO: 8.

10. The method of claim 5, wherein the plasminogen has at least 80% sequence identity with SEQ ID NO: 10, and still has the plasminogen activity.

11. The method of claim 5, wherein the plasminogen has the amino acid sequence of SEQ ID NO: 10.

12. The method of claim 5, wherein the plasminogen has the amino acid sequence of SEQ ID NO: 12.

13. The method of claim 5, wherein the plasminogen has at least 95% sequence identity with SEQ ID NO: 12, and still has the plasminogen activity.

14. The method of claim 5, wherein the plasminogen has the amino acid sequence of SEQ ID NO: 2.

15. The method of claim 5, wherein the diabetic nerve injury is associated with diabetic neuropathic pain, and wherein the diabetic neuropathic pain comprises spontaneous pain, hypoalgesia or hyperalgesia induced by diabetic complications.

16. The method of claim 5, wherein the plasminogen has at least 80% sequence identity to SEQ ID NO: 2.

17. The method of claim 5, wherein the plasminogen has at least 90% sequence identity to SEQ ID NO: 2.

18. The method of claim 5, wherein the diabetic nerve injury comprises nerve tissue injury or neuroinflammation.

19. The method of claim 5, wherein the plasminogen has at least 80% identity with SEQ ID NO: 6, and still has the plasminogen activity.

20. The method of claim 5, wherein the plasminogen is selected from Glu-plasminogen, Lys-plasminogen, mini-plasminogen, micro-plasminogen, δ (delta)-plasminogen or any combination thereof.

\* \* \* \* \*

SEQUENCE LISTING

```
<160> NUMBER OF SEQ ID NOS: 14

<210> SEQ ID NO 1
<211> LENGTH: 2376
<212> TYPE: DNA
<213> ORGANISM: Artificial Sequence
<220> FEATURE:
<223> OTHER INFORMATION: nucleotide sequence coding for the natural
      human plasminogen (Glu-PLG or Glu-plasminogen) without the signal
      peptide

<400> SEQUENCE: 1
gagcctctgg atgactatgt gaatacccag ggggcttcac tgttcagtgt cactaagaag      60
cagctgggag caggaagtat agaagaatgt gcagcaaaat gtgaggagga cgaagaattc     120
acctgcaggg cattccaata tcacagtaaa gagcaacaat gtgtgataat ggctgaaaac     180
aggaagtcct ccataatcat taggatgaga gatgtagttt tatttgaaaa gaaagtgtat     240
ctctcagagt gcaagactgg gaatggaaag aactacagag ggacgatgtc caaaacaaaa     300
aatggcatca cctgtcaaaa atggagttcc acttctcccc acagacctag attctcacct     360
gctacacacc cctcagaggg actggaggag aactactgca ggaatccaga caacgatccg     420
caggggccct ggtgctatac tactgatcca gaaaagagat atgactactg cgacattctt     480
gagtgtgaag aggaatgtat gcattgcagt ggagaaaact atgacggcaa aatttccaag     540
accatgtctg gactggaatg ccaggcctgg gactctcaga gcccacacgc tcatggatac     600
attccttcca aatttccaaa caagaacctg aagaagaatt actgtcgtaa ccccgatagg     660
gagctgcggc cttggtgttt caccaccgac cccaacaagc gctgggaact tgtgacatc      720 ccccgctgca acacctcc accatcttct ggtcccacct accagtgtct gaagggaaca      780
ggtgaaaact atcgcgggaa tgtggctgtt accgtgtccg ggcacacctg tcagcactgg     840
agtgcacaga cccctcacac acataacagg acaccagaaa acttccctg caaaaatttg     900 gatgaaaact actgccgcaa tcctgacgga aaagggccc catggtgcca tacaaccaac    960
agccaagtgc ggtgggagta ctgtaagata ccgtcctgtg actcctcccc agtatccacg   1020
gaacaattgg ctcccacagc accacctgag ctaacccctg tggtccagga ctgctaccat   1080
```

```
ggtgatggac agagctaccg aggcacatcc tccaccacca ccacaggaaa gaagtgtcag    1140
tcttggtcat ctatgacacc acaccggcac agaagaccc cagaaaacta cccaaatgct    1200
ggcctgacaa tgaactactg caggaatcca gatgccgata aggcccctg tgttttacc     1260 acagaccca gcgtcaggtg ggagtactgc aacctgaaaa atgctcagg aacagaagcg     1320 agtgttgtag cacctccgcc tgttgtcctg cttccagatg tagagactcc ttccgaagaa    1380
gactgtatgt ttgggaatgg aaaggatac cgaggcaaga gggcgaccac tgttactggg    1440
acgccatgcc aggactgggc tgcccaggag ccccatagac acagcatttt cactccagag    1500
acaaatccac gggcgggtct ggaaaaaaat tactgccgta accctgatgg tgatgtaggt    1560
ggtccctggt gctacacgac aaatccaaga aaactttacg actactgtga tgtccctcag    1620
tgtgcggccc cttcatttga ttgtgggaag cctcaagtgg agccgaagaa atgtcctgga    1680
agggttgtag gggggtgtgt ggcccaccca cattcctggc cctggcaagt cagtcttaga    1740
acaaggtttg gaatgcactt ctgtggaggc accttgatat ccccagagtg ggtgttgact    1800
gctgcccact gcttggagaa gtccccaagg ccttcatcct acaaggtcat cctgggtgca    1860
caccaagaag tgaatctcga accgcatgtt caggaaatag aagtgtctag gctgttcttg    1920
gagcccacac gaaaagatat tgccttgcta aagctaagca gtcctgccgt catcactgac    1980
aaagtaatcc cagcttgtct gccatcccca aattatgtgg tcgctgaccg gaccgaatgt    2040
ttcatcactg gctggggaga aacccaaggt acttttggag ctggccttct caaggaagcc    2100
cagctccctg tgattgagaa taaagtgtgc aatcgctatg agtttctgaa tggaagagtc    2160
caatccaccg aactctgtgc tgggcatttg gccggaggca ctgacagttg ccaggggtgac   2220 agtggaggtc ctctggtttg cttcgagaag gacaaataca ttttacaagg agtcacttct    2280
tggggtcttg gctgtgcacg ccccaataag cctggtgtct atgttcgtgt ttcaaggttt    2340
gttacttgga ttgagggagt gatgagaaat aattaa                              2376
```

<210> SEQ ID NO 2
<211> LENGTH: 791
<212> TYPE: PRT
<213> ORGANISM: Artificial Sequence
<220> FEATURE:
<223> OTHER INFORMATION: amino acid sequence of the natural human
      plasminogen (Glu-PLG or Glu-plasminogen) without the signal
      peptide

<400> SEQUENCE: 2

Glu Pro Leu Asp Asp Tyr Val Asn Thr Gln Gly Ala Ser Leu Phe Ser
1               5                   10                  15

Val Thr Lys Lys Gln Leu Gly Ala Gly Ser Ile Glu Glu Cys Ala Ala
            20                  25                  30

Lys Cys Glu Glu Asp Glu Glu Phe Thr Cys Arg Ala Phe Gln Tyr His
        35                  40                  45

Ser Lys Glu Gln Gln Cys Val Ile Met Ala Glu Asn Arg Lys Ser Ser
    50                  55                  60

Ile Ile Ile Arg Met Arg Asp Val Val Leu Phe Glu Lys Lys Val Tyr
65                  70                  75                  80

Leu Ser Glu Cys Lys Thr Gly Asn Gly Lys Asn Tyr Arg Gly Thr Met
                85                  90                  95

Ser Lys Thr Lys Asn Gly Ile Thr Cys Gln Lys Trp Ser Ser Thr Ser
            100                 105                 110

Pro His Arg Pro Arg Phe Ser Pro Ala Thr His Pro Ser Glu Gly Leu

```
          115                 120                 125
Glu Glu Asn Tyr Cys Arg Asn Pro Asp Asn Pro Gln Gly Pro Trp
    130                 135                 140

Cys Tyr Thr Thr Asp Pro Glu Lys Arg Tyr Asp Tyr Cys Asp Ile Leu
145                 150                 155                 160

Glu Cys Glu Glu Glu Cys Met His Cys Ser Gly Glu Asn Tyr Asp Gly
                165                 170                 175

Lys Ile Ser Lys Thr Met Ser Gly Leu Glu Cys Gln Ala Trp Asp Ser
                180                 185                 190

Gln Ser Pro His Ala His Gly Tyr Ile Pro Ser Lys Phe Pro Asn Lys
                195                 200                 205

Asn Leu Lys Lys Asn Tyr Cys Arg Asn Pro Asp Arg Glu Leu Arg Pro
        210                 215                 220

Trp Cys Phe Thr Thr Asp Pro Asn Lys Arg Trp Glu Leu Cys Asp Ile
225                 230                 235                 240

Pro Arg Cys Thr Thr Pro Pro Ser Ser Gly Pro Thr Tyr Gln Cys
                245                 250                 255

Leu Lys Gly Thr Gly Glu Asn Tyr Arg Gly Asn Val Ala Val Thr Val
                260                 265                 270

Ser Gly His Thr Cys Gln His Trp Ser Ala Gln Thr Pro His Thr His
        275                 280                 285

Asn Arg Thr Pro Glu Asn Phe Pro Cys Lys Asn Leu Asp Glu Asn Tyr
        290                 295                 300

Cys Arg Asn Pro Asp Gly Lys Arg Ala Pro Trp Cys His Thr Thr Asn
305                 310                 315                 320

Ser Gln Val Arg Trp Glu Tyr Cys Lys Ile Pro Ser Cys Asp Ser Ser
                325                 330                 335

Pro Val Ser Thr Glu Gln Leu Ala Pro Thr Ala Pro Pro Glu Leu Thr
                340                 345                 350

Pro Val Val Gln Asp Cys Tyr His Gly Asp Gly Gln Ser Tyr Arg Gly
                355                 360                 365

Thr Ser Ser Thr Thr Thr Thr Gly Lys Lys Cys Gln Ser Trp Ser Ser
        370                 375                 380

Met Thr Pro His Arg His Gln Lys Thr Pro Glu Asn Tyr Pro Asn Ala
385                 390                 395                 400

Gly Leu Thr Met Asn Tyr Cys Arg Asn Pro Asp Ala Asp Lys Gly Pro
                405                 410                 415

Trp Cys Phe Thr Thr Asp Pro Ser Val Arg Trp Glu Tyr Cys Asn Leu
                420                 425                 430

Lys Lys Cys Ser Gly Thr Glu Ala Ser Val Val Ala Pro Pro Pro Val
        435                 440                 445

Val Leu Leu Pro Asp Val Glu Thr Pro Ser Glu Glu Asp Cys Met Phe
        450                 455                 460

Gly Asn Gly Lys Gly Tyr Arg Gly Lys Arg Ala Thr Thr Val Thr Gly
465                 470                 475                 480

Thr Pro Cys Gln Asp Trp Ala Ala Gln Glu Pro His Arg His Ser Ile
                485                 490                 495

Phe Thr Pro Glu Thr Asn Pro Arg Ala Gly Leu Glu Lys Asn Tyr Cys
                500                 505                 510

Arg Asn Pro Asp Gly Asp Val Gly Gly Pro Trp Cys Tyr Thr Thr Asn
                515                 520                 525

Pro Arg Lys Leu Tyr Asp Tyr Cys Asp Val Pro Gln Cys Ala Ala Pro
        530                 535                 540
```

```
Ser Phe Asp Cys Gly Lys Pro Gln Val Glu Pro Lys Lys Cys Pro Gly
545                 550                 555                 560

Arg Val Val Gly Gly Cys Val Ala His Pro His Ser Trp Pro Trp Gln
                565                 570                 575

Val Ser Leu Arg Thr Arg Phe Gly Met His Phe Cys Gly Gly Thr Leu
            580                 585                 590

Ile Ser Pro Glu Trp Val Leu Thr Ala Ala His Cys Leu Glu Lys Ser
        595                 600                 605

Pro Arg Pro Ser Ser Tyr Lys Val Ile Leu Gly Ala His Gln Glu Val
610                 615                 620

Asn Leu Glu Pro His Val Gln Glu Ile Glu Val Ser Arg Leu Phe Leu
625                 630                 635                 640

Glu Pro Thr Arg Lys Asp Ile Ala Leu Leu Lys Leu Ser Ser Pro Ala
                645                 650                 655

Val Ile Thr Asp Lys Val Ile Pro Ala Cys Leu Pro Ser Pro Asn Tyr
            660                 665                 670

Val Val Ala Asp Arg Thr Glu Cys Phe Ile Thr Gly Trp Gly Glu Thr
        675                 680                 685

Gln Gly Thr Phe Gly Ala Gly Leu Leu Lys Glu Ala Gln Leu Pro Val
690                 695                 700

Ile Glu Asn Lys Val Cys Asn Arg Tyr Glu Phe Leu Asn Gly Arg Val
705                 710                 715                 720

Gln Ser Thr Glu Leu Cys Ala Gly His Leu Ala Gly Gly Thr Asp Ser
                725                 730                 735

Cys Gln Gly Asp Ser Gly Gly Pro Leu Val Cys Phe Glu Lys Asp Lys
            740                 745                 750

Tyr Ile Leu Gln Gly Val Thr Ser Trp Gly Leu Gly Cys Ala Arg Pro
        755                 760                 765

Asn Lys Pro Gly Val Tyr Val Arg Val Ser Arg Phe Val Thr Trp Ile
    770                 775                 780

Glu Gly Val Met Arg Asn Asn
785                 790

<210> SEQ ID NO 3
<211> LENGTH: 2433
<212> TYPE: DNA
<213> ORGANISM: Artificial Sequence
<220> FEATURE:
<223> OTHER INFORMATION: nucleotide sequence coding for the natural
      plasminogen (from swiss prot) with the signal peptide

<400> SEQUENCE: 3
atggaacata aggaagtggt tcttctactt cttttatttc tgaaatcagg tcaaggagag     60
cctctggatg actatgtgaa tacccagggg gcttcactgt tcagtgtcac taagaagcag    120 ctggagcag gaagtataga agaatgtgca gcaaaatgtg aggaggacga agaattcacc     180
tgcagggcat ccaatatca cagtaaagag caacaatgtg tgataatggc tgaaaacagg    240
aagtcctcca taatcattag gatgagagat gtagttttat ttgaaaagaa agtgtatctc    300
tcagagtgca agactgggaa tggaaagaac tacagaggga cgatgtccaa aacaaaaaat    360
ggcatcacct gtcaaaaatg gagttccact tctccccaca gacctagatt ctcacctgct    420
acacacccct cagagggact ggaggagaac tactgcagga atccagacaa cgatccgcag    480 gggcccggt gctatactac tgatccagaa aagagatatg actactgcga cattcttgag    540
tgtgaagagg aatgtatgca ttgcagtgga gaaaactatg acggcaaaat ttccaagacc    600
```

```
atgtctggac tggaatgcca ggcctgggac tctcagagcc cacacgctca tggatacatt    660
ccttccaaat ttccaaacaa gaacctgaag aagaattact gtcgtaaccc cgatagggag    720
ctgcggcctt ggtgtttcac caccgacccc aacaagcgct gggaactttg tgacatcccc    780
cgctgcacaa cacctccacc atcttctggt cccacctacc agtgtctgaa gggaacaggt    840
gaaaactatc gcgggaatgt ggctgttacc gtgtccgggc acacctgtca gcactggagt    900
gcacagaccc ctcacacaca taacaggaca ccagaaaact ccccctgcaa aaatttggat    960
gaaaactact gccgcaatcc tgacggaaaa agggcccat ggtgccatac aaccaacagc   1020
caagtgcggt gggagtactg taagataccg tcctgtgact cctccccagt atccacggaa   1080
caattggctc ccacagcacc acctgagcta acccctgtgg tccaggactg ctaccatggt   1140
gatggacaga gctaccgagg cacatcctcc accaccacca caggaaagaa gtgtcagtct   1200
tggtcatcta tgacaccaca ccggcaccag aagacccag aaaactaccc aaatgctggc   1260
ctgacaatga actactgcag gaatccagat gccgataaag gccctggtg ttttaccaca   1320 gaccccagcg tcaggtggga gtactgcaac ctgaaaaaat gctcaggaac agaagcgagt   1380
gttgtagcac ctccgcctgt tgtcctgctt ccagatgtag agactccttc gaagaagac   1440 tgtatgtttg ggatgggaa aggataccga ggcaagaggg cgaccactgt tactgggacg   1500
ccatgccagg actgggctgc ccaggagccc catagacaca gcattttcac tccagagaca   1560
aatccacggg cgggtctgga aaaaaattac tgccgtaacc ctgatggtga tgtaggtggt   1620
ccctggtgct acacgacaaa tccaagaaaa ctttacgact actgtgatgt ccctcagtgt   1680
gcggcccctt catttgattg tgggaagcct caagtggagc cgaagaaatg tcctggaagg   1740
gttgtagggg ggtgtgtggc ccacccacat tcctggccct ggcaagtcag tcttagaaca   1800
aggtttggaa tgcacttctg tggaggcacc ttgatatccc cagagtgggt gttgactgct   1860
gcccactgct tggagaagtc cccaaggcct tcatcctaca aggtcatcct gggtgcacac   1920
caagaagtga atctcgaacc gcatgttcag gaaatagaag tgtctaggct gttcttggag   1980
cccacacgaa aagatattgc cttgctaaag ctaagcagtc ctgccgtcat cactgacaaa   2040
gtaatcccag cttgtctgcc atccccaaat tatgtggtcg ctgaccggac cgaatgtttc   2100
atcactggct ggggagaaac ccaaggtact tttggagctg gccttctcaa ggaagcccag   2160
ctccctgtga ttgagaataa agtgtgcaat cgctatgagt ttctgaatgg aagagtccaa   2220
tccaccgaac tctgtgctgg gcatttggcc ggaggcactg acagttgcca gggtgacagt   2280
ggaggtcctc tggtttgctt cgagaaggac aaatacattt tacaaggagt cacttcttgg   2340
ggtcttggct gtgcacgccc caataagcct ggtgtctatg ttcgtgtttc aaggtttgtt   2400
acttggattg agggagtgat gagaaataat taa                                2433
```

<210> SEQ ID NO 4
<211> LENGTH: 810
<212> TYPE: PRT
<213> ORGANISM: Artificial Sequence
<220> FEATURE:
<223> OTHER INFORMATION: amino acid sequence coding for the natural
      plasminogen (from swiss prot) with the signal peptide

<400> SEQUENCE: 4

Met Glu His Lys Glu Val Val Leu Leu Leu Leu Phe Leu Lys Ser
1               5                   10                  15

Gly Gln Gly Glu Pro Leu Asp Asp Tyr Val Asn Thr Gln Gly Ala Ser
            20                  25                  30

```
Leu Phe Ser Val Thr Lys Lys Gln Leu Gly Ala Gly Ser Ile Glu Glu
             35                  40                  45

Cys Ala Ala Lys Cys Glu Glu Asp Glu Glu Phe Thr Cys Arg Ala Phe
     50                  55                  60

Gln Tyr His Ser Lys Glu Gln Gln Cys Val Ile Met Ala Glu Asn Arg
 65                  70                  75                  80

Lys Ser Ser Ile Ile Ile Arg Met Arg Asp Val Val Leu Phe Glu Lys
                 85                  90                  95

Lys Val Tyr Leu Ser Glu Cys Lys Thr Gly Asn Gly Lys Asn Tyr Arg
             100                 105                 110

Gly Thr Met Ser Lys Thr Lys Asn Gly Ile Thr Cys Gln Lys Trp Ser
             115                 120                 125

Ser Thr Ser Pro His Arg Pro Arg Phe Ser Pro Ala Thr His Pro Ser
             130                 135                 140

Glu Gly Leu Glu Glu Asn Tyr Cys Arg Asn Pro Asp Asn Asp Pro Gln
145                 150                 155                 160

Gly Pro Trp Cys Tyr Thr Thr Asp Pro Glu Lys Arg Tyr Asp Tyr Cys
             165                 170                 175

Asp Ile Leu Glu Cys Glu Glu Cys Met His Cys Ser Gly Glu Asn
             180                 185                 190

Tyr Asp Gly Lys Ile Ser Lys Thr Met Ser Gly Leu Glu Cys Gln Ala
             195                 200                 205

Trp Asp Ser Gln Ser Pro His Ala His Gly Tyr Ile Pro Ser Lys Phe
             210                 215                 220

Pro Asn Lys Asn Leu Lys Lys Asn Tyr Cys Arg Asn Pro Asp Arg Glu
225                 230                 235                 240

Leu Arg Pro Trp Cys Phe Thr Thr Asp Pro Asn Lys Arg Trp Glu Leu
             245                 250                 255

Cys Asp Ile Pro Arg Cys Thr Thr Pro Pro Ser Ser Gly Pro Thr
             260                 265                 270

Tyr Gln Cys Leu Lys Gly Thr Gly Glu Asn Tyr Arg Gly Asn Val Ala
             275                 280                 285

Val Thr Val Ser Gly His Thr Cys Gln His Trp Ser Ala Gln Thr Pro
             290                 295                 300

His Thr His Asn Arg Thr Pro Glu Asn Phe Pro Cys Lys Asn Leu Asp
305                 310                 315                 320

Glu Asn Tyr Cys Arg Asn Pro Asp Gly Lys Arg Ala Pro Trp Cys His
                 325                 330                 335

Thr Thr Asn Ser Gln Val Arg Trp Glu Tyr Cys Lys Ile Pro Ser Cys
             340                 345                 350

Asp Ser Ser Pro Val Ser Thr Glu Gln Leu Ala Pro Thr Ala Pro Pro
             355                 360                 365

Glu Leu Thr Pro Val Val Gln Asp Cys Tyr His Gly Asp Gly Gln Ser
             370                 375                 380

Tyr Arg Gly Thr Ser Ser Thr Thr Thr Thr Gly Lys Lys Cys Gln Ser
385                 390                 395                 400

Trp Ser Ser Met Thr Pro His Arg His Gln Lys Thr Pro Glu Asn Tyr
             405                 410                 415

Pro Asn Ala Gly Leu Thr Met Asn Tyr Cys Arg Asn Pro Asp Ala Asp
             420                 425                 430

Lys Gly Pro Trp Cys Phe Thr Thr Asp Pro Ser Val Arg Trp Glu Tyr
             435                 440                 445
```

```
Cys Asn Leu Lys Lys Cys Ser Gly Thr Glu Ala Ser Val Val Ala Pro
        450                 455                 460
Pro Pro Val Val Leu Leu Pro Asp Val Glu Thr Pro Ser Glu Glu Asp
465                 470                 475                 480
Cys Met Phe Gly Asn Gly Lys Gly Tyr Arg Gly Lys Arg Ala Thr Thr
                    485                 490                 495
Val Thr Gly Thr Pro Cys Gln Asp Trp Ala Ala Gln Glu Pro His Arg
                500                 505                 510
His Ser Ile Phe Thr Pro Glu Thr Asn Pro Arg Ala Gly Leu Glu Lys
            515                 520                 525
Asn Tyr Cys Arg Asn Pro Asp Gly Asp Val Gly Gly Pro Trp Cys Tyr
530                 535                 540
Thr Thr Asn Pro Arg Lys Leu Tyr Asp Tyr Cys Asp Val Pro Gln Cys
545                 550                 555                 560
Ala Ala Pro Ser Phe Asp Cys Gly Lys Pro Gln Val Glu Pro Lys Lys
                565                 570                 575
Cys Pro Gly Arg Val Val Gly Gly Cys Val Ala His Pro His Ser Trp
            580                 585                 590
Pro Trp Gln Val Ser Leu Arg Thr Arg Phe Gly Met His Phe Cys Gly
            595                 600                 605
Gly Thr Leu Ile Ser Pro Glu Trp Val Leu Thr Ala Ala His Cys Leu
610                 615                 620
Glu Lys Ser Pro Arg Pro Ser Ser Tyr Lys Val Ile Leu Gly Ala His
625                 630                 635                 640
Gln Glu Val Asn Leu Glu Pro His Val Gln Glu Ile Glu Val Ser Arg
                645                 650                 655
Leu Phe Leu Glu Pro Thr Arg Lys Asp Ile Ala Leu Leu Lys Leu Ser
            660                 665                 670
Ser Pro Ala Val Ile Thr Asp Lys Val Ile Pro Ala Cys Leu Pro Ser
            675                 680                 685
Pro Asn Tyr Val Val Ala Asp Arg Thr Glu Cys Phe Ile Thr Gly Trp
690                 695                 700
Gly Glu Thr Gln Gly Thr Phe Gly Ala Gly Leu Leu Lys Glu Ala Gln
705                 710                 715                 720
Leu Pro Val Ile Glu Asn Lys Val Cys Asn Arg Tyr Glu Phe Leu Asn
                725                 730                 735
Gly Arg Val Gln Ser Thr Glu Leu Cys Ala Gly His Leu Ala Gly Gly
            740                 745                 750
Thr Asp Ser Cys Gln Gly Asp Ser Gly Gly Pro Leu Val Cys Phe Glu
            755                 760                 765
Lys Asp Lys Tyr Ile Leu Gln Gly Val Thr Ser Trp Gly Leu Gly Cys
770                 775                 780
Ala Arg Pro Asn Lys Pro Gly Val Tyr Val Arg Val Ser Arg Phe Val
785                 790                 795                 800
Thr Trp Ile Glu Gly Val Met Arg Asn Asn
                805                 810

<210> SEQ ID NO 5
<211> LENGTH: 2145
<212> TYPE: DNA
<213> ORGANISM: Artificial Sequence
<220> FEATURE:
<223> OTHER INFORMATION: nucleotide sequence coding for LYS77-PLG or
      Lys-plasminogen

<400> SEQUENCE: 5
```

```
aaagtgtatc tctcagagtg caagactggg aatggaaaga actacagagg gacgatgtcc    60
aaaacaaaaa atggcatcac ctgtcaaaaa tggagttcca cttctcccca cagacctaga   120
ttctcacctg ctacacaccc ctcagaggga ctggaggaga actactgcag gaatccagac   180
aacgatccgc aggggccctg gtgctatact actgatccag aaaagagata tgactactgc   240
gacattcttg agtgtgaaga ggaatgtatg cattgcagtg gagaaaacta tgacggcaaa   300
atttccaaga ccatgtctgg actggaatgc caggcctggg actctcagag cccacacgct   360
catggataca ttccttccaa atttccaaac aagaacctga gaagaattac tgtcgtaac    420
cccgataggg agctgcggcc ttggtgtttc accaccgacc ccaacaagcg ctgggaactt   480
tgtgacatcc cccgctgcac aacacctcca ccatcttctg gtcccaccta ccagtgtctg   540
aagggaacag gtgaaaacta tcgcgggaat gtggctgtta ccgtgtccgg cacacctgt    600
cagcactgga gtgcacagac ccctcacaca cataacagga caccagaaaa cttcccctgc   660
aaaaatttgg atgaaaacta ctgccgcaat cctgacggaa aaagggcccc atggtgccat   720
acaaccaaca gccaagtgcg gtgggagtac tgtaagatac cgtcctgtga ctcctcccca   780
gtatccacgg aacaattggc tcccacagca ccacctgagc taaccccctgt ggtccaggac   840
tgctaccatg gtgatggaca gagctaccga ggcacatcct ccaccaccac cacaggaaag   900
aagtgtcagt cttggtcatc tatgacacca caccggcacc agaagacccc agaaaactac   960
ccaaatgctg gcctgacaat gaactactgc aggaatccag atgccgataa aggcccctgg  1020
tgttttacca cagaccccag cgtcaggtgg gagtactgca acctgaaaaa atgctcagga  1080
acagaagcga gtgttgtagc acctccgcct gttgtcctgc ttccagatgt agagactcct  1140
tccgaagaag actgtatgtt tgggaatggg aaaggatacc gaggcaagag ggcgaccact  1200
gttactggga cgccatgcca ggactgggct gcccaggagc ccatagaca cagcattttc  1260
actccagaga caaatccacg ggcgggtctg gaaaaaaatt actgccgtaa ccctgatggt  1320
gatgtaggtg gtccctggtg ctacacgaca aatccaagaa aactttacga ctactgtgat  1380
gtccctcagt gtgcggcccc ttcatttgat tgtgggaagc ctcaagtgga gccgaagaaa  1440
tgtcctggaa gggttgtagg ggggtgtgtg gcccacccac attcctggcc ctggcaagtc  1500
agtcttagaa caaggtttgg aatgcacttc tgtggaggca ccttgatatc cccagagtgg  1560
gtgttgactg ctgcccactg cttggagaag tccccaaggc cttcatccta caaggtcatc  1620
ctgggtgcac accaagaagt gaatctcgaa ccgcatgttc aggaaataga agtgtctagg  1680
ctgttcttgg agcccacacg aaaagatatt gccttgctaa agctaagcag tcctgccgtc  1740
atcactgaca agtaatccc agcttgtctg ccatccccaa attatgtggt cgctgaccgg  1800
accgaatgtt tcatcactgg ctgggagaa acccaaggta cttttggagc tggccttctc  1860
aaggaagccc agctccctgt gattgagaat aaagtgtgca atcgctatga gtttctgaat  1920
ggaagagtcc aatccaccga actctgtgct gggcatttgg ccggaggcac tgacagttgc  1980
cagggtgaca gtggaggtcc tctggtttgc ttcgagaagg acaaatacat tttacaagga  2040
gtcacttctt ggggtcttgg ctgtgcacgc cccaataagc ctggtgtcta tgttcgtgtt  2100
tcaaggtttg ttacttggat tgagggagtg atgagaaata attaa              2145
```

<210> SEQ ID NO 6
<211> LENGTH: 714
<212> TYPE: PRT
<213> ORGANISM: Artificial Sequence
<220> FEATURE:

<223> OTHER INFORMATION: amino acid sequence of LYS77-PLG or Lys-plasminogen

<400> SEQUENCE: 6

```
Lys Val Tyr Leu Ser Glu Cys Lys Thr Gly Asn Gly Lys Asn Tyr Arg
1               5                   10                  15

Gly Thr Met Ser Lys Thr Lys Asn Gly Ile Thr Cys Gln Lys Trp Ser
            20                  25                  30

Ser Thr Ser Pro His Arg Pro Arg Phe Ser Pro Ala Thr His Pro Ser
        35                  40                  45

Glu Gly Leu Glu Glu Asn Tyr Cys Arg Asn Pro Asp Asn Asp Pro Gln
    50                  55                  60

Gly Pro Trp Cys Tyr Thr Thr Asp Pro Glu Lys Arg Tyr Asp Tyr Cys
65                  70                  75                  80

Asp Ile Leu Glu Cys Glu Glu Cys Met His Cys Ser Gly Glu Asn
                85                  90                  95

Tyr Asp Gly Lys Ile Ser Lys Thr Met Ser Gly Leu Glu Cys Gln Ala
            100                 105                 110

Trp Asp Ser Gln Ser Pro His Ala His Gly Tyr Ile Pro Ser Lys Phe
        115                 120                 125

Pro Asn Lys Asn Leu Lys Lys Asn Tyr Cys Arg Asn Pro Asp Arg Glu
    130                 135                 140

Leu Arg Pro Trp Cys Phe Thr Thr Asp Pro Asn Lys Arg Trp Glu Leu
145                 150                 155                 160

Cys Asp Ile Pro Arg Cys Thr Thr Pro Pro Ser Ser Gly Pro Thr
                165                 170                 175

Tyr Gln Cys Leu Lys Gly Thr Gly Glu Asn Tyr Arg Gly Asn Val Ala
            180                 185                 190

Val Thr Val Ser Gly His Thr Cys Gln His Trp Ser Ala Gln Thr Pro
            195                 200                 205

His Thr His Asn Arg Thr Pro Glu Asn Phe Pro Cys Lys Asn Leu Asp
        210                 215                 220

Glu Asn Tyr Cys Arg Asn Pro Asp Gly Lys Arg Ala Pro Trp Cys His
225                 230                 235                 240

Thr Thr Asn Ser Gln Val Arg Trp Glu Tyr Cys Lys Ile Pro Ser Cys
                245                 250                 255

Asp Ser Ser Pro Val Ser Thr Glu Gln Leu Ala Pro Thr Ala Pro Pro
            260                 265                 270

Glu Leu Thr Pro Val Val Gln Asp Cys Tyr His Gly Asp Gly Gln Ser
        275                 280                 285

Tyr Arg Gly Thr Ser Ser Thr Thr Thr Thr Gly Lys Lys Cys Gln Ser
    290                 295                 300

Trp Ser Ser Met Thr Pro His Arg His Gln Lys Thr Pro Glu Asn Tyr
305                 310                 315                 320

Pro Asn Ala Gly Leu Thr Met Asn Tyr Cys Arg Asn Pro Asp Ala Asp
                325                 330                 335

Lys Gly Pro Trp Cys Phe Thr Thr Asp Pro Ser Val Arg Trp Glu Tyr
            340                 345                 350

Cys Asn Leu Lys Lys Cys Ser Gly Thr Glu Ala Ser Val Val Ala Pro
        355                 360                 365

Pro Pro Val Val Leu Leu Pro Asp Val Glu Thr Pro Ser Glu Glu Asp
    370                 375                 380

Cys Met Phe Gly Asn Gly Lys Gly Tyr Arg Gly Lys Arg Ala Thr Thr
385                 390                 395                 400
```

-continued

```
Val Thr Gly Thr Pro Cys Gln Asp Trp Ala Ala Gln Glu Pro His Arg
            405                 410                 415
His Ser Ile Phe Thr Pro Glu Thr Asn Pro Arg Ala Gly Leu Glu Lys
        420                 425                 430
Asn Tyr Cys Arg Asn Pro Asp Gly Asp Val Gly Gly Pro Trp Cys Tyr
    435                 440                 445
Thr Thr Asn Pro Arg Lys Leu Tyr Asp Tyr Cys Asp Val Pro Gln Cys
450                 455                 460
Ala Ala Pro Ser Phe Asp Cys Gly Lys Pro Gln Val Glu Pro Lys Lys
465                 470                 475                 480
Cys Pro Gly Arg Val Val Gly Gly Cys Val Ala His Pro His Ser Trp
                485                 490                 495
Pro Trp Gln Val Ser Leu Arg Thr Arg Phe Gly Met His Phe Cys Gly
            500                 505                 510
Gly Thr Leu Ile Ser Pro Glu Trp Val Leu Thr Ala Ala His Cys Leu
        515                 520                 525
Glu Lys Ser Pro Arg Pro Ser Ser Tyr Lys Val Ile Leu Gly Ala His
    530                 535                 540
Gln Glu Val Asn Leu Glu Pro His Val Gln Glu Ile Glu Val Ser Arg
545                 550                 555                 560
Leu Phe Leu Glu Pro Thr Arg Lys Asp Ile Ala Leu Leu Lys Leu Ser
                565                 570                 575
Ser Pro Ala Val Ile Thr Asp Lys Val Ile Pro Ala Cys Leu Pro Ser
            580                 585                 590
Pro Asn Tyr Val Val Ala Asp Arg Thr Glu Cys Phe Ile Thr Gly Trp
        595                 600                 605
Gly Glu Thr Gln Gly Thr Phe Gly Ala Gly Leu Leu Lys Glu Ala Gln
    610                 615                 620
Leu Pro Val Ile Glu Asn Lys Val Cys Asn Arg Tyr Glu Phe Leu Asn
625                 630                 635                 640
Gly Arg Val Gln Ser Thr Glu Leu Cys Ala Gly His Leu Ala Gly Gly
                645                 650                 655
Thr Asp Ser Cys Gln Gly Asp Ser Gly Gly Pro Leu Val Cys Phe Glu
            660                 665                 670
Lys Asp Lys Tyr Ile Leu Gln Gly Val Thr Ser Trp Gly Leu Gly Cys
        675                 680                 685
Ala Arg Pro Asn Lys Pro Gly Val Tyr Val Arg Val Ser Arg Phe Val
    690                 695                 700
Thr Trp Ile Glu Gly Val Met Arg Asn Asn
705                 710
```

<210> SEQ ID NO 7
<211> LENGTH: 1245
<212> TYPE: DNA
<213> ORGANISM: Artificial Sequence
<220> FEATURE:
<223> OTHER INFORMATION: nucleotide sequence coding for delta-plg or
      delta-plasminogen

<400> SEQUENCE: 7

```
gagcctctgg atgactatgt gaatacccag ggggcttcac tgttcagtgt cactaagaag      60
cagctgggag caggaagtat agaagaatgt gcagcaaaat gtgaggagga cgaagaattc     120
acctgcaggg cattccaata tcacagtaaa gagcaacaat gtgtgataat ggctgaaaac     180
aggaagtcct ccataatcat taggatgaga gatgtagttt atttgaaaaa gaaagtgtat     240
```

-continued

```
ctctcagagt gcaagactgg gaatggaaag aactacagag ggacgatgtc caaaacaaaa      300
aatggcatca cctgtcaaaa atggagttcc acttctcccc acagacctag attctcacct      360
gctacacacc cctcagaggg actggaggag aactactgca ggaatccaga caacgatccg      420
caggggccct ggtgctatac tactgatcca gaaaagagat atgactactg cgacattctt      480
gagtgtgaag aggcggcccc ttcatttgat tgtgggaagc ctcaagtgga gccgaagaaa      540
tgtcctggaa gggttgtagg ggggtgtgtg gcccacccac attcctggcc ctggcaagtc      600
agtcttagaa caaggtttgg aatgcacttc tgtggaggca ccttgatatc cccagagtgg      660
gtgttgactg ctgcccactg cttggagaag tccccaaggc cttcatccta caaggtcatc      720
ctgggtgcac accaagaagt gaatctcgaa ccgcatgttc aggaaataga agtgtctagg      780
ctgttcttgg agcccacacg aaaagatatt gccttgctaa agctaagcag tcctgccgtc      840
atcactgaca aagtaatccc agcttgtctg ccatccccaa attatgtggt cgctgaccgg      900
accgaatgtt tcatcactgg ctggggagaa acccaaggta cttttggagc tggccttctc      960
aaggaagccc agctccctgt gattgagaat aaagtgtgca atcgctatga gtttctgaat     1020
ggaagagtcc aatccaccga actctgtgct gggcatttgg ccggaggcac tgacagttgc     1080
cagggtgaca gtggaggtcc tctggttttgc ttcgagaagg acaaatacat tttacaagga     1140
gtcacttctt ggggtcttgg ctgtgcacgc cccaataagc ctggtgtcta tgttcgtgtt     1200
tcaaggtttg ttacttggat tgagggagtg atgagaaata attaa                     1245
```

<210> SEQ ID NO 8
<211> LENGTH: 414
<212> TYPE: PRT
<213> ORGANISM: Artificial Sequence
<220> FEATURE:
<223> OTHER INFORMATION: amino acid sequence of delta-plg or
      delta-plasminogen

<400> SEQUENCE: 8

```
Glu Pro Leu Asp Asp Tyr Val Asn Thr Gln Gly Ala Ser Leu Phe Ser
1               5                   10                  15

Val Thr Lys Lys Gln Leu Gly Ala Gly Ser Ile Glu Glu Cys Ala Ala
            20                  25                  30

Lys Cys Glu Glu Asp Glu Glu Phe Thr Cys Arg Ala Phe Gln Tyr His
        35                  40                  45

Ser Lys Glu Gln Gln Cys Val Ile Met Ala Glu Asn Arg Lys Ser Ser
    50                  55                  60

Ile Ile Ile Arg Met Arg Asp Val Val Leu Phe Glu Lys Lys Val Tyr
65                  70                  75                  80

Leu Ser Glu Cys Lys Thr Gly Asn Gly Lys Asn Tyr Arg Gly Thr Met
                85                  90                  95

Ser Lys Thr Lys Asn Gly Ile Thr Cys Gln Lys Trp Ser Ser Thr Ser
            100                 105                 110

Pro His Arg Pro Arg Phe Ser Pro Ala Thr His Pro Ser Glu Gly Leu
        115                 120                 125

Glu Glu Asn Tyr Cys Arg Asn Pro Asp Asn Asp Pro Gln Gly Pro Trp
    130                 135                 140

Cys Tyr Thr Thr Asp Pro Glu Lys Arg Tyr Asp Tyr Cys Asp Ile Leu
145                 150                 155                 160

Glu Cys Glu Glu Ala Ala Pro Ser Phe Asp Cys Gly Lys Pro Gln Val
                165                 170                 175
```

```
Glu Pro Lys Lys Cys Pro Gly Arg Val Val Gly Cys Val Ala His
            180                 185                 190
Pro His Ser Trp Pro Trp Gln Val Ser Leu Arg Thr Arg Phe Gly Met
        195                 200                 205
His Phe Cys Gly Gly Thr Leu Ile Ser Pro Glu Trp Val Leu Thr Ala
    210                 215                 220
Ala His Cys Leu Glu Lys Ser Pro Arg Pro Ser Ser Tyr Lys Val Ile
225                 230                 235                 240
Leu Gly Ala His Gln Glu Val Asn Leu Glu Pro His Val Gln Glu Ile
            245                 250                 255
Glu Val Ser Arg Leu Phe Leu Glu Pro Thr Arg Lys Asp Ile Ala Leu
        260                 265                 270
Leu Lys Leu Ser Ser Pro Ala Val Ile Thr Asp Lys Val Ile Pro Ala
    275                 280                 285
Cys Leu Pro Ser Pro Asn Tyr Val Val Ala Asp Arg Thr Glu Cys Phe
    290                 295                 300
Ile Thr Gly Trp Gly Glu Thr Gln Gly Thr Phe Gly Ala Gly Leu Leu
305                 310                 315                 320
Lys Glu Ala Gln Leu Pro Val Ile Glu Asn Lys Val Cys Asn Arg Tyr
            325                 330                 335
Glu Phe Leu Asn Gly Arg Val Gln Ser Thr Glu Leu Cys Ala Gly His
        340                 345                 350
Leu Ala Gly Gly Thr Asp Ser Cys Gln Gly Asp Ser Gly Gly Pro Leu
    355                 360                 365
Val Cys Phe Glu Lys Asp Lys Tyr Ile Leu Gln Gly Val Thr Ser Trp
    370                 375                 380
Gly Leu Gly Cys Ala Arg Pro Asn Lys Pro Gly Val Tyr Val Arg Val
385                 390                 395                 400
Ser Arg Phe Val Thr Trp Ile Glu Gly Val Met Arg Asn Asn
            405                 410
```

<210> SEQ ID NO 9
<211> LENGTH: 1104
<212> TYPE: DNA
<213> ORGANISM: Artificial Sequence
<220> FEATURE:
<223> OTHER INFORMATION: nucleotide sequence coding for Mini-plg or mini-plasminogen

<400> SEQUENCE: 9

```
gtcaggtggg agtactgcaa cctgaaaaaa tgctcaggaa cagaagcgag tgttgtagca    60
cctccgcctg ttgtcctgct tccagatgta gagactcctt ccgaagaaga ctgtatgttt   120
gggaatggga aggataccg aggcaagagg gcgaccactg ttactgggac gccatgccag    180
gactgggctg cccaggagcc ccatagacac agcattttca ctccagagac aaatccacgg   240
gcgggtctgg aaaaaaatta ctgccgtaac cctgatggtg atgtaggtgg tcctctggtgc  300
tacacgacaa atccaagaaa actttacgac tactgtgatg tccctcagtg tgcggcccct   360
tcatttgatt gtgggaagcc tcaagtggag ccgaagaaat gtcctggaag ggttgtaggg   420
gggtgtgtgg cccacccaca ttcctggccc tggcaagtca gtcttagaac aaggtttgga   480
atgcacttct gtggaggcac cttgatatcc ccagagtggg tgttgactgc tgcccactgc   540
ttggagaagt ccccaaggcc ttcatcctac aaggtcatcc tgggtgcaca ccaagaagtg   600
aatctcgaac gcatgttca ggaaatagaa gtgtctaggc tgttcttgga gcccacacga    660
aaagatattg ccttgctaaa gctaagcagt cctgccgtca tcactgacaa agtaatccca   720
```

```
gcttgtctgc catccccaaa ttatgtggtc gctgaccgga ccgaatgttt catcactggc    780
tggggagaaa cccaaggtac ttttggagct ggccttctca aggaagccca gctccctgtg    840
attgagaata aagtgtgcaa tcgctatgag tttctgaatg gaagagtcca atccaccgaa    900
ctctgtgctg gcatttggc cggaggcact gacagttgcc agggtgacag tggaggtcct    960
ctggtttgct tcgagaagga caaatacatt ttacaaggag tcacttcttg gggtcttggc   1020
tgtgcacgcc ccaataagcc tggtgtctat gttcgtgttt caaggtttgt tacttggatt   1080
gagggagtga tgagaaataa ttaa                                          1104
```

<210> SEQ ID NO 10
<211> LENGTH: 367
<212> TYPE: PRT
<213> ORGANISM: Artificial Sequence
<220> FEATURE:
<223> OTHER INFORMATION: amino acid sequence of Mini-plg or
      mini-plasminogen <400> SEQUENCE: 10

```
Val Arg Trp Glu Tyr Cys Asn Leu Lys Lys Cys Ser Gly Thr Glu Ala
1               5                   10                  15

Ser Val Val Ala Pro Pro Val Val Leu Leu Pro Asp Val Glu Thr
            20                  25                  30

Pro Ser Glu Glu Asp Cys Met Phe Gly Asn Gly Lys Gly Tyr Arg Gly
        35                  40                  45

Lys Arg Ala Thr Thr Val Thr Gly Thr Pro Cys Gln Asp Trp Ala Ala
    50                  55                  60

Gln Glu Pro His Arg His Ser Ile Phe Thr Pro Glu Thr Asn Pro Arg
65                  70                  75                  80

Ala Gly Leu Glu Lys Asn Tyr Cys Arg Asn Pro Asp Gly Asp Val Gly
                85                  90                  95

Gly Pro Trp Cys Tyr Thr Thr Asn Pro Arg Lys Leu Tyr Asp Tyr Cys
            100                 105                 110

Asp Val Pro Gln Cys Ala Ala Pro Ser Phe Asp Cys Gly Lys Pro Gln
        115                 120                 125

Val Glu Pro Lys Lys Cys Pro Gly Arg Val Val Gly Gly Cys Val Ala
    130                 135                 140

His Pro His Ser Trp Pro Trp Gln Val Ser Leu Arg Thr Arg Phe Gly
145                 150                 155                 160

Met His Phe Cys Gly Gly Thr Leu Ile Ser Pro Glu Trp Val Leu Thr
                165                 170                 175

Ala Ala His Cys Leu Glu Lys Ser Pro Arg Pro Ser Ser Tyr Lys Val
            180                 185                 190

Ile Leu Gly Ala His Gln Glu Val Asn Leu Glu Pro His Val Gln Glu
        195                 200                 205

Ile Glu Val Ser Arg Leu Phe Leu Glu Pro Thr Arg Lys Asp Ile Ala
    210                 215                 220

Leu Leu Lys Leu Ser Ser Pro Ala Val Ile Thr Asp Lys Val Ile Pro
225                 230                 235                 240

Ala Cys Leu Pro Ser Pro Asn Tyr Val Val Ala Asp Arg Thr Glu Cys
                245                 250                 255

Phe Ile Thr Gly Trp Gly Glu Thr Gln Gly Thr Phe Gly Ala Gly Leu
            260                 265                 270

Leu Lys Glu Ala Gln Leu Pro Val Ile Glu Asn Lys Val Cys Asn Arg
        275                 280                 285
```

Tyr Glu Phe Leu Asn Gly Arg Val Gln Ser Thr Glu Leu Cys Ala Gly
            290                 295                 300

His Leu Ala Gly Gly Thr Asp Ser Cys Gln Gly Asp Ser Gly Gly Pro
305                 310                 315                 320

Leu Val Cys Phe Glu Lys Asp Lys Tyr Ile Leu Gln Gly Val Thr Ser
                325                 330                 335

Trp Gly Leu Gly Cys Ala Arg Pro Asn Lys Pro Gly Val Tyr Val Arg
            340                 345                 350

Val Ser Arg Phe Val Thr Trp Ile Glu Gly Val Met Arg Asn Asn
            355                 360                 365

<210> SEQ ID NO 11
<211> LENGTH: 750
<212> TYPE: DNA
<213> ORGANISM: Artificial Sequence
<220> FEATURE:
<223> OTHER INFORMATION: nucleotide sequence coding for Micro-plg or
      micro-plasminogen

<400> SEQUENCE: 11
gcccCttcat tgattgtgg gaagcctcaa gtggagccga agaaatgtcc tggaagggtt      60
gtaggggggt gtgtggccca cccacattcc tggccctggc aagtcagtct tagaacaagg    120
tttggaatgc acttctgtgg aggcaccttg atatccccag agtgggtgtt gactgctgcc    180
cactgcttgg agaagtcccc aaggccttca tcctacaagg tcatcctggg tgcacaccaa    240
gaagtgaatc tcgaaccgca tgttcaggaa atagaagtgt ctaggctgtt cttggagccc    300
acacgaaaag atattgcctt gctaaagcta agcagtcctg ccgtcatcac tgacaaagta    360
atcccagctt gtctgccatc cccaaattat gtggtcgctg accggaccga atgtttcatc    420
actggctggg agaaacccca aggtactttt ggagctggcc ttctcaagga agcccagctc    480
cctgtgattg agaataaagt gtgcaatcgc tatgagtttc tgaatggaag agtccaatcc    540
accgaactct gtgctgggca tttggccgga ggcactgaca gttgccaggg tgacagtgga    600
ggtcctctgg tttgcttcga gaaggacaaa tacattttac aaggagtcac ttcttggggt    660
cttggctgtg cacgccccaa taagcctggt gtctatgttc gtgtttcaag gtttgttact    720
tggattgagg gagtgatgag aaataattaa                                     750

<210> SEQ ID NO 12
<211> LENGTH: 249
<212> TYPE: PRT
<213> ORGANISM: Artificial Sequence
<220> FEATURE:
<223> OTHER INFORMATION: amino acid sequence coding for Micro-plg or
      micro-plasminogen

<400> SEQUENCE: 12

Ala Pro Ser Phe Asp Cys Gly Lys Pro Gln Val Glu Pro Lys Lys Cys
1               5                   10                  15

Pro Gly Arg Val Val Gly Gly Cys Val Ala His Pro His Ser Trp Pro
            20                  25                  30

Trp Gln Val Ser Leu Arg Thr Arg Phe Gly Met His Phe Cys Gly Gly
        35                  40                  45

Thr Leu Ile Ser Pro Glu Trp Val Leu Thr Ala Ala His Cys Leu Glu
    50                  55                  60

Lys Ser Pro Arg Pro Ser Ser Tyr Lys Val Ile Leu Gly Ala His Gln
65                  70                  75                  80

Glu Val Asn Leu Glu Pro His Val Gln Ile Glu Val Ser Arg Leu
            85                  90                  95

Phe Leu Glu Pro Thr Arg Lys Asp Ile Ala Leu Leu Lys Leu Ser Ser
        100                 105                 110

Pro Ala Val Ile Thr Asp Lys Val Ile Pro Ala Cys Leu Pro Ser Pro
            115                 120                 125

Asn Tyr Val Val Ala Asp Arg Thr Glu Cys Phe Ile Thr Gly Trp Gly
        130                 135                 140

Glu Thr Gln Gly Thr Phe Gly Ala Gly Leu Leu Lys Glu Ala Gln Leu
145                 150                 155                 160

Pro Val Ile Glu Asn Lys Val Cys Asn Arg Tyr Glu Phe Leu Asn Gly
            165                 170                 175

Arg Val Gln Ser Thr Glu Leu Cys Ala Gly His Leu Ala Gly Gly Thr
        180                 185                 190

Asp Ser Cys Gln Gly Asp Ser Gly Gly Pro Leu Val Cys Phe Glu Lys
        195                 200                 205

Asp Lys Tyr Ile Leu Gln Gly Val Thr Ser Trp Gly Leu Gly Cys Ala
210                 215                 220

Arg Pro Asn Lys Pro Gly Val Tyr Val Arg Val Ser Arg Phe Val Thr
225                 230                 235                 240

Trp Ile Glu Gly Val Met Arg Asn Asn
                245

<210> SEQ ID NO 13
<211> LENGTH: 684
<212> TYPE: DNA
<213> ORGANISM: Artificial Sequence
<220> FEATURE:
<223> OTHER INFORMATION: nucleotide sequence coding for the serine
      protease domain

<400> SEQUENCE: 13
gttgtagggg ggtgtgtggc ccacccacat tcctggccct ggcaagtcag tcttagaaca      60
aggtttggaa tgcacttctg tggaggcacc ttgatatccc agagtgggt gttgactgct     120 gcccactgct tggagaagtc cccaaggcct tcatcctaca aggtcatcct gggtgcacac     180
caagaagtga atctcgaacc gcatgttcag gaaatagaag tgtctaggct gttcttggag     240
cccacacgaa aagatattgc cttgctaaag ctaagcagtc ctgccgtcat cactgacaaa     300
gtaatcccag cttgtctgcc atccccaaat tatgtggtcg ctgaccggac cgaatgtttc     360
atcactggct ggggagaaac ccaaggtact tttggagctg gccttctcaa ggaagcccag     420
ctccctgtga ttgagaataa agtgtgcaat cgctatgagt ttctgaatgg aagagtccaa     480
tccaccgaac tctgtgctgg catttggcc ggaggcactg acagttgcca gggtgacagt     540
ggaggtcctc tggtttgctt cgagaaggac aaatacattt tacaaggagt cacttcttgg     600
ggtcttggct gtgcacgccc caataagcct ggtgtctatg ttcgtgtttc aaggtttgtt     660
acttggattg agggagtgat gaga                                            684

<210> SEQ ID NO 14
<211> LENGTH: 228
<212> TYPE: PRT
<213> ORGANISM: Artificial Sequence
<220> FEATURE:
<223> OTHER INFORMATION: amino acid sequence coding for the serine
      protease domain

<400> SEQUENCE: 14

```
Val Val Gly Gly Cys Val Ala His Pro His Ser Trp Pro Trp Gln Val
1               5               10                  15

Ser Leu Arg Thr Arg Phe Gly Met His Phe Cys Gly Gly Thr Leu Ile
            20              25                  30

Ser Pro Glu Trp Val Leu Thr Ala Ala His Cys Leu Glu Lys Ser Pro
        35                  40                  45

Arg Pro Ser Ser Tyr Lys Val Ile Leu Gly Ala His Gln Glu Val Asn
    50              55                  60

Leu Glu Pro His Val Gln Glu Ile Glu Val Ser Arg Leu Phe Leu Glu
65                  70                  75                  80

Pro Thr Arg Lys Asp Ile Ala Leu Leu Lys Leu Ser Ser Pro Ala Val
            85                  90                  95

Ile Thr Asp Lys Val Ile Pro Ala Cys Leu Pro Ser Pro Asn Tyr Val
            100                 105                 110

Val Ala Asp Arg Thr Glu Cys Phe Ile Thr Gly Trp Gly Glu Thr Gln
            115                 120                 125

Gly Thr Phe Gly Ala Gly Leu Leu Lys Glu Ala Gln Leu Pro Val Ile
        130                 135                 140

Glu Asn Lys Val Cys Asn Arg Tyr Glu Phe Leu Asn Gly Arg Val Gln
145                 150                 155                 160

Ser Thr Glu Leu Cys Ala Gly His Leu Ala Gly Gly Thr Asp Ser Cys
                165                 170                 175

Gln Gly Asp Ser Gly Gly Pro Leu Val Cys Phe Glu Lys Asp Lys Tyr
            180                 185                 190

Ile Leu Gln Gly Val Thr Ser Trp Gly Leu Gly Cys Ala Arg Pro Asn
            195                 200                 205

Lys Pro Gly Val Tyr Val Arg Val Ser Arg Phe Val Thr Trp Ile Glu
    210                 215                 220

Gly Val Met Arg
225
```